US010246410B2

(12) United States Patent
Zhou et al.

(10) Patent No.: US 10,246,410 B2
(45) Date of Patent: Apr. 2, 2019

(54) HYDRAZINYL AND AMINOOXY COMPOUNDS AND THEIR METHODS OF USE

(71) Applicant: LIFE TECHNOLOGIES CORPORATION, Carlsbad, CA (US)

(72) Inventors: Wenjun Zhou, Eugene, OR (US); Kyle Gee, Springfield, OR (US); Yolanda Tennico, San Marcos, CA (US); Peter Slade, St Louis, MO (US); Hee Chol Kang, Eugene, OR (US); Shaheer Khan, Foster City, CA (US); Brian Evans, Mountain View, CA (US); James Stray, San Mateo, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 15/529,437

(22) PCT Filed: Dec. 3, 2015

(86) PCT No.: PCT/US2015/063593
§ 371 (c)(1),
(2) Date: May 24, 2017

(87) PCT Pub. No.: WO2016/090076
PCT Pub. Date: Jun. 9, 2016

(65) Prior Publication Data
US 2017/0369431 A1 Dec. 28, 2017

Related U.S. Application Data

(60) Provisional application No. 62/087,034, filed on Dec. 3, 2014.

(51) Int. Cl.
*C07C 309/47* (2006.01)
*G01N 33/58* (2006.01)
*C07D 311/84* (2006.01)
*C07C 309/51* (2006.01)

(52) U.S. Cl.
CPC .......... *C07C 309/47* (2013.01); *C07C 309/51* (2013.01); *C07D 311/84* (2013.01); *G01N 33/582* (2013.01); *C07C 2603/50* (2017.05); *G01N 2400/10* (2013.01)

(58) Field of Classification Search
CPC .................................................... C07C 309/47
USPC ........................................................ 549/223
See application file for complete search history.

(56) References Cited

U.S. PATENT DOCUMENTS

| 5,140,104 A | * | 8/1992 | Coughlin | ........... | A61K 41/0042 530/330 |
| 5,521,290 A | * | 5/1996 | Sivam | ................ | A61K 51/1093 530/391.5 |
| 5,633,351 A | * | 5/1997 | Reed | .................. | A61K 51/1093 424/9.34 |

FOREIGN PATENT DOCUMENTS

| HU | 189204 B | 6/1986 | |
| WO | WO-87/06837 | 11/1987 | |
| WO | WO 8706837 | * 11/1987 | ............. A61K 39/00 |
| WO | WO-2013/173494 | 11/2013 | |

OTHER PUBLICATIONS

Database Caplus, , "Cholecystokinin octapeptide sulfate ester and its salts", *Chemical Abstracts Service*, Columbus, Ohio, Feb. 4, 1989.
Database Caplus, , "L-Aspartic acid, N-[(9H-fluoren-9-ylmethoxy)carbonyl]-, 1-hydrazide, mono(trifluoroacetate)", *Chemical Abstracts Service*, Columbus, Ohio, Dec. 17, 1984.
Database Caplus, , "Preparation of antibody conjugates of amine derivatives of folic acid analogs", *Chemical Abstracts Service*, Columbus, Ohio, Jan. 13, 1998.
Database Registry, , "L-Glutamic acid, N-[4-[[(2, 4-diamino-6-pteridinyl) methyl] am ino] benzoyl]-, 1-hydrazide", *Chemical Abstracts Service*, Columbus, Ohio, Jan. 13, 1989.
Leteux, C. et al., "Biotinyl-L-3(2-naphthyl)-alanine hydrazide derivatives of N-glycans: versatile solid-phase probes for carbohydrate-recognition studies", *Glycobiology*, vol. 8, No. 3, 1998, 227-236.

* cited by examiner

*Primary Examiner* — Nizal S Chandrakumar

(57) ABSTRACT

The present disclosure is directed dye compounds containing a hydrazinyl substituent and optionally, one or more negatively charged groups, such as sulfonate, phosphate, phosphonate, and/or carboxylate groups and dye compounds containing an aminooxy substitutent. The compounds are useful in the detection of analytes containing aldehyde and ketone groups, including, for example, glycans.

32 Claims, 22 Drawing Sheets

HYDRAZINYL AND AMINOOXY COMPOUNDS AND THEIR METHODS OF USE

CROSS-REFERENCE

This application is a 371 National Stage of PCT/US2015/063593, filed Dec. 3, 2015, which claims the benefit of U.S. Provisional Application No. 62/087,034, filed Dec. 3, 2014, the disclosures of which are hereby incorporated by reference in their entireties.

PCT/US2015/063791 entitled "Charged Reactive Oligomers", was filed on even date of Dec. 3, 2015, which claims the benefit of U.S. Provisional Application No. 62/087,208 entitled "Charged Reactive Oligomers", filed on Dec. 3, 2014, the disclosures of which are each hereby incorporated by reference in their entireties for all purposes.

FIELD

Dye compounds containing a hydrazinyl substituent and optionally, one or more negatively charged groups, such as sulfonate, phosphate, phosphonate, and/or carboxylate groups, are described. Dye compounds containing an aminooxy substituent and one or more negatively charged groups are also described herein. The compounds are useful in the labeling and detection of analytes containing aldehyde and ketone groups, including, for example, glycans.

BACKGROUND

A myriad of biomarkers containing aldehyde and ketone moieties exist and can play an important role in the biological, forensic, medical and industrial sciences. In particular, aldehydes and ketones are known to be key end products in the degradation of a variety of biological molecules, such as, lipids, nucleic acids, carbohydrates and proteins. In a number of instances, these end products are a result of oxidative stress.

A number of reagents for the detection of aldehyde and ketone-containing moieties have been proposed, however, each with limited success. Among the most widely used of such reagents are dansyl hydrazine, fluorescein thiosemicarbazide, various biotin hydrazides, biotin hydroxylamine (ARP), and various aromatic amines (such as 2-aminopyridine, 8-aminonaphthalene-1,3,6-disulfonic acid, 1-aminopyrene-3,6,8-trisulfonic acid, 2-aminoacridone, and 8-amino-1,3,6-pyrene trisulfonic acid (APTS)). Unfortunately, use of these reagents requires additional purification and/or secondary reagents.

Existing methods of labeling carbohydrates that utilize hydrazine, hydroxylamine and amine derivatization reagents have focused on labeling aldehydes present in, or introduced into, carbohydrates, particularly the so-called "reducing sugars". Aldehydes are typically introduced into carbohydrates by periodate oxidation. The adduct formed with the reducing sugar typically needs to be stabilized by treatment with borohydride or cyanoborohydride, both of which are toxic materials and present hazards to the user and for disposal. The derivatization reaction typically precedes or is followed by a separation technique such as chromatography, electrophoresis, precipitation, affinity isolation or other means before direct or indirect detection of the labeled product. Therefore, there is a need for reagents that permit rapid in situ detection of aldehyde and ketone moieties upon contact and that do not require reductive amination in order to stabilize the adduct.

SUMMARY

The present disclosure provides dye compounds containing a hydrazinyl substituent and optionally, one or more negatively charged groups, including but not limited to, sulfonate, phosphate, phosphonate, and carboxylate groups, and dye compounds containing an aminooxy substituent and one or more negatively charged groups, for example, sulfonate. The present disclosure provides methods of using such dye compounds for labeling aldehyde and ketone containing molecules or analytes, such as glycans. The dye compounds provided herein are capable of binding aldehyde and ketone containing analytes in solution, thereby indicating the presence of the analyte.

Certain embodiments provide a compound of Formula (I) or a tautomer or salt thereof:

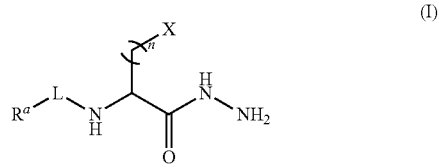

(I)

wherein,

L is a linker;

$R^a$ is a reporter molecule, carrier molecule or a solid support;

n is an integer from 1 to 24; and

X is a molecule containing $SO_3H$, $SO_3^-$, $OPO_3^{2-}$, $OPO_3H_2$, $PO_3H_2$, $PO_3^{2-}$, COOH, or $COO^-$.

In certain embodiments, L is a covalent bond, -alkyl, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is a dye. More particularly, the dye is a pyrene, a xanthene, a cyanine, an indole, a benzofuran, a coumarin, or a borapolyazaindacine.

In certain embodiments, $R^a$ is a chelating moiety, a hapten, an antibody, an enzyme, a radiolabel, a metal ion or metal ion containing substance, a pigment, a chromogen, a phosphor, a fluorogen, a bioluminescent substance, a chemiluminescent substance, or a semiconductor nanocrystal. More particularly, $R^a$ is avidin, streptavidin or an analog thereof.

In certain embodiments, $R^a$ is a solid support.

In certain embodiments, $R^a$ is a carrier molecule. More particularly, the carrier molecule is selected from the group consisting of an amino acid, a peptide, a protein, a carbohydrate, a polysaccharide, a nucleoside, a nucleotide, an oligonucleotide, a nucleic acid polymer, a drug, a lipid, and a synthetic polymer.

In certain embodiments, the compound of Formula (I) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, $R^a$ is:

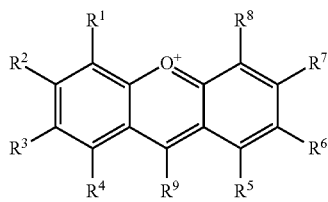

or a tautomer or salt thereof;
wherein,
$R^1$, $R^2$, $R^3$, $R^4$, $R^5$, $R^6$, $R^7$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or one or more of $R^1$ and $R^2$, $R^2$ and $R^3$, $R^3$ and $R^4$, $R^5$ and $R^6$, $R^6$ and $R^7$ or $R^7$ and $R^8$ are taken together to form a fused aryl or heteroaryl group; and
one of $R^1$, $R^2$, $R^3$, $R^4$, $R^5$, $R^6$, $R^7$, $R^8$ and $R^9$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

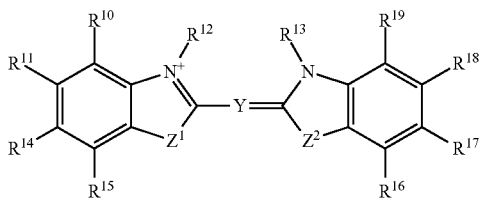

or a tautomer or salt thereof;
wherein,
$Z^1$ and $Z^2$ are each independently O, S, $NR^{23}$ or $CR^{24}R^{25}$;
Y is $-CR^{20}=(CR^{21}-CR^{22}=)_p$;
p is 0, 1, 2, or 3;
$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$, $R^{13}$ and $R^{23}$ are each independently H, alkyl, substituted alkyl, cycloalkyl, substituted cycloalkyl, aryl, substituted aryl, heteroaryl, substituted heteroaryl, heterocyclyl, substituted heterocyclyl;
$R^{20}$, $R^{21}$ and $R^{22}$ are each independently, H, alkyl, substituted alkyl, cycloalkyl, substituted cycloalkyl, aryl, substituted aryl, heteroaryl, or substituted heteroaryl;
$R^{24}$ and $R^{25}$ are H, alkyl or substituted alkyl; and
one of $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

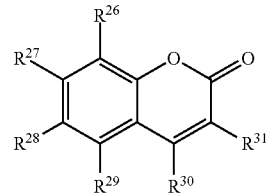

or a tautomer or salt thereof;
wherein,
$R^{26}$, $R^{27}$, $R^{28}$, $R^{29}$, $R^{30}$ and $R^{31}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
one of $R^{26}$, $R^{27}$, $R^{28}$, $R^{29}$, $R^{30}$ and $R^{31}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

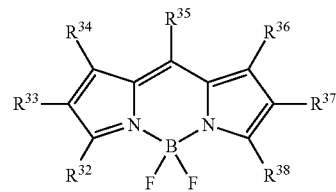

or a tautomer or salt thereof;

wherein, $R^{32}$, $R^{33}$, $R^{34}$, $R^{35}$, $R^{36}$, $R^{37}$ and $R^{38}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{32}$, $R^{33}$, $R^{34}$, $R^{35}$, $R^{36}$, $R^{37}$ and $R^{38}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

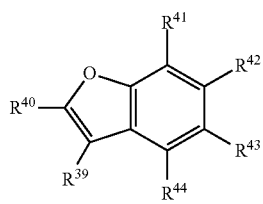

or a tautomer or salt thereof;

wherein, $R^{39}$, $R^{40}$, $R^{41}$, $R^{42}$, $R^{43}$ and $R^{44}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{39}$, $R^{40}$, $R^{41}$, $R^{42}$, $R^{43}$ and $R^{44}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

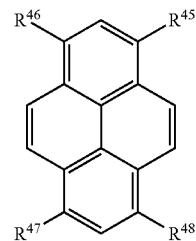

or a tautomer or salt thereof;

wherein, $R^{45}$, $R^{46}$, $R^{47}$, and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{45}$, $R^{46}$, $R^{47}$, and $R^{48}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

Certain embodiments provide a compound of Formula (II) or a tautomer or salt thereof:

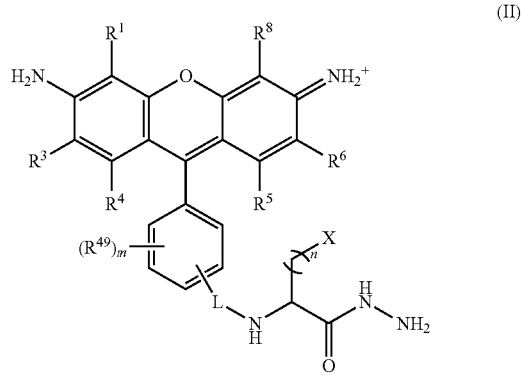

(II)

wherein,

L is a linker;

n is an integer from 1 to 24;

X is a molecule containing $SO_3H$, $SO_3^-$, $OPO_3^{2-}$, $OPO_3H_2$, $PO_3H_2$, $PO_3^{2-}$, COOH, or $COO^-$;

$R^1$, $R^3$, $R^4$, $R^5$, $R^6$, $R^8$ and $R^{49}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and m is 0, 1, or 2.

In certain embodiments, $R^1$ and $R^8$ are each sulfo; $R^2$, $R^3$, $R^4$, $R^5$, $R^6$, and $R^7$ are each H; $R^{49}$ is carboxy; m is 1; L is —C=O; X is selected from N[(CH$_2$)$_3$SO$_3$H]$_2$, SO$_3$H, SO$_3^-$, OPO$_3^{2-}$, OPO$_3$H$_2$, PO$_3$H$_2$, PO$_3^{2-}$, COOH, and COO$^-$; and n is 1, 2, 3 or 4.

In certain embodiments, the compound of Formula (II) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, provided herein is a compound of Formula (III) or a tautomer or salt thereof:

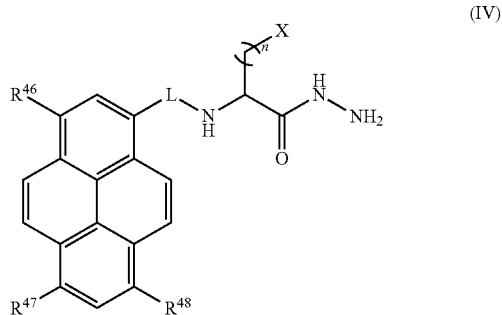

wherein,

Y is —CR$^{20}$=(CR$^{21}$—CR$^{22}$=)$_p$;

p is 0, 1, 2, or 3;

$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$ and $R^{13}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{50}$ is alkyl; and wherein one of $R^{13}$ or $R^{50}$ is:

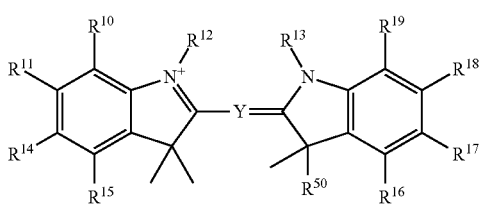

L is a linker;

n is an integer from 1 to 24; and

X is a molecule containing SO$_3$H, SO$_3^-$, OPO$_3^{2-}$, OPO$_3$H$_2$, PO$_3$H$_2$, PO$_3^{2-}$, COOH, or COO$^-$.

In certain embodiments, $R^{50}$ is methyl.

In certain embodiments, the compound of Formula (III) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

Certain embodiments provide a compound of Formula (IV) or a tautomer or salt thereof:

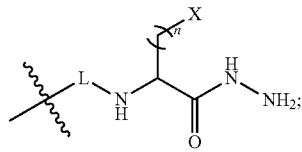

wherein,

L is a linker;

n is an integer from 1 to 24;

X is a molecule containing SO$_3$H, SO$_3^-$, OPO$_3^{2-}$, OPO$_3$H$_2$, PO$_3$H$_2$, PO$_3^{2-}$, COOH, or COO$^-$; and $R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl.

In certain embodiments, $R^{46}$, $R^{47}$, and $R^{48}$ are each sulfo; X is carboxy; n is 1 or 2; and L is

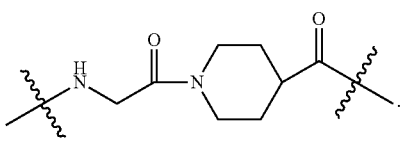 [SMILES: *NCC(=O)N1CCC(C(*)=O)CC1]

In certain embodiments, the compound of Formula (IV) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

Certain embodiments provide a compound of Formula (V) or a tautomer or salt thereof:

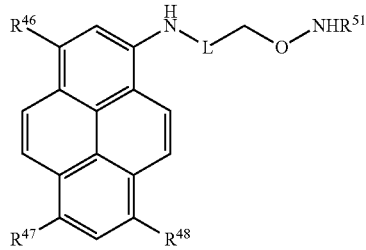

wherein,

L is a linker;

$R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^{51}$ is selected from H, alkyl and substituted alkyl.

In certain embodiments, $R^{46}$, $R^{47}$, and $R^{48}$ are each sulfo, $R^{51}$ is H, and L is selected from the group consisting of: —(CH$_2$)$_5$C(O)NH(CH$_2$)$_2$—, —(CH$_2$)$_6$NHC(O)— and —C(O)—.

In certain embodiments, the compound of Formula (V) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In another aspect, compounds are provided selected from the group consisting of:

Compound 1

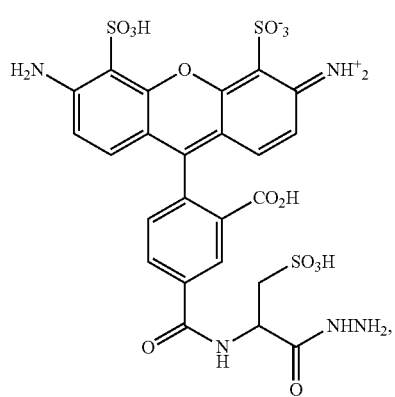

Compound 2

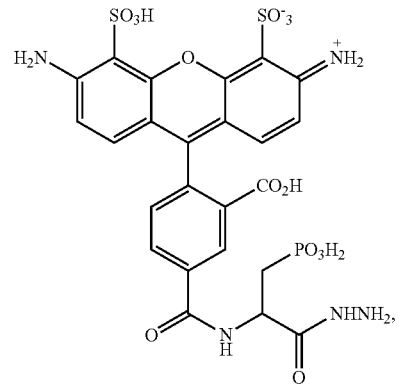

Compound 3

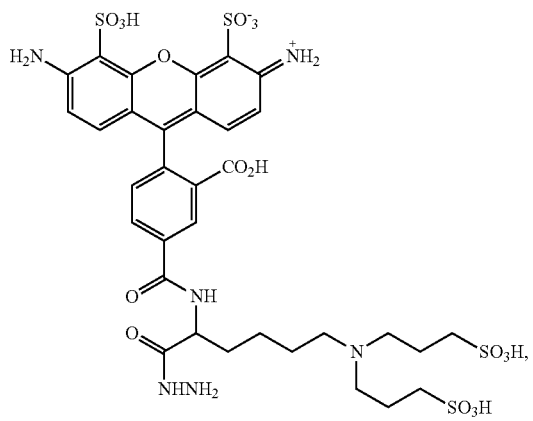

Compound 4

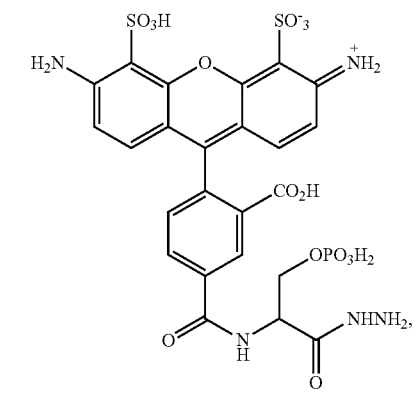

Compound 5

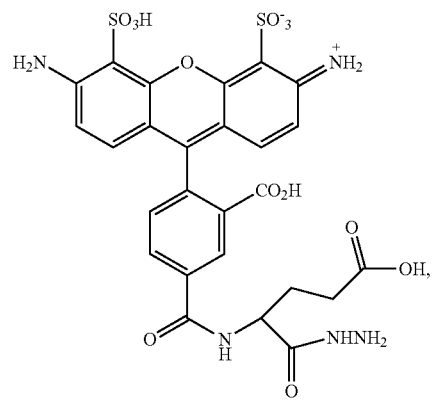

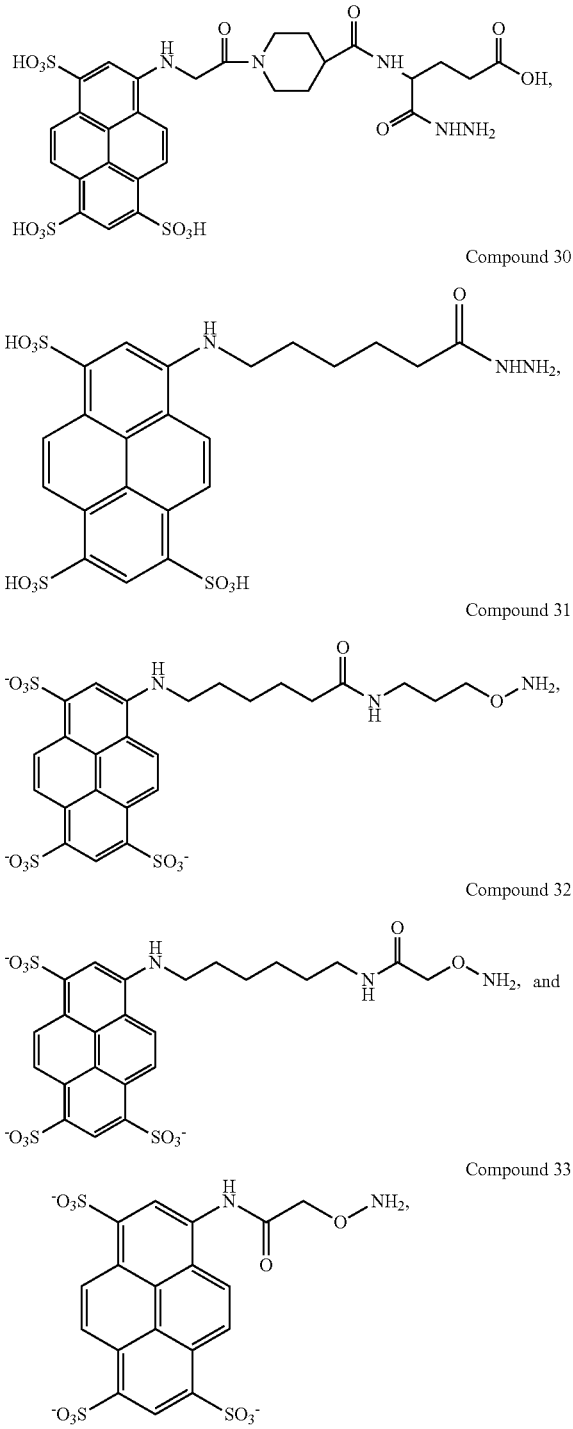

or a salt thereof.

In certain embodiments, the compound is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

Certain embodiments provide compounds comprising any of the dye compounds disclosed herein, wherein the hydrazinyl moiety is unsubstituted or substituted with an analyte.

Certain embodiments provide compounds comprising any of the dye compounds disclosed herein, wherein the aminooxy moiety is unsubstituted or substituted with an analyte.

Certain embodiments provide a composition comprising:
(a) an analyte; and
(b) a compound of the invention.

Certain embodiments provide a composition comprising:
(a) an analyte; and
(b) a compound of Formula (I) or a tautomer or salt thereof:

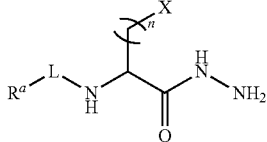

(I)

wherein,
L is a linker;
$R^a$ is a reporter molecule, carrier molecule or a solid support;
n is an integer from 1 to 24; and
X is a molecule containing $SO_3H$, $SO_3^-$, $OPO_3^{2-}$, $OPO_3H_2$, $PO_3H_2$, $PO_3^{2-}$, COOH, or $COO^-$.

In certain embodiments, L is a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is a dye. More particularly, the dye is a pyrene, a xanthene, a cyanine, an indole, a benzofuran, a coumarin, or a borapolyazaindacine.

In certain embodiments, $R^a$ is a chelating moiety, a hapten, an antibody, an enzyme, a radiolabel, a metal ion or metal ion containing substance, a pigment, a chromogen, a phosphor, a fluorogen, a bioluminescent substance, a chemiluminescent substance, or a semiconductor nanocrystal. More particularly, $R^a$ is avidin, streptavidin or an analog thereof.

In certain embodiments, $R^a$ is a solid support.

In certain embodiments, $R^a$ is a carrier molecule. More particularly, the carrier molecule is selected from the group consisting of an amino acid, a peptide, a protein, a carbohydrate, a polysaccharide, a nucleoside, a nucleotide, an oligonucleotide, a nucleic acid polymer, a drug, a lipid, and a synthetic polymer.

In certain embodiments, the compound of Formula (I) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, $R^a$ is:

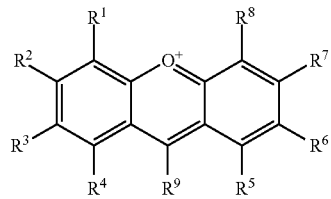

or a tautomer or salt thereof;

wherein, $R^1$, $R^2$, $R^3$, $R^4$, $R^5$, $R^6$, $R^7$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or one or more of $R^1$ and $R^2$, $R^2$ and $R^3$, $R^3$ and $R^4$, $R^5$ and $R^6$, $R^6$ and $R^7$ or $R^7$ and $R^8$ are taken together to form a fused aryl or heteroaryl group; and one of $R^1$, $R^2$, $R^3$, $R^4$, $R^5$, $R^6$, $R^7$, $R^8$ and $R^9$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

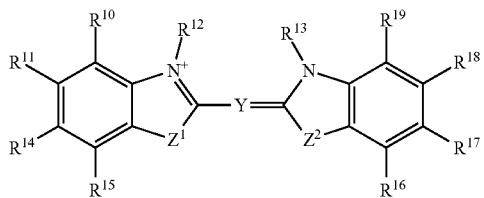

or a tautomer or salt thereof;
wherein,
$Z^1$ and $Z^2$ are each independently O, S, $NR^{23}$ or $CR^{24}R^{25}$;
Y is $-CR^{20}=(CR^{21}-CR^{22}=)_p$;
p is 0, 1, 2, or 3;
$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$, $R^{13}$ and $R^{23}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{20}$, $R^{21}$ and $R^{22}$ are each independently, H, alkyl, substituted alkyl, cycloalkyl, substituted cycloalkyl, aryl, substituted aryl, heteroaryl, or substituted heteroaryl;

$R^{24}$ and $R^{25}$ are H, alkyl or substituted alkyl; and
one of $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^3$, $R^{24}$ and $R^{25}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

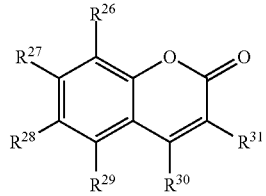

or a tautomer or salt thereof;
wherein,
$R^{26}$, $R^{27}$, $R^{28}$, $R^{29}$, $R^{30}$ and $R^{31}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{26}$, $R^{27}$, $R^{28}$, $R^{29}$, $R^{30}$ and $R^{31}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

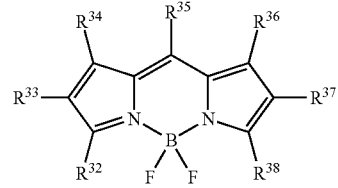

or a tautomer or salt thereof;
wherein,
$R^{32}$, $R^{33}$, $R^{34}$, $R^{35}$, $R^{36}$, $R^{37}$ and $R^{38}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{32}$, $R^{33}$, $R^{34}$, $R^{35}$, $R^{36}$, $R^{37}$ and $R^{38}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

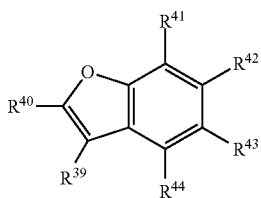

or a tautomer or salt thereof;
wherein, $R^{39}$, $R^{40}$, $R^{41}$, $R^{42}$, $R^{43}$ and $R^{44}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{39}$, $R^{40}$, $R^{41}$, $R^{42}$, $R^{43}$ and $R^{44}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

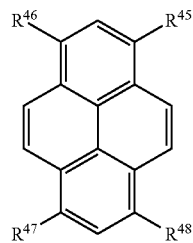

or a tautomer or salt thereof;
wherein, $R^{45}$, $R^{46}$, $R^{47}$, and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{45}$, $R^{46}$, $R^{47}$, and $R^{48}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

Certain embodiments provide a composition comprising:
(a) an analyte; and
(b) a compound of Formula (II) or a tautomer or salt thereof:

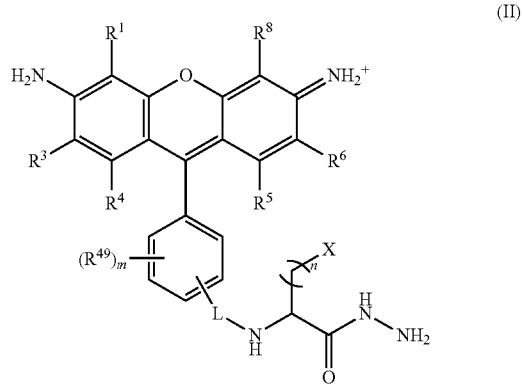

wherein,
L is a linker;
n is an integer from 1 to 24;
X is a molecule containing $SO_3H$, $SO_3^-$, $OPO_3^{2-}$, $OPO_3H_2$, $PO_3H_2$, $PO_3^{2-}$, COOH, or $COO^-$;
$R^1$, $R^3$, $R^4$, $R^5$, $R^6$, $R^8$ and $R^{49}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and m is 0, 1, or 2.

In certain embodiments, $R^1$ and $R^8$ are each sulfo; $R^2$, $R^3$, $R^4$, $R^5$, $R^6$, and $R^7$ are each H;

$R^{49}$ is carboxy; m is 1; L is —C═O; X is selected from $N[(CH_2)_3SO_3H]_2$, $SO_3H$, $SO_3^-$, $OPO_3^{2-}$, $OPO_3H_2$, $PO_3H_2$, $PO_3^{2-}$, COOH, and $COO^-$; and n is 1, 2, 3 or 4.

In certain embodiments, the compound of Formula (II) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

Certain embodiments provide a composition comprising:
(a) an analyte; and
(b) a compound of Formula (III) or a tautomer or salt thereof:

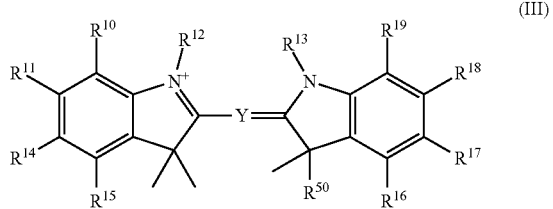

(III)

wherein,
Y is —CR$^{20}$=(CR$^{21}$—CR$^{22}$=)$_p$;
p is 0, 1, 2, or 3;
R$^{10}$, R$^{11}$, R$^{14}$, R$^{15}$, R$^{16}$, R$^{17}$, R$^{18}$ and R$^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;
R$^{12}$ and R$^{13}$ are each independently H, alkyl, substituted alkyl, cycloalkyl, substituted cycloalkyl, aryl, substituted aryl, heteroaryl, substituted heteroaryl, heterocyclyl, substituted heterocyclyl;
R$^{50}$ is alkyl; and
wherein one of R$^{13}$ or R$^{50}$ is:

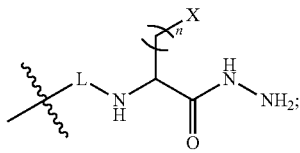

L is a linker;
n is an integer from 1 to 24; and
X is a molecule containing SO$_3$H, SO$_3^-$, OPO$_3^{2-}$, OPO$_3$H$_2$, PO$_3$H$_2$, PO$_3^{2-}$, COOH, or COO$^-$.

In certain embodiments, R$^{50}$ is methyl.

In certain embodiments, the compound of Formula (III) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

Certain embodiments provide a composition comprising:
(a) an analyte; and
(b) a compound of Formula (IV) or a tautomer or salt thereof:

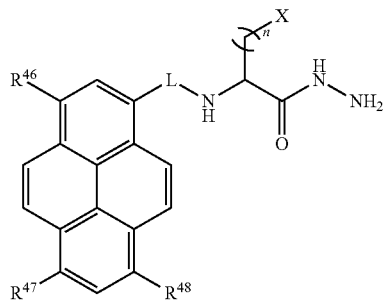

(IV)

wherein,
L is a linker;
n is an integer from 1 to 24;
X is a molecule containing SO$_3$H, SO$_3^-$, OPO$_3^{2-}$, OPO$_3$H$_2$, PO$_3$H$_2$, PO$_3^{2-}$, COOH, or COO$^-$; and
R$^{46}$, R$^{47}$ and R$^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl.

In certain embodiments, R$^{46}$, R$^{47}$, and R$^{48}$ are each sulfo; X is carboxy; n is 1 or 2; and L is

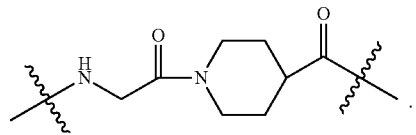 [SMILES: *NCC(=O)N1CCC(C(*)=O)CC1]

.

In certain embodiments, the compound of Formula (IV) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

Certain embodiments provide a composition comprising:
(a) an analyte; and
(b) a compound of Formula (V) or a tautomer or salt thereof:

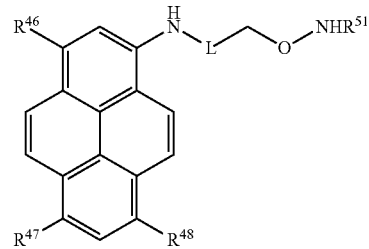

(V)

wherein,

L is a linker;

$R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^{51}$ is selected from H, alkyl and substituted alkyl.

In certain embodiments, $R^{46}$, $R^{47}$, and $R^{48}$ are each sulfo, $R^{51}$ is H, and L is selected from the group consisting of: —(CH$_2$)$_5$C(O)NH(CH$_2$)$_2$—, —(CH$_2$)$_6$NHC(O)— and —C(O)—.

In certain embodiments, the compound of Formula (V) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

Certain embodiments provide a composition comprising:

(a) an analyte; and (b) a compound selected from the group consisting of:

Compound 1

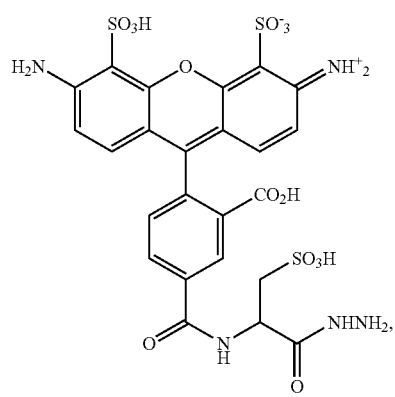

Compound 2

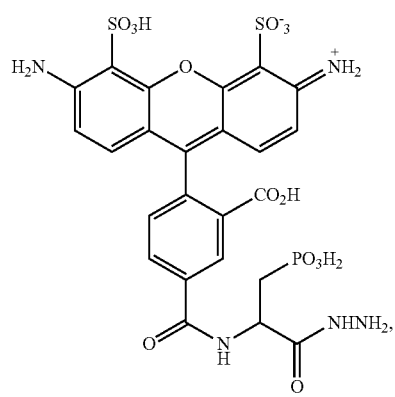

Compound 3

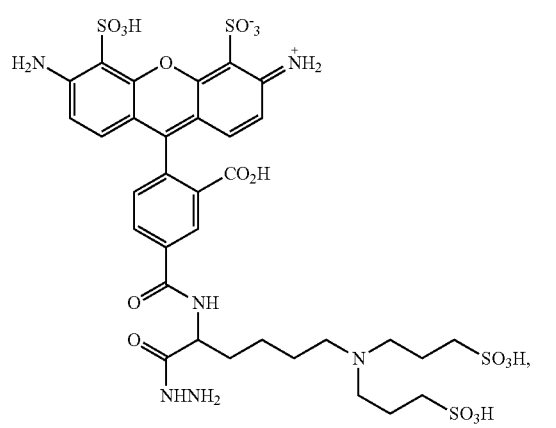

Compound 4

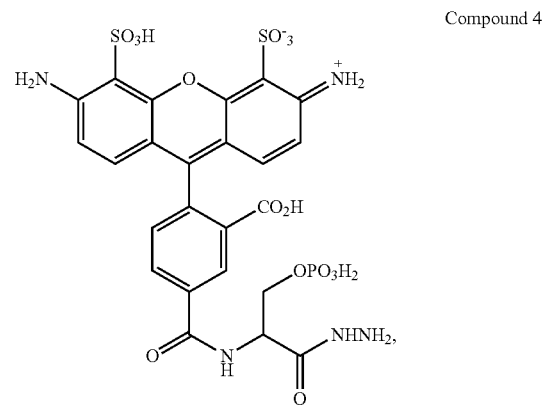

Compound 5

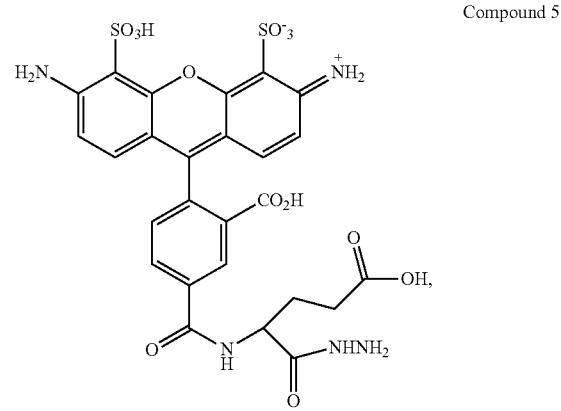

Compound 6

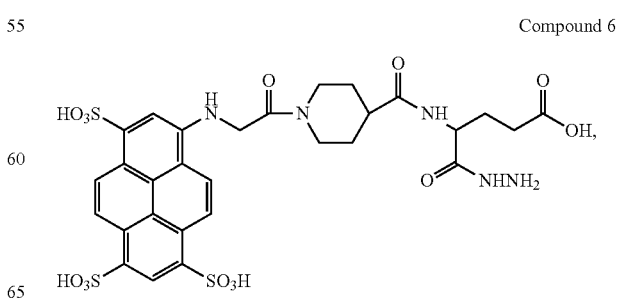

-continued

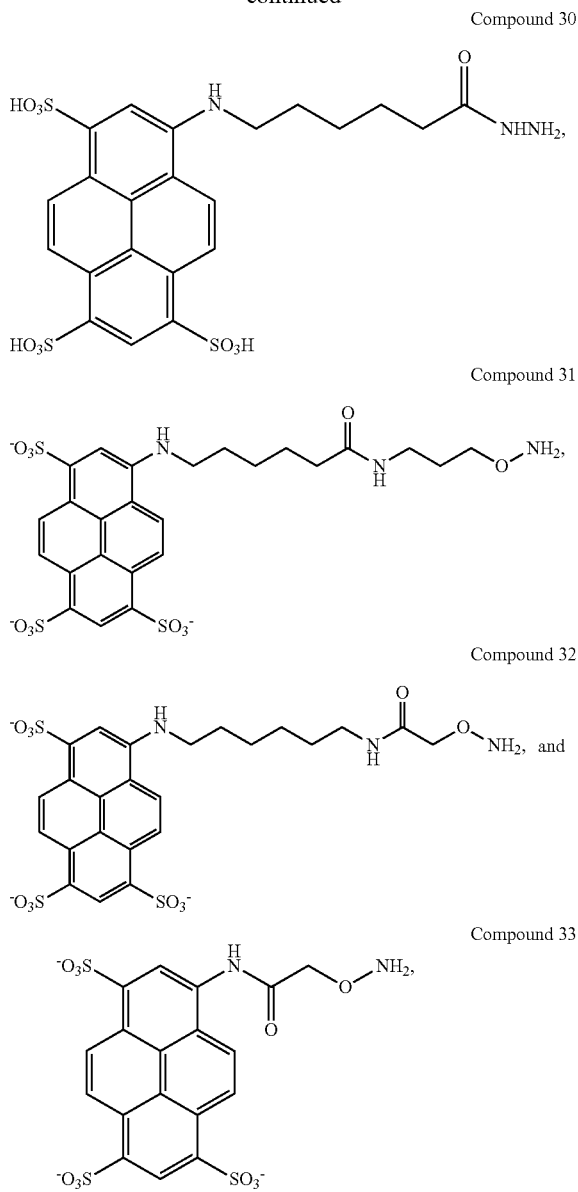

Compound 30

Compound 31

Compound 32

Compound 33 or a salt thereof.

In certain embodiments, the compound is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, the composition further comprises a buffer solution. In certain embodiments, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus.

In certain embodiments, a method for determining the presence of an analyte of interest in a sample is provided, the method comprising:

a) contacting the sample with a compound of the invention or a tautomer or salt thereof;

b) incubating the sample and the compound for a sufficient amount of time to form a complex between the compound and analyte;

c) illuminating the complex with an appropriate wavelength to form an illuminated complex; and d) detecting emissions from the illuminated complex, thereby determining the presence of the analyte in the sample.

In certain embodiments, a method for determining the presence of an analyte of interest in a sample is provided, the method comprising:

a) contacting the sample with a compound having Formula (I) or a tautomer or salt thereof:

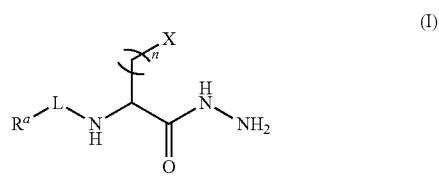

(I)

wherein,

L is a linker;

$R^a$ is a reporter molecule, carrier molecule or a solid support;

n is an integer from 1 to 24; and

X is a molecule containing $SO_3H$, $SO_3^-$, $OPO_3^{2-}$, $OPO_3H_2$, $PO_3H_2$, $PO_3^{2-}$, $COOH$, or $COO^-$;

b) incubating the sample and the compound for a sufficient amount of time to form a complex between the compound and analyte;

c) illuminating the complex with an appropriate wavelength to form an illuminated complex; and d) detecting emissions from the illuminated complex, thereby determining the presence of the analyte in the sample.

In certain embodiments, the analyte is a glycan. In certain embodiments, the glycan is cleaved from a biomolecule. In certain embodiments, the analyte and the compound are connected by a covalent bond. In certain embodiments, the analyte is bound to the compound through an imine. In certain embodiments, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. In certain embodiments, the analyte comprises an aldehyde. In certain embodiments, the analyte comprises a carbonyl group. More particularly, the analyte comprises a ketone group or an aldehyde group.

In certain embodiments, L is a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is a dye. More particularly, the dye is a pyrene, a xanthene, a cyanine, an indole, a benzofuran, a coumarin, or a borapolyazaindacine.

In certain embodiments, $R^a$ is a chelating moiety, a hapten, an antibody, an enzyme, a radiolabel, a metal ion or metal ion containing substance, a pigment, a chromogen, a phosphor, a fluorogen, a bioluminescent substance, a chemiluminescent substance, or a semiconductor nanocrystal. More particularly, $R^a$ is avidin, streptavidin or an analog thereof.

In certain embodiments, $R^a$ is a solid support.

In certain embodiments, $R^a$ is a carrier molecule. More particularly, the carrier molecule is selected from the group consisting of an amino acid, a peptide, a protein, a carbohydrate, a polysaccharide, a nucleoside, a nucleotide, an oligonucleotide, a nucleic acid polymer, a drug, a lipid, and a synthetic polymer.

In certain embodiments, the compound of Formula (I) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, $R^a$ is:

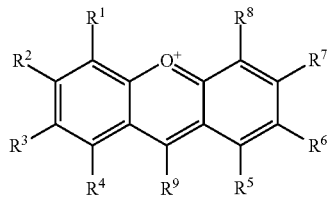

or a tautomer or salt thereof;
wherein,
$R^1$, $R^2$, $R^3$, $R^4$, $R^5$, $R^6$, $R^7$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or one or more of $R^1$ and $R^2$, $R^2$ and $R^3$, $R^3$ and $R^4$, $R^5$ and $R^6$, $R^6$ and $R^7$ or $R^7$ and $R^8$ are taken together to form a fused aryl or heteroaryl group; and
one of $R^1$, $R^2$, $R^3$, $R^4$, $R^5$, $R^6$, $R^7$, $R^8$ and $R^9$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

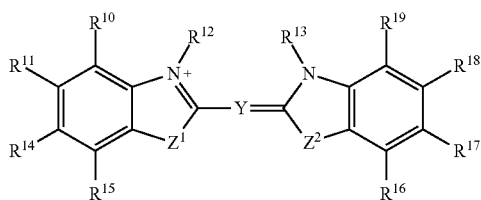

or a tautomer or salt thereof;
wherein,
$Z^1$ and $Z^2$ are each independently O, S, $NR^{23}$ or $CR^{24}R^{25}$;
Y is $-CR^{20}=(CR^{21}-CR^{22}=)_p$;
p is 0, 1, 2, or 3;
$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;
$R^{12}$, $R^{13}$ and $R^{23}$ are each independently H, alkyl, substituted alkyl, cycloalkyl, substituted cycloalkyl, aryl, substituted aryl, heteroaryl, substituted heteroaryl, heterocyclyl, substituted heterocyclyl;
$R^{20}$, $R^{21}$ and $R^{22}$ are each independently, H, alkyl, substituted alkyl, cycloalkyl, substituted cycloalkyl, aryl, substituted aryl, heteroaryl, or substituted heteroaryl;
$R^{24}$ and $R^{25}$ are H, alkyl or substituted alkyl; and
one of $R^{10}$, $R^{11}$, $R^{12}$, $R^3$, $R^{14}$, $R^{15}$, $R^{16}$, $R^{17}$, $R^{18}$, $R^{19}$, $R^{20}$, $R^{21}$, $R^{22}$, $R^3$, $R^{24}$ and $R^{25}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

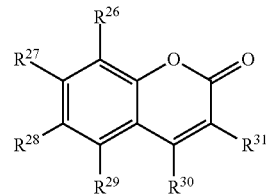

or a tautomer or salt thereof;
wherein,
$R^{26}$, $R^{27}$, $R^{28}$, $R^{29}$, $R^{30}$ and $R^{31}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
one of $R^{26}$, $R^{27}$, $R^{28}$, $R^{29}$, $R^{30}$ and $R^{31}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

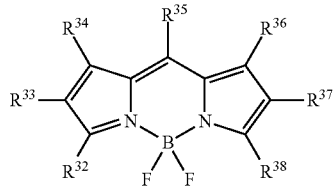

or a tautomer or salt thereof;
wherein,
$R^{32}$, $R^{33}$, $R^{34}$, $R^{35}$, $R^{36}$, $R^{37}$ and $R^{38}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{32}$, $R^{33}$, $R^{34}$, $R^{35}$, $R^{36}$, $R^{37}$ and $R^{38}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

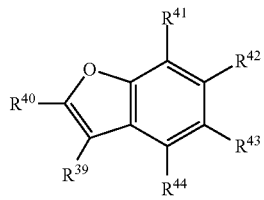

or a tautomer or salt thereof;
wherein,
$R^{39}$, $R^{40}$, $R^{41}$, $R^{42}$, $R^{43}$ and $R^{44}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{39}$, $R^{40}$, $R^{41}$, $R^{42}$, $R^{43}$ and $R^{44}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

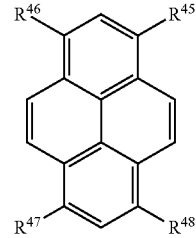

or a tautomer or salt thereof;
wherein,
$R^{45}$, $R^{46}$, $R^{47}$, and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{45}$, $R^{46}$, $R^{47}$, and $R^{48}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, a method for determining the presence of an analyte of interest in a sample is provided, the method comprising:
a) contacting the sample with a compound having Formula (II) or a tautomer or salt thereof:

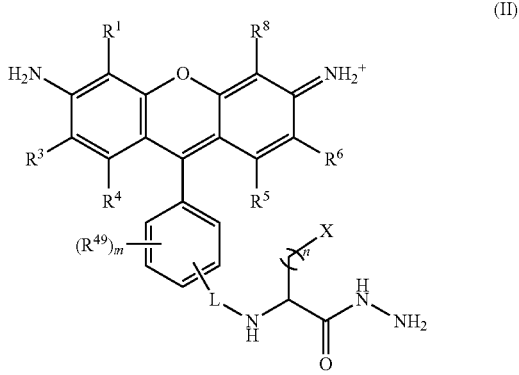

(II)

wherein,
L is a linker;
n is an integer from 1 to 24;

X is a molecule containing $SO_3H$, $SO_3^-$, $OPO_3^{2-}$, $OPO_3H_2$, $PO_3H_2$, $PO_3^{2-}$, COOH, or $COO^-$;

$R^1$, $R^3$, $R^4$, $R^5$, $R^6$, $R^8$ and $R^{49}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and m is 0, 1, or 2;

b) incubating the sample and the compound for a sufficient amount of time to form a complex between the compound and analyte;

c) illuminating the complex with an appropriate wavelength to form an illuminated complex; and d) detecting emissions from the illuminated complex, thereby determining the presence of the analyte in the sample.

In certain embodiments, the analyte is a glycan. In certain embodiments, the glycan is cleaved from a biomolecule. In certain embodiments, the analyte and the compound are connected by a covalent bond. In certain embodiments, the analyte is bound to the compound through an imine. In certain embodiments, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. In certain embodiments, the analyte comprises an aldehyde. In certain embodiments, the analyte comprises a carbonyl group. More particularly, the analyte comprises a ketone group or an aldehyde group.

In certain embodiments, $R^1$ and $R^8$ are each sulfo; $R^2$, $R^3$, $R^4$, $R^5$, $R^6$, and $R^7$ are each H; $R^{49}$ is carboxy; m is 1; L is —C═O; X is selected from $N[(CH_2)_3SO_3H]_2$, $SO_3H$, $SO_3^-$, $OPO_3^{2-}$, $OPO_3H_2$, $PO_3H_2$, $PO_3^{2-}$, COOH, and $COO^-$; and n is 1, 2, 3 or 4.

In certain embodiments, the compound of Formula (II) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a method for determining the presence of an analyte of interest in a sample is provided, the method comprising:

a) contacting the sample with a compound having Formula (III) or a tautomer or salt thereof:

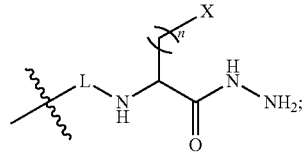

(III)

wherein,

Y is $-CR^{20}=(CR^{21}-CR^{22}=)_p$;

p is 0, 1, 2, or 3;

$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$ and $R^{13}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{50}$ is alkyl; and wherein one of $R^{13}$ or $R^{50}$ is:

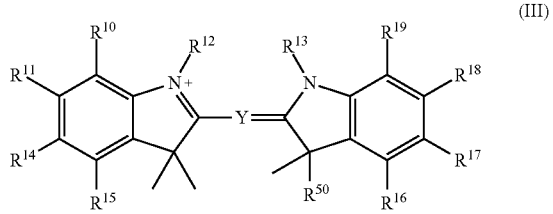

L is a linker;

n is an integer from 1 to 24; and

X is a molecule containing $SO_3H$, $SO_3^-$, $OPO_3^{2-}$, $OPO_3H_2$, $PO_3H_2$, $PO_3^{2-}$, COOH, or $COO^-$;

b) incubating the sample and the compound for a sufficient amount of time to form a complex between the compound and analyte;

c) illuminating the complex with an appropriate wavelength to form an illuminated complex; and d) detecting emissions from the illuminated complex, thereby determining the presence of the analyte in the sample.

In certain embodiments, the analyte is a glycan. In certain embodiments, the glycan is cleaved from a biomolecule. In certain embodiments, the analyte and the compound are connected by a covalent bond. In certain embodiments, the analyte is bound to the compound through an imine. In certain embodiments, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. In certain embodiments, the analyte comprises an aldehyde. In certain embodiments, the analyte comprises a carbonyl group. More particularly, the analyte comprises a ketone group or an aldehyde group.

In certain embodiments, $R^{50}$ is methyl.

In certain embodiments, the compound of Formula (III) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a method for determining the presence of an analyte of interest in a sample is provided, the method comprising:

a) contacting the sample with a compound having Formula (IV) or a tautomer or salt thereof:

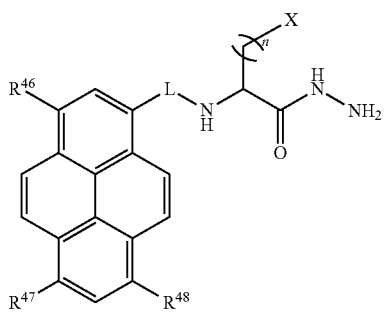

(IV)

wherein,
L is a linker;
n is an integer from 1 to 24;
X is a molecule containing $SO_3H$, $SO_3^-$, $OPO_3^{2-}$, $OPO_3H_2$, $PO_3H_2$, $PO_3^{2-}$, COOH, or $COO^-$; and
$R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

b) incubating the sample and the compound for a sufficient amount of time to form a complex between the compound and analyte;
c) illuminating the complex with an appropriate wavelength to form an illuminated complex; and
d) detecting emissions from the illuminated complex, thereby determining the presence of the analyte in the sample.

In certain embodiments, the analyte is a glycan. In certain embodiments, the glycan is cleaved from a biomolecule. In certain embodiments, the analyte and the compound are connected by a covalent bond. In certain embodiments, the analyte is bound to the compound through an imine. In certain embodiments, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. In certain embodiments, the analyte comprises an aldehyde. In certain embodiments, the analyte comprises a carbonyl group. More particularly, the analyte comprises a ketone group or an aldehyde group.

In certain embodiments, $R^{46}$, $R^{47}$, and $R^{48}$ are each sulfo; X is carboxy; n is 1 or 2; and L is

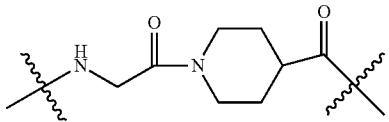

.

In certain embodiments, the compound of Formula (IV) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a method for determining the presence of an analyte of interest in a sample is provided, the method comprising:

a) contacting the sample with a compound having Formula (V) or a tautomer or salt thereof:

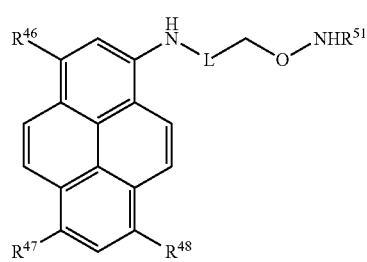

(V)

wherein,
L is a linker;
$R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
$R^{51}$ is selected from H, alkyl and substituted alkyl;

b) incubating the sample and the compound for a sufficient amount of time to form a complex between the compound and analyte;
c) illuminating the complex with an appropriate wavelength to form an illuminated complex; and
d) detecting emissions from the illuminated complex, thereby determining the presence of the analyte in the sample.

In certain embodiments, the analyte is a glycan. In certain embodiments, the glycan is cleaved from a biomolecule. In certain embodiments, the analyte and the compound are connected by a covalent bond. In certain embodiments, the analyte is bound to the compound through an oxime. In certain embodiments, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. In certain embodiments, the analyte comprises an aldehyde. In certain embodiments, the analyte comprises a carbonyl group. More particularly, the analyte comprises a ketone group or an aldehyde group.

In certain embodiments, $R^{46}$, $R^{47}$, and $R^{48}$ are each sulfo, $R^{51}$ is H, and L is selected from the group consisting of: —$(CH_2)_5C(O)NH(CH_2)_2$—, —$(CH_2)_6NHC(O)$— and —$C(O)$—.

In certain embodiments, the compound of Formula (V) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a method for determining the presence of an analyte of interest in a sample is provided, the method comprising:

a) contacting the sample with a compound selected from the group consisting of:

Compound 1
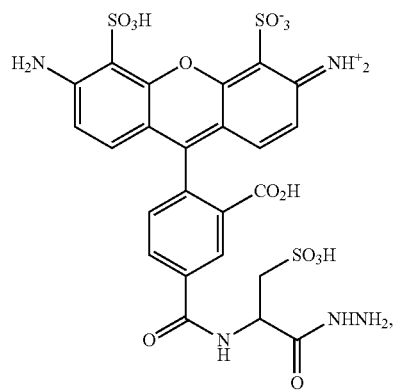

Compound 2
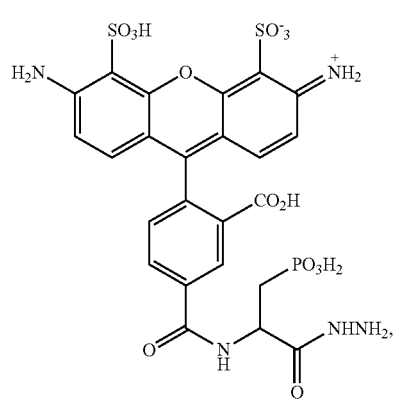

Compound 3
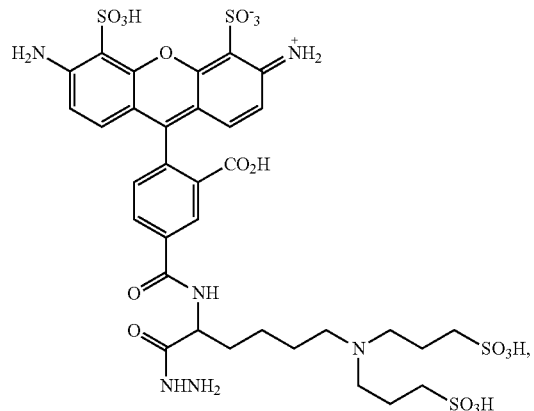

Compound 4
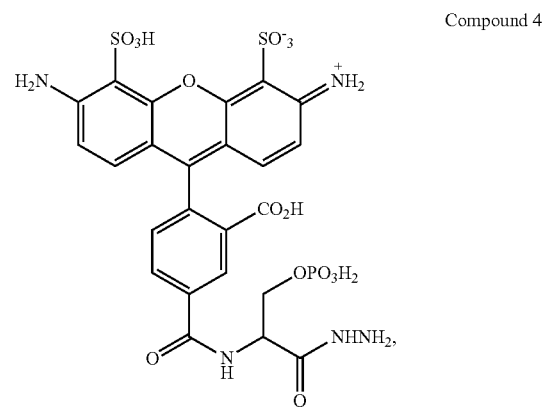

Compound 5
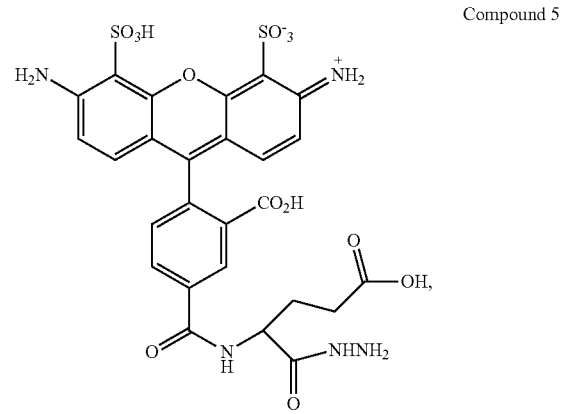

Compound 6
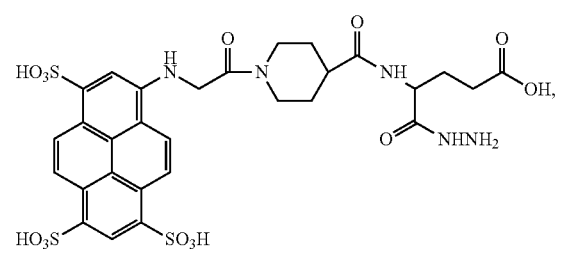

-continued

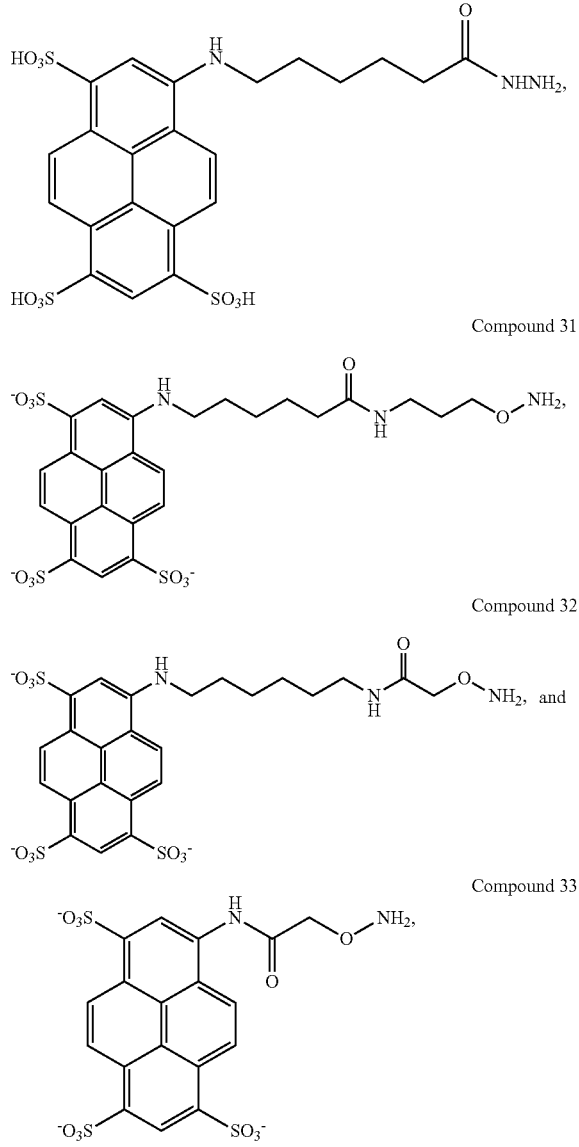

Compound 30

Compound 31

Compound 32

Compound 33 or a salt thereof;
b) incubating the sample and the compound for a sufficient amount of time to form a complex between the compound and analyte;
c) illuminating the complex with an appropriate wavelength to form an illuminated complex; and
d) detecting emissions from the illuminated complex, thereby determining the presence of the analyte in the sample.

In certain embodiments, the analyte is a glycan. In certain embodiments, the glycan is cleaved from a biomolecule. In certain embodiments, the analyte and the compound are connected by a covalent bond. In certain embodiments, the analyte is bound to the compound through an imine or an oxime. In certain embodiments, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. More particularly, the analyte comprises a ketone group or an aldehyde group.

In certain embodiments, the compound is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, the sample comprises live cells, intracellular fluids, extracellular fluids, biological fluids, biological fermentation media, environmental sample, industrial samples, proteins, peptides, buffer solutions biological fluids or chemical reactors. More particularly, the sample comprises blood cells, immune cells, cultured cells, muscle tissue, neurons, extracellular vesicles; vascular tissue, blood fluids, saliva, urine; water, soil, waste water, sea water; pharmaceuticals, foodstuffs or beverages. In certain embodiments, the sample is immobilized on a polymeric membrane, within a polymeric gel, on a microparticle, on a microarray, on a silicon chip, on a glass slide, on a microwell plate, and on a microfluidic chip.

In certain embodiments, a method for determining the presence of one or more glycans in a sample is provided, the method comprising:
a) contacting the sample with a compound of the invention or a tautomer or salt thereof;
b) incubating the sample and the compound for a sufficient amount of time to form a complex between the compound and the one or more glycans;
c) separating the sample using electrophoresis or chromatography, thereby determining the presence of the one or more glycans in the sample.

In certain embodiments, the glycan and the compound are connected by a covalent bond.

In certain embodiments, a method for determining the presence of one or more glycans in a sample is provided, the method comprising:
a) contacting the sample with a compound having Formula (I) or a tautomer or salt thereof:

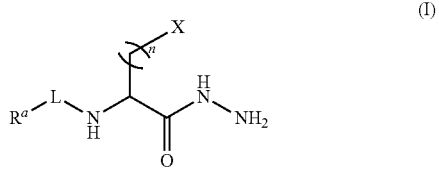

(I)

wherein,
L is a linker;
$R^a$ is a reporter molecule, carrier molecule or a solid support;
n is an integer from 1 to 24; and
X is a molecule containing $SO_3H$, $SO_3^-$, $OPO_3^{2-}$, $OPO_3H_2$, $PO_3H_2$, $PO_3^{2-}$, $COOH$, or $COO^-$;
b) incubating the sample and the compound for a sufficient amount of time to form a complex between the compound and the one or more glycans;
c) separating the sample using electrophoresis or chromatography, thereby determining the presence of the one or more glycans in the sample.

In certain embodiments, the glycan and the compound are connected by a covalent bond.

In certain embodiments, L is a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is a dye. More particularly, the dye is a pyrene, a xanthene, a cyanine, an indole, a benzofuran, a coumarin, or a borapolyazaindacine.

In certain embodiments, $R^a$ is a chelating moiety, a hapten, an antibody, an enzyme, a radiolabel, a metal ion or metal ion containing substance, a pigment, a chromogen, a phosphor, a fluorogen, a bioluminescent substance, a chemiluminescent substance, or a semiconductor nanocrystal. More particularly, $R^a$ is avidin, streptavidin or an analog thereof.

In certain embodiments, $R^a$ is a solid support.

In certain embodiments, $R^a$ is a carrier molecule. More particularly, the carrier molecule is selected from the group consisting of an amino acid, a peptide, a protein, a carbohydrate, a polysaccharide, a nucleoside, a nucleotide, an oligonucleotide, a nucleic acid polymer, a drug, a lipid, and a synthetic polymer.

In certain embodiments, the compound of Formula (I) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, $R^a$ is:

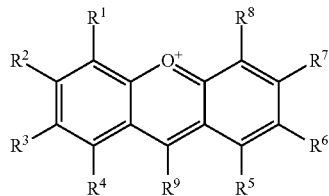

or a tautomer or salt thereof;
wherein,
$R^1$, $R^2$, $R^3$, $R^4$, $R^5$, $R^6$, $R^7$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or one or more of $R^1$ and $R^2$, $R^2$ and $R^3$, $R^3$ and $R^4$, $R^5$ and $R^6$, $R^6$ and $R^7$ or $R^7$ and $R^8$ are taken together to form a fused aryl or heteroaryl group; and one of $R^1$, $R^2$, $R^3$, $R^4$, $R^5$, $R^6$, $R^7$, $R^8$ and $R^9$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

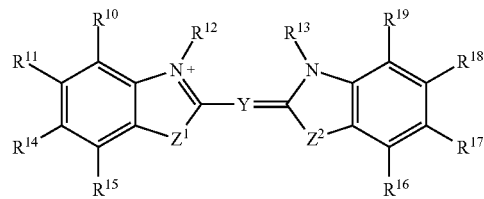

or a tautomer or salt thereof;
wherein,
$Z^1$ and $Z^2$ are each independently O, S, $NR^{23}$ or $CR^{24}R^{25}$;
Y is $-CR^{20}=(CR^{21}-CR^{22}=)_p$;
p is 0, 1, 2, or 3;
$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$, $R^{13}$ and $R^{23}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{20}$, $R^{21}$ and $R^{22}$ are each independently, H, alkyl, substituted alkyl, cycloalkyl, substituted cycloalkyl, aryl, substituted aryl, heteroaryl, or substituted heteroaryl;

$R^{24}$ and $R^{25}$ are H, alkyl or substituted alkyl; and
one of $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

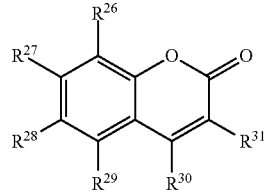

or a tautomer or salt thereof;
wherein,
$R^{26}$, $R^{27}$, $R^{28}$, $R^{29}$, $R^{30}$ and $R^{31}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{26}$, $R^{27}$, $R^{28}$, $R^{29}$, $R^{30}$ and $R^{31}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments $R^a$ is:

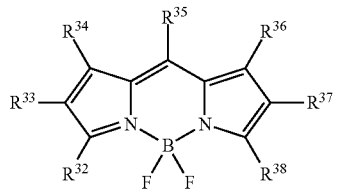

or a tautomer or salt thereof;
wherein,
$R^{32}$, $R^{33}$, $R^{34}$, $R^{35}$, $R^{36}$, $R^{37}$ and $R^{38}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{32}$, $R^{33}$, $R^{34}$, $R^{35}$, $R^{36}$, $R^{37}$ and $R^{38}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

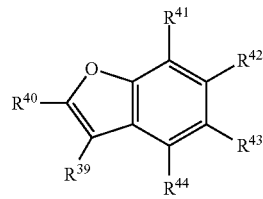

or a tautomer or salt thereof;
wherein,
$R^{39}$, $R^{40}$, $R^{41}$, $R^{42}$, $R^{43}$ and $R^{44}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{39}$, $R^{40}$, $R^{41}$, $R^{42}$, $R^{43}$ and $R^{44}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

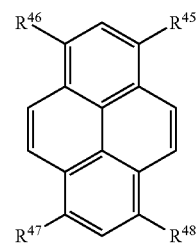

or a tautomer or salt thereof;
wherein,
$R^{45}$, $R^{46}$, $R^{47}$, and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{45}$, $R^{46}$, $R^{47}$, and $R^{48}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, a method for determining the presence of one or more glycans in a sample is provided, the method comprising:

a) contacting the sample with a compound having Formula (II) or a tautomer or salt thereof:

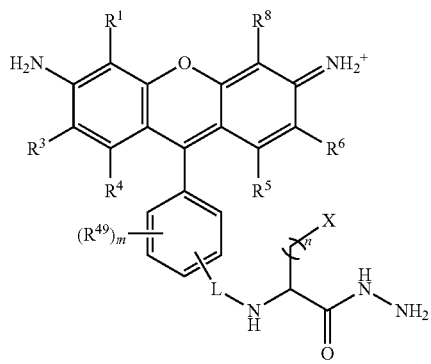

(II)

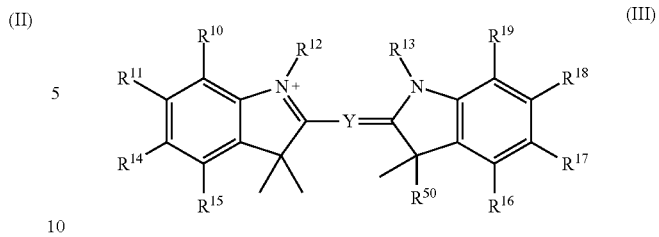

(III)

wherein,

L is a linker;

n is an integer from 1 to 24;

X is a molecule containing $SO_3H$, $SO_3^-$, $OPO_3^{2-}$, $OPO_3H_2$, $PO_3H_2$, $PO_3^{2-}$, COOH, or $COO^-$;

$R^1$, $R^3$, $R^4$, $R^5$, $R^6$, $R^8$ and $R^{49}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and m is 0, 1, or 2;

b) incubating the sample and the compound for a sufficient amount of time to form a complex between the compound and the one or more glycans;

c) separating the sample using electrophoresis or chromatography, thereby determining the presence of the one or more glycans in the sample.

In certain embodiments, the glycan and the compound are connected by a covalent bond.

In certain embodiments, $R^1$ and $R^8$ are each sulfo; $R^2$, $R^3$, $R^4$, $R^5$, $R^6$, and $R^7$ are each H; $R^{49}$ is carboxy; m is 1; L is —C═O; X is selected from $N[(CH_2)_3SO_3H]_2$, $SO_3H$, $SO_3^-$, $OPO_3^{2-}$, $OPO_3H_2$, $PO_3H_2$, $PO_3^{2-}$, COOH, and $COO^-$; and n is 1, 2, 3 or 4.

In certain embodiments, the compound of Formula (II) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a method for determining the presence of one or more glycans in a sample is provided, the method comprising:

a) contacting the sample with a compound having Formula (III) or a tautomer or salt thereof:

wherein,

Y is $—CR^{20}═(CR^{21}—CR^{22}═)_p$;

p is 0, 1, 2, or 3;

$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$ and $R^{13}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{50}$ is alkyl; and wherein one of $R^{13}$ or $R^{50}$ is:

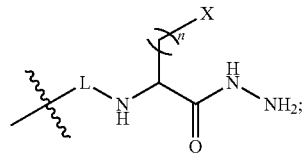

L is a linker;

n is an integer from 1 to 24; and

X is a molecule containing $SO_3H$, $SO_3^-$, $OPO_3^{2-}$, $OPO_3H_2$, $PO_3H_2$, $PO_3^{2-}$, COOH, or $COO^-$;

b) incubating the sample and the compound for a sufficient amount of time to form a complex between the compound and the one or more glycans;

c) separating the sample using electrophoresis or chromatography, thereby determining the presence of the one or more glycans in the sample.

In certain embodiments, the glycan and the compound are connected by a covalent bond.

In certain embodiments, $R^{50}$ is methyl.

In certain embodiments, the compound of Formula (III) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a method for determining the presence of one or more glycans in a sample is provided, the method comprising:

a) contacting the sample with a compound having Formula (IV) or a tautomer or salt thereof:

(IV)

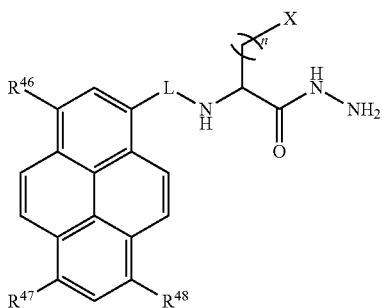

wherein,

L is a linker;

n is an integer from 1 to 24;

X is a molecule containing $SO_3H$, $SO_3^-$, $OPO_3^{2-}$, $OPO_3H_2$, $PO_3H_2$, $PO_3^{2-}$, COOH, or $COO^-$; and $R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

b) incubating the sample and the compound for a sufficient amount of time to form a complex between the compound and the one or more glycans;

c) separating the sample using electrophoresis or chromatography, thereby determining the presence of the one or more glycans in the sample.

In certain embodiments, the glycan and the compound are connected by a covalent bond.

In certain embodiments, $R^{46}$, $R^{47}$, and $R^{48}$ are each sulfo; X is carboxy; n is 1 or 2; and L is

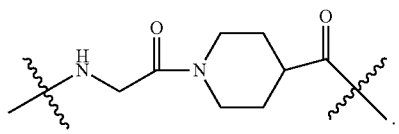

In certain embodiments, the compound of Formula (IV) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a method for determining the presence of one or more glycans in a sample is provided, the method comprising:

a) contacting the sample with a compound having Formula (V) or a tautomer or salt thereof:

(V)

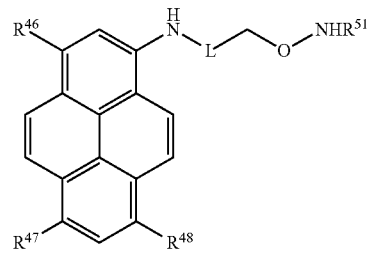

wherein,

L is a linker;

$R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^{51}$ is selected from H, alkyl and substituted alkyl;

b) incubating the sample and the compound for a sufficient amount of time to form a complex between the compound and the one or more glycans;

c) separating the sample using electrophoresis or chromatography, thereby determining the presence of the one or more glycans in the sample.

In certain embodiments, the glycan and the compound are connected by a covalent bond.

In certain embodiments, $R^{46}$, $R^{47}$, and $R^{48}$ are each sulfo, $R^{51}$ is H, and L is selected from the group consisting of: $-(CH_2)_5C(O)NH(CH_2)_2-$, $-(CH_2)_6NHC(O)-$ and $-C(O)-$.

In certain embodiments, the compound of Formula (V) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a method for determining the presence of one or more glycans in a sample is provided, the method comprising:

a) contacting the sample with a compound selected from the group consisting of:

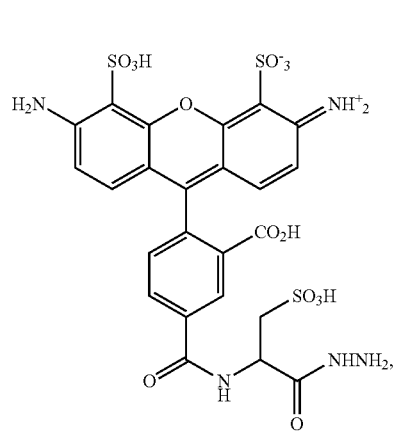

Compound 1

Compound 2
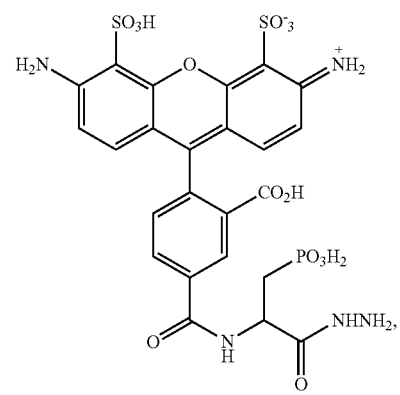

Compound 3
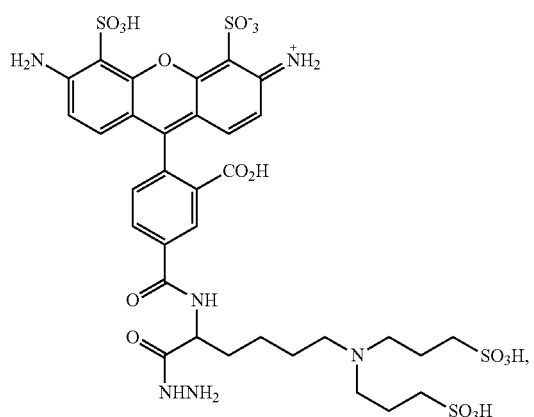

Compound 4
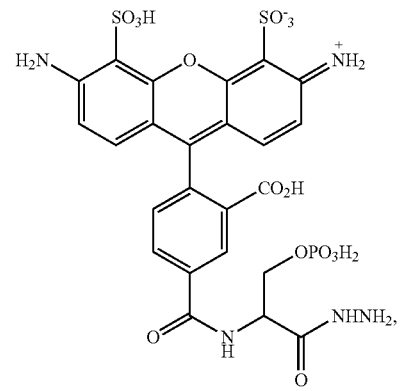

Compound 5
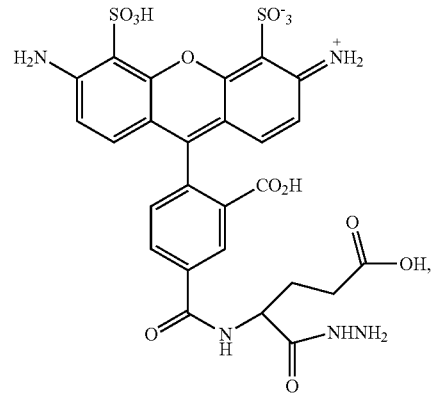

Compound 6
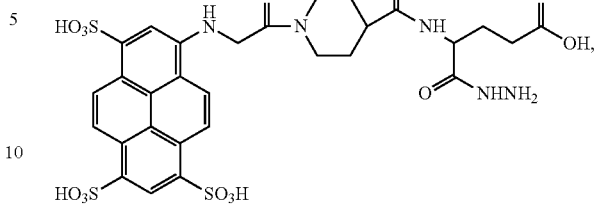

Compound 30
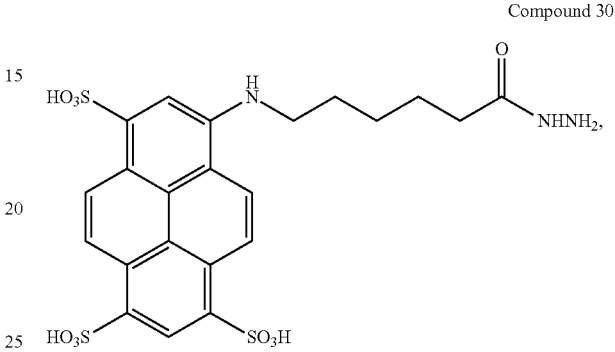

Compound 31
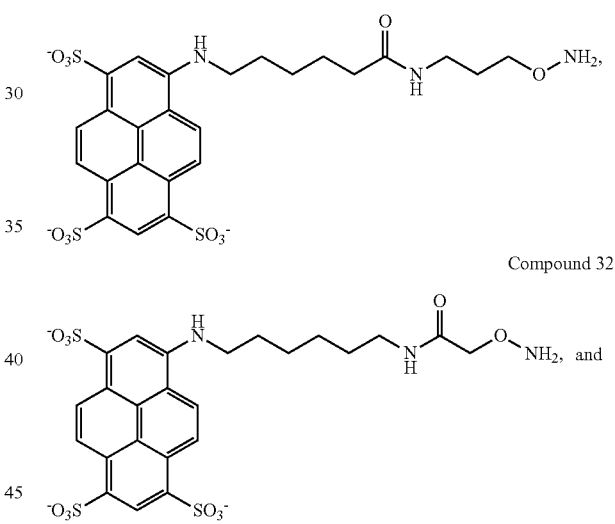

Compound 32

Compound 33
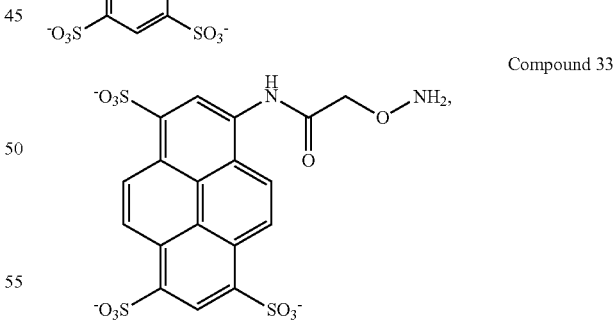

or a salt thereof;
b) incubating the sample and the compound for a sufficient amount of time to form a complex between the compound and the one or more glycans;
c) separating the sample using electrophoresis or chromatography, thereby determining the presence of the one or more glycans in the sample.

In certain embodiments, the compound is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, the glycan and the compound are connected by a covalent bond.

In certain embodiments, the method is performed using electrophoresis. In certain embodiments, the method is performed using capillary electrophoresis (CE). In certain embodiments, the method is performed using a glycan analysis system (see, co-owned, co-pending U.S. Provisional Patent Application Ser. No. 62/087,208, titled "Charged Reactive Oligomers" and PCT Patent Application No. PCT/US2015/063791 titled "Charged Reactive Oligomers, each of which is herein incorporated by reference in its entirety).

In certain embodiments, the method is performed using chromatography. In certain embodiments, the method is performed using high-performance liquid chromatography (HPLC) or liquid chromatography-mass spectroscopy (LC-MS).

In certain embodiments, the sample contains one or more glycans that can be the same or different. In certain embodiments, the method can be performed on one or more samples that each contains one or more glycans. In certain embodiments, each of the samples can be incubated with a different dye compound provided herein to allow for multiplexing (see, co-owned, co-pending U.S. Provisional Patent Application Ser. No. 62/087,208, titled "Charged Reactive Oligomers" and PCT Patent Application No. PCT/US2015/063791 titled "Charged Reactive Oligomers, each of which is herein incorporated by reference in its entirety).

In certain embodiments, dyes other than the hydrazinyl dye compounds and aminooxy dye compounds provided herein may be used in the methods described herein. In certain embodiments, the dye may be a visible dye, a fluorescent dye, or a chemiluminescent dye. In various embodiments, the fluorescent dye may be a pyrene dye, a naphthalene dye, an aminopyridine dye, a xanthene dye which may be a fluorescein, rhodol or rhodamine dye, a cyanine dye, a coumarin dye, a borapolyazaindacine dye, a benzofuran dye, or an indole dye. In some embodiments, the fluorescent dye may be aminopyrene trisulfonic acid (APTS). In certain embodiments, the APTS dye may be selected from those described in co-owned, co-pending U.S. Provisional Patent Application Ser. No. 62/087,208, titled "Charged Reactive Oligomers" and PCT Patent Application No. PCT/US2015/063791 titled "Charged Reactive Oligomers, each of which is herein incorporated by reference in its entirety, including, but not

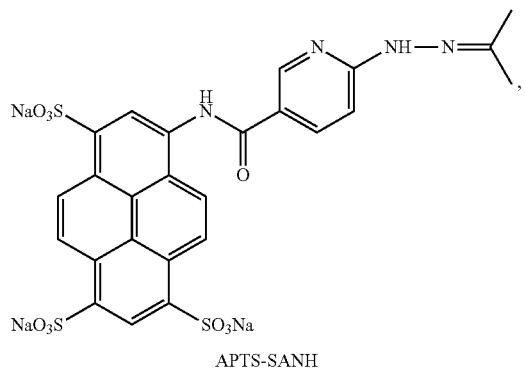

APTS-SANH

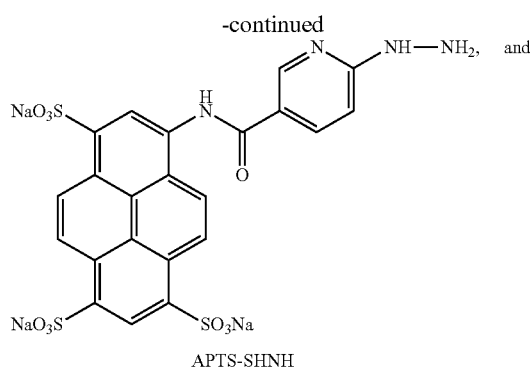

APTS-SHNH

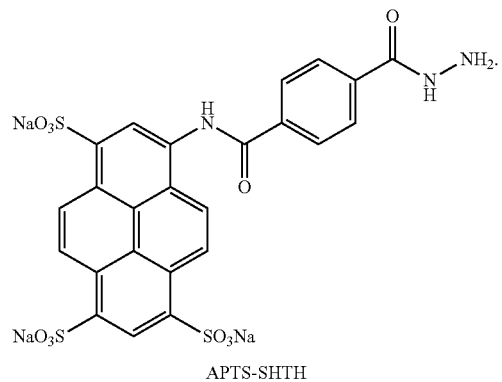

APTS-SHTH

In other embodiments, the fluorescent dye may be a fluorescein dye or a rhodamine dye. In various embodiments, more than one dye may be incorporated in the labeling species. When more than one dye may be incorporated in the labeling species, the fluorescent dye may be a polymeric dye or an energy transfer dye. An energy transfer dye may have a donor dye and an acceptor dye, where the donor dye may be configured to absorb energy at one wavelength and emit energy at a second wavelength which emitted energy excites the acceptor dye at the second wavelength. The acceptor dye then emits at a third wavelength, which may be detectable. If more than one labeling species may be used in a glycan detection assay where more than one energy transfer dye may be used to label various different glycans, then the more than one energy transfer dye are configured to be detected at different wavelengths, and therefore are spectrally resolvable.

In other embodiments, the energy transfer dye may be attached to the linker at the same point of attachment, i.e. may be attached at one atom of the labeling species. In other embodiments, the energy transfer dye may be attached to different atoms in the labeling species, while still being configured to donate and accept excitation energy for energy transfer dye performance.

In other embodiments, the labeling species may be labeled with a quencher dye which may be configured to quench fluorescence of a fluorescent dye. In yet other embodiments, the labeling species may contain a fluorescent dye and a quencher dye.

In certain embodiments, the dye includes, but is not limited to Cascade Blue, FAM™, JOE™, VIC™, HEX™, TET™, NED™, PET®, TAMRA™, ROX™, R110, R6G, Texas Red®, aminopyrene trisulfonic acid (APTS), NBD, BigDye™, 2-AA (anthranilic acid), 2-AB (2-aminobenzamide), aminoxyTMT™ mass tag labeling reagents (available from Thermo Scientific), or a tautomer or salt thereof, or a combination thereof.

In certain embodiments, a kit is provided for detecting an analyte in a sample, wherein the kit comprises:

a) a compound of the invention or a tautomer or salt thereof; and b) instructions for detecting the analyte according to one or more methods described herein.

In certain embodiments, a kit is provided for detecting an analyte in a sample, wherein the kit comprises:

a) a compound of Formula (I) or a tautomer or salt thereof:

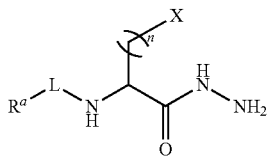
(I)

wherein,

L is a linker;

$R^a$ is a reporter molecule, carrier molecule or a solid support;

n is an integer from 1 to 24; and

X is a molecule containing $SO_3H$, $SO_3^-$, $OPO_3^{2-}$, $OPO_3H_2$, $PO_3H_2$, $PO_3^{2-}$, COOH, or $COO^-$; and b) instructions for detecting the analyte according to one or more methods described herein.

In certain embodiments, L is a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is a dye. More particularly, the dye is a pyrene, a xanthene, a cyanine, an indole, a benzofuran, a coumarin, or a borapolyazaindacene.

In certain embodiments, $R^a$ is a chelating moiety, a hapten, an antibody, an enzyme, a radiolabel, a metal ion or metal ion containing substance, a pigment, a chromogen, a phosphor, a fluorogen, a bioluminescent substance, a chemiluminescent substance, or a semiconductor nanocrystal. More particularly, $R^a$ is avidin, streptavidin or an analog thereof.

In certain embodiments, $R^a$ is a solid support.

In certain embodiments, $R^a$ is a carrier molecule. More particularly, the carrier molecule is selected from the group consisting of an amino acid, a peptide, a protein, a carbohydrate, a polysaccharide, a nucleoside, a nucleotide, an oligonucleotide, a nucleic acid polymer, a drug, a lipid, and a synthetic polymer.

In certain embodiments, the compound of Formula (I) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, $R^a$ is:

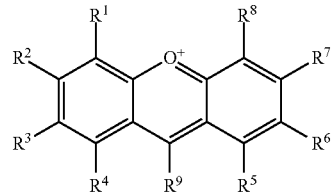

or a tautomer or salt thereof;

wherein, $R^1$, $R^2$, $R^3$, $R^4$, $R^5$, $R^6$, $R^7$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or one or more of $R^1$ and $R^2$, $R^2$ and $R^3$, $R^3$ and $R^4$, $R^5$ and $R^6$, $R^6$ and $R^7$ or $R^7$ and $R^8$ are taken together to form a fused aryl or heteroaryl group; and one of $R^1$, $R^2$, $R^3$, $R^4$, $R^5$, $R^6$, $R^7$, $R^8$ and $R^9$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

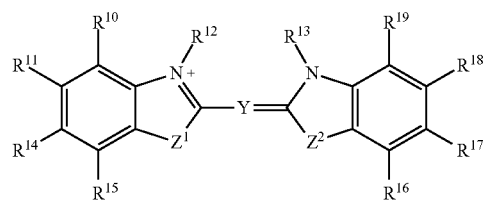

or a tautomer or salt thereof;

wherein, $Z^1$ and $Z^2$ are each independently O, S, $NR^{23}$ or $CR^{24}R^{25}$;

Y is $—CR^{20}=(CR^{21}—CR^{22}=)_p$;

p is 0, 1, 2, or 3;

$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$, $R^{13}$ and $R^{23}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{20}$, $R^{21}$ and $R^{22}$ are each independently, H, alkyl, substituted alkyl, cycloalkyl, substituted cycloalkyl, aryl, substituted aryl, heteroaryl, or substituted heteroaryl;

$R^{24}$ and $R^{25}$ are H, alkyl or substituted alkyl; and one of $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

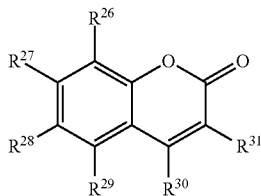

or a tautomer or salt thereof;
wherein, $R^{26}$, $R^{27}$, $R^{28}$, $R^{29}$, $R^{30}$ and $R^{31}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{26}$, $R^{27}$, $R^2$, $R^{29}$, $R^{30}$ and $R^{31}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

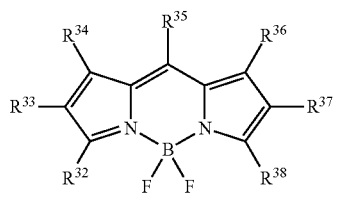

or a tautomer or salt thereof;
wherein, $R^{32}$, $R^{33}$, $R^{34}$, $R^{35}$, $R^{36}$, $R^{37}$ and $R^{38}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{32}$, $R^{33}$, $R^{34}$, $R^{35}$, $R^{36}$, $R^{37}$ and $R^{38}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

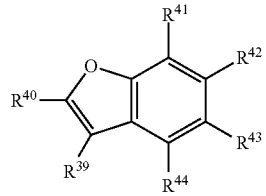

or a tautomer or salt thereof;
wherein, $R^{39}$, $R^{40}$, $R^{41}$, $R^{42}$, $R^{43}$ and $R^{44}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{39}$, $R^{40}$, $R^{41}$, $R^{42}$, $R^{43}$ and $R^{44}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

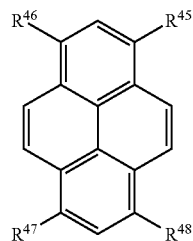

or a tautomer or salt thereof;
wherein,
$R^{45}$, $R^{46}$, $R^{47}$, and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{45}$, $R^{46}$, $R^{47}$, and $R^{48}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, a kit is provided for detecting an analyte in a sample, wherein the kit comprises:
a) a compound of Formula (II) or a tautomer or salt thereof:

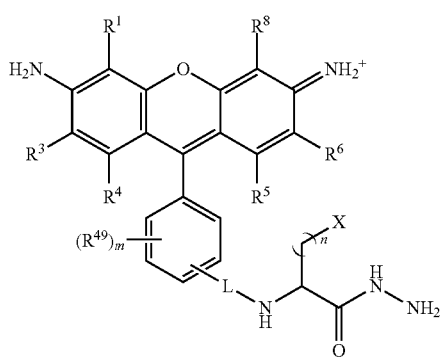

wherein,
L is a linker;
n is an integer from 1 to 24;
X is a molecule containing $SO_3H$, $SO_3^-$, $OPO_3^{2-}$, $OPO_3H_2$, $PO_3H_2$, $PO_3^{2-}$, COOH, or $COO^-$;
$R^1$, $R^3$, $R^4$, $R^5$, $R^6$, $R^8$ and $R^{49}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
m is 0, 1, or 2; and
b) instructions for detecting the analyte according to one or more of the methods described herein.

In certain embodiments, $R^1$ and $R^8$ are each sulfo; $R^2$, $R^3$, $R^4$, $R^5$, $R^6$, and $R^7$ are each H; $R^{49}$ is carboxy; m is 1; L is —C=O; X is selected from $N[(CH_2)_3SO_3H]_2$, $SO_3H$, $SO_3^-$, $OPO_3^{2-}$, $OPO_3H_2$, $PO_3H_2$, $PO_3^{2-}$, COOH, and $COO^-$; and n is 1, 2, 3 or 4. In certain embodiments, the compound of Formula (II) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a kit is provided for detecting an analyte in a sample, wherein the kit comprises:
a) a compound of Formula (III) or a tautomer or salt thereof:

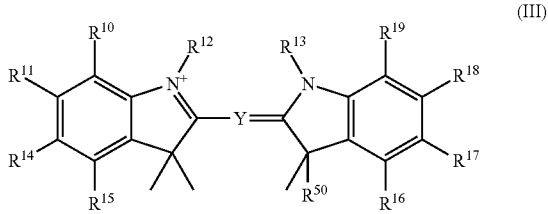

wherein,
Y is $—CR^{20}=(CR^{21}—CR^{22}=)_p$;
p is 0, 1, 2, or 3;
$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;
$R^{12}$ and $R^{13}$ are each independently H, alkyl, substituted alkyl, cycloalkyl, substituted cycloalkyl, aryl, substituted aryl, heteroaryl, substituted heteroaryl, heterocyclyl, substituted heterocyclyl;
$R^{50}$ is alkyl; and wherein one of $R^{13}$ or $R^{50}$ is:

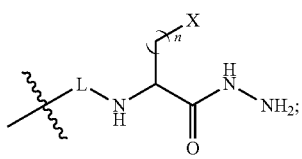

L is a linker;
n is an integer from 1 to 24; and
X is a molecule containing $SO_3H$, $SO_3^-$, $OPO_3^{2-}$, $OPO_3H_2$, $PO_3H_2$, $PO_3^{2-}$, COOH, or $COO^-$; and
b) instructions for detecting the analyte according to one or more of the methods described herein.

In certain embodiments, $R^{50}$ is methyl. In certain embodiments, the compound of Formula (III) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a kit is provided for detecting an analyte in a sample, wherein the kit comprises:

a) a compound of Formula (IV) or a tautomer or salt thereof:

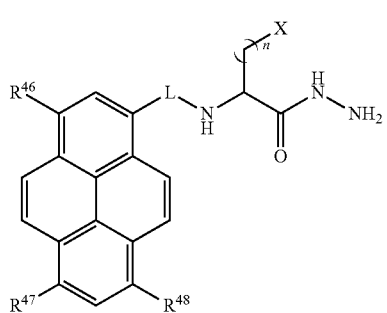

(IV)

wherein,
L is a linker;
n is an integer from 1 to 24;
X is a molecule containing $SO_3H$, $SO_3^-$, $OPO_3^{2-}$, $OPO_3H_2$, $PO_3H_2$, $PO_3^{2-}$, COOH, or $COO^-$; and
$R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
b) instructions for detecting the analyte according to one or more of the methods described herein.

In certain embodiments, $R^{46}$, $R^{47}$, and $R^{48}$ are each sulfo; X is carboxy; n is 1 or 2; and L is

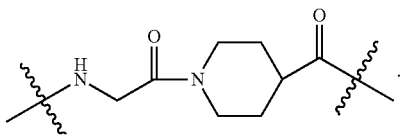 [SMILES: *NCC(=O)N1CCC(C(*)=O)CC1]

In certain embodiments, the compound of Formula (IV) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a kit is provided for detecting an analyte in a sample, wherein the kit comprises:

a) a compound of Formula (V) or a tautomer or salt thereof:

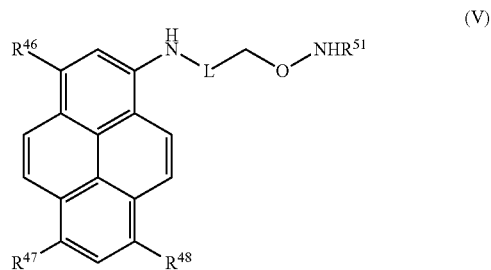

(V)

wherein,
L is a linker;
$R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^{51}$ is selected from H, alkyl and substituted alkyl; and b) instructions for detecting the analyte according to one or more of the methods described herein.

In certain embodiments, $R^{46}$, $R^{47}$, and $R^{48}$ are each sulfo, $R^{51}$ is H, and L is selected from the group consisting of: —$(CH_2)_5C(O)NH(CH_2)$—, —$(CH_2)_6NHC(O)$— and —C(O)—. In certain embodiments, the compound of Formula (V) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a kit is provided for detecting an analyte in a sample, wherein the kit comprises:
a) a compound selected from the group consisting of:
Compound 1
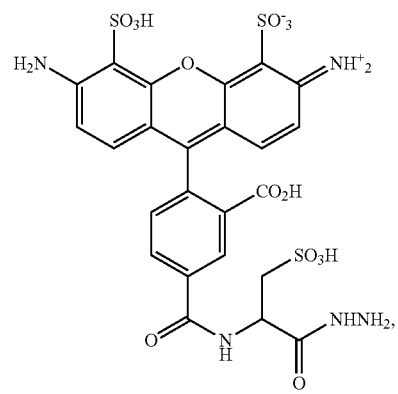
Compound 2
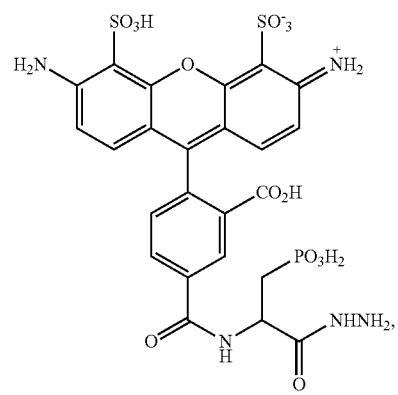
Compound 3
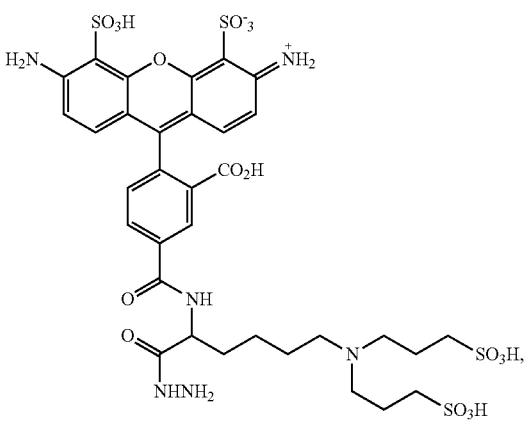
Compound 4
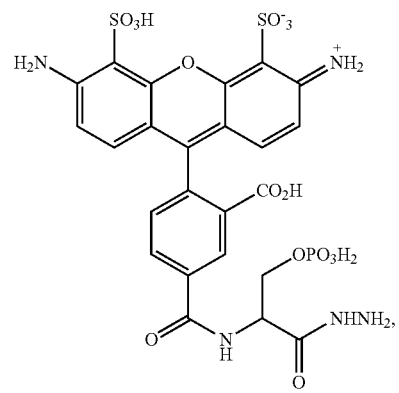
Compound 5
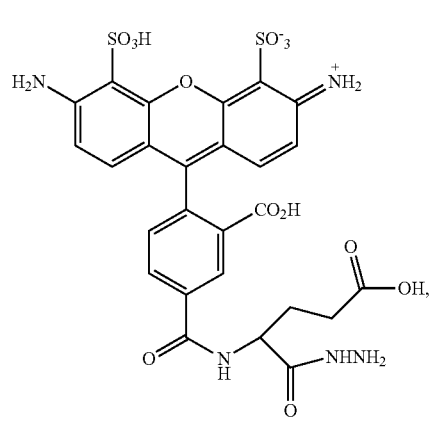
Compound 6
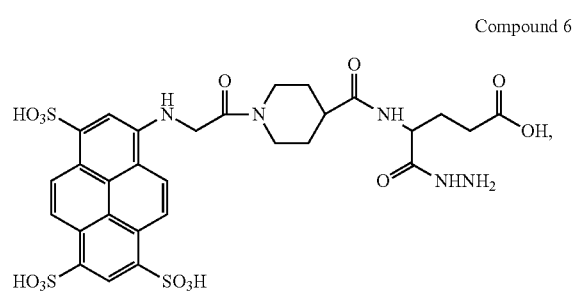
Compound 30
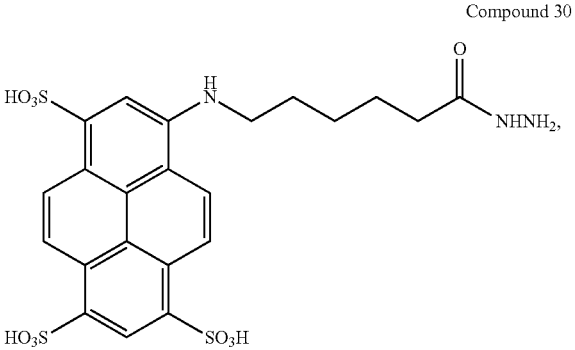

Compound 31

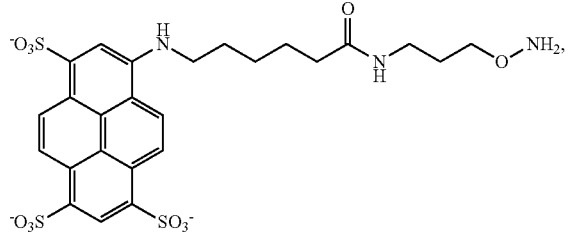

Compound 32

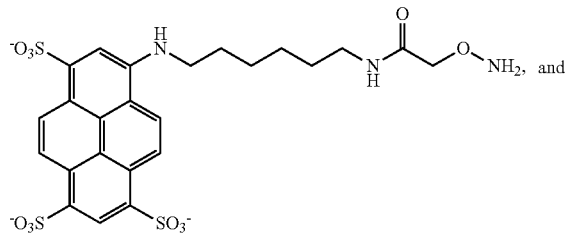

Compound 33

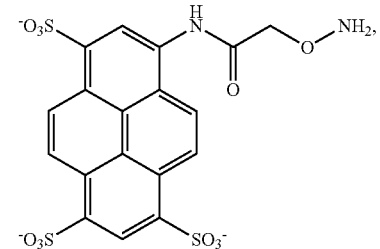

or a salt thereof; and b) instructions for detecting the analyte according to one or more of the methods described herein.

In certain embodiments, the compound is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, the kit further comprises instructions for covalently bonding the compound to the analyte. In certain embodiments, the kit further comprises one or more of the following: a buffering agent, a purification medium, a vial comprising the analyte, or an organic solvent, one or more reagents for releasing the glycan from a biomolecule, and optionally, one or more reagents to purify the released glycan from the reaction mixture. In certain embodiments, the reagent for releasing the glycan from a biomolecule is selected from a physical method, a chemical or an enzyme. In certain embodiments, the enzyme is PNGase F.

In certain embodiments, the purification medium is selected from the group consisting of a resin, a bead, a cartridge, a solid support, a plate and a well. In certain embodiments, the bead is a magnetic bead.

In certain embodiments, the kit further comprises instructions for labeling glycans in a sample in preparation of glycan analysis, the method comprising:

treating the sample with a release reagent, such as PNGase F enzyme, with an appropriate buffer under conditions suitable for the release of the glycan from the biomolecule, thereby forming a reaction mixture;

adding beads and buffer to the reaction mixture;
separating the supernatant from the beads;
washing the beads with wash buffer;
eluting the glycans from the beads with elution buffer;
performing dye labeling of the glycans using one or more dye compounds provided herein, thereby forming a glycan-containing solution;

optionally, removing excess dye using fresh beads; washing beads, separating the beads from excess dye/wash solution; and eluteing glycans from the beads; and collecting the glycan-containing solution.

In certain embodiments, the glycan solution may be stored for future use according to instructions provided, or analyzed for its glycan profile using a CE analyzer or uPLC analyzer or a combination thereof.

Certain embodiments provide the use of a compound, composition or kit of the invention for labeling an analyte. Certain embodiments provide the use of a compound, composition or kit of the invention for labeling a glycan.

Other objects, features and advantages of the present teachings will become apparent from the following detailed description. It should be understood, however, that the detailed description and the specific examples, while indicating preferred embodiments of the invention, are given by way of illustration only, since various changes and modifications within the spirit and scope of the disclosure will become apparent to those skilled in the art from this detailed description.

DETAILED DESCRIPTION

Figure 1:
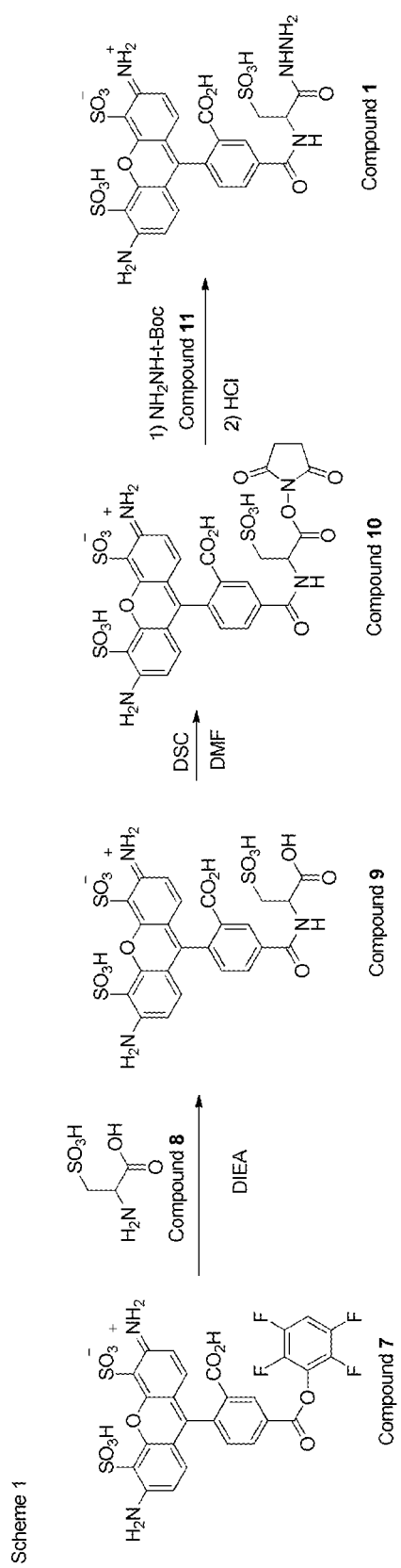
FIG. 1: Schematic of an exemplary synthesis scheme for the preparation of dye compounds comprising a sulfonate group according to certain embodiments disclosed herein.

Introduction:

The present disclosure provides compounds comprising a hydrazinyl substituent and optionally, one or more negatively charged groups, including but not limited to, sulfonate, phosphate, phosphonate, and carboxylate groups, which compounds are capable of binding aldehyde and ketone groups present on analytes of interest. Once the hydrazine reacts with an aldehyde or a ketone, a Schiff base (imine) is formed. The resultant compound is highly fluorescent thereby providing an excellent method for detection of aldehydes and ketones in solution.

Existing methods of labeling carbohydrates that utilize hydrazine, hydroxylamine and amine derivatization reagents have focused on labeling aldehydes present in, or introduced into, carbohydrates, particularly the so-called "reducing sugars". Aldehydes are typically introduced into carbohydrates by periodate oxidation. The adduct formed with the reducing sugar typically needs to be stabilized by treatment with borohydride or cyanoborohydride, both of which are toxic materials and present hazards to the user and for disposal. The derivatization reaction typically precedes or is followed by a separation technique such as chromatography, electrophoresis, precipitation, affinity isolation, or other means before direct or indirect detection of the labeled product.

The present disclosure also provides compounds comprising an aminooxy substituent, which compounds are capable of binding aldehyde and ketone groups present on analytes of interest. Once the aminooxy reacts with an aldehyde or a ketone, an oxime is formed. The resultant compound is highly fluorescent thereby providing an excellent method for detection of aldehydes and ketones in solution. Hydrolytic stability of the oxime formed from the aminooxy substituent is greater than for the hydrazone formed from the hydrazide substituent. Unsubstituted aminoxy linkers result in a predominantly ring-opened form whereas hydrazide and N-alkylaminoxy linkers give predominantly a ring-closed β-glycoside (see, FIG. 12C).

Unlike the foregoing methods previously available, which require purification and use of a secondary detection reagent; the dye compounds provided herein permit rapid in situ detection of aldehyde and ketone moieties upon contact and do not require reductive amination of the carbohydrate in the presence of toxic products, such as cyanoborohydride. The dye compounds disclosed herein provide distinct advantages over known aldehyde detection reagents including: 1) having a high quantum yield; 2) unique emission and excitation wavelengths outside the range of endogenous particles; 3) being highly stable; and 4) having high specificity for ketones and aldehydes. In addition, the dye compounds disclosed herein are soluble in a variety of solutions, particularly aqueous solutions and are compatible with biological applications. Additionally, reaction with the dye compounds provided herein proceeds under milder conditions (e.g., room temperature, aqueous acetic acid) than existing assays and does not require toxic compounds such as cyanoborohydride. Furthermore, the Schiff base formation appears to be a near-instantaneous reaction. Additionally, the available wavelength range for the dye compounds provided herein is large and tunable thereby allowing for multiplexing and/or multicolor detection. Furthermore, unlike the existing methods and reagents, the dye compounds provided herein are amenable to analysis by capillary electrophoresis-based oligosaccharide glycan labeling.

Definitions:

Before describing the present disclosure in detail, it is to be understood that this disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a hydrazine group" includes a plurality of hydrazine groups and reference to "an analyte" includes a plurality of analytes and the like.

It will be appreciated that there is an implied "about" prior to the temperatures, concentrations, times, etc. discussed in the present disclosure, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

Unless defined otherwise, all technical and scientific terms used herein have the same meaning as commonly understood by one of ordinary skill in the art to which this disclosure is related. The following terms are defined for purposes of the present disclosure as described herein.

The section headings used herein are for organizational purposes only and are not to be construed as limiting the desired subject matter in any way. All literature cited in the specification, including but not limited to, patents, patent applications, articles, books and treatises are expressly incorporated by reference in their entirety for any purpose. In the event that any of the incorporated literature contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The term "or combinations thereof" as used herein refers to all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Certain compounds of the present disclosure can exist in unsolvated forms as well as solvated forms, including hydrated forms. In general, the solvated forms are equivalent to unsolvated forms and are encompassed within the scope of the present disclosure. Certain compounds disclosed herein may exist in multiple crystalline or amorphous forms. In general, all physical forms are equivalent for the uses contemplated by the present disclosure and are intended to be within the scope of the present disclosure.

Certain compounds disclosed herein possess asymmetric carbon atoms (optical centers) or double bonds; the racemates, diastereomers, geometric isomers and individual isomers are encompassed within the scope of the present disclosure.

The compounds described herein may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, Acc. Chem. Res. 23:128 (1990).

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds disclosed herein, whether radioactive or not, are intended to be encompassed within the scope of the present disclosure.

Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

Selected compounds having a formal electronic charge may be shown without an appropriate biologically compatible counterion. Such a counterion serves to balance the positive or negative charge present on the compound. As used herein, a substance that is biologically compatible is not toxic as used, and does not have a substantially deleterious effect on biomolecules. Examples of negatively charged counterions include, among others, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Preferred counterions may include chloride, iodide, perchlorate and various sulfonates. Examples of positively charged counterions include, among others, alkali metal, or alkaline earth metal ions, ammonium, or alkylammonium ions.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, sulfo, sulfonyl, substituted sulfonyl, sulfonyloxy, thioacyl, thiol, alkylthio, and substituted alkylthio, wherein said substituents are defined herein.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Acyl includes the "acetyl" group $CH_3C(O)—$.

"Acylamino" refers to the groups —NRC(O)alkyl, —NRC(O)substituted alkyl, —NRC(O)cycloalkyl, —NRC(O)substituted cycloalkyl, —NRC(O)cycloalkenyl, —NRC(O)substituted cycloalkenyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic wherein R is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O— cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither $R^1$ nor R" are hydrogen.

"Aminooxy", "aminoxy" and "alkoxyamine" are interchangeable and refer to the group —O—$NH_2$ or —O—NRH, wherein R is alkyl or substituted alkyl as defined herein.

"Aminocarbonyl" refers to the group —C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —NRC(O)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NRC(S)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group —NR—SO$_2$NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkyenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —C(=NR''')R'R" where R', R", and R''' are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, sulfo, sulfonyl, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified, for example, by vinyl, allyl, and but-3-en-1-yl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, sulfo, sulfonyl, substituted sulfonyl, sulfonyloxy, thioacyl, thiol, alkylthio, and substituted alkylthio, wherein said substituents are defined herein and with the proviso that any hydroxy substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, sulfo, sulfonyl, substituted sulfonyl, sulfonyloxy, thioacyl, thiol, alkylthio, and substituted alkylthio, wherein said substituents are defined herein and with the proviso that any hydroxy substitution is not attached to an acetylenic carbon atom.

"Carbonyl" refers to the divalent group —C(O)— which is equivalent to —C(=O)—.

"Substituted carbonyl" refers to a divalent group —C(O)-alkyl-, —C(O)-substituted alkyl-, —C(O)-alkenyl, —C(O)-substituted alkenyl, —C(O)-alkynyl, —C(O)-substituted alkynyl, —C(O)— aryl, —C(O)-substituted aryl, —C(O)-cycloalkyl, substituted —C(O)-cycloalkyl, cycloalkenyl, —C(O)-substituted cycloalkenyl, —C(O)-heteroaryl, —C(O)-substituted heteroaryl, —C(O)-heterocyclic, and —C(O)-substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. The reverse representations are included in all of the above groups, to include the reversed direction of connectivity. For example, a substituted carbonyl of the class —C(O)-alkyl- includes -alky-C(O)—.

"Carboxyl" or "carboxy" refers to —COOH or salts thereof.

"Carboxamido" refers to the group —CONR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Carboxamidyl" refers to the divalent group —CONR'R"— or —R"R'NOC— where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic; or R' and R" are optionally joined together with the nitrogen bound thereto to form a heterocyclic or substituted heterocyclic group; where the first open valency is connected to the carbon of the carbonyl and the second open valency may be connected to either of R' or R" or from the heterocyclic/substituted heterocyclic group formed by combination of R' and R"; and where alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR—C(O)O-alkyl, substituted —NR—C(O)O-alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic wherein R is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, substituted —O—C(O)O-alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C<ring unsaturation and preferably from 1 to 2 sites of >C=C<ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocylyloxy, substituted heterocyclyloxy, heterocyclylthio, substituted heterocyclylthio, nitro, sulfo, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NRC(=NR)N(R)$_2$ where each R is independently selected from the group consisting of hydrogen, alkyl, substituted alkyl, aryl, substituted aryl, heteroaryl, substituted heteroaryl, heterocyclic, and substituted heterocyclic and two R groups attached to a common guanidino nitrogen atom are optionally joined together with the nitrogen bound thereto to form a heterocyclic or substituted heterocyclic group, provided that at least one R is not hydrogen, and wherein said substituents are as defined herein.

"H" indicates hydrogen.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocyclyl.

"Substituted heterocyclyloxy refers to the group —O-(substituted heterocyclyl).

"Heterocyclylthio" refers to the group —S-heterocyclyl.

"Substituted heterocyclylthio" refers to the group —S-(substituted heterocyclyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzob]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Hydrazinyl" refers to the group —NHNH$_2$—, =NNH—, or =N$^{(+)}$HNH$_2$—.

"Substituted hydrazinyl" refers to a hydrazinyl group, wherein a non-hydrogen atom, such as an alkyl group, is appended to one or both of the hydrazinyl amine groups. An example of substituted hydrazinyl is —N(alkyl)-NH$_2$ or =N+(alkyl)-NH$_2$.

"Nitro" refers to the group —NO$_2$.

"Oxo" refers to the atom (=O) or (—O$^-$).

"Spirocyclyl" refers to divalent saturated cyclic group from 3 to 10 carbon atoms having a cycloalkyl or heterocyclyl ring with a spiro union (the union formed by a single atom which is the only common member of the rings) as exemplified by the following structure:

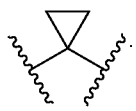 [SMILES: *C1(*)CC1]

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfo" refers to the groups —SO$_3^-$ and —SO$_3$H.

"Sulfonamido" refers to the group —SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonamidyl" refers to the divalent group —SO$_2$NR'R"— or —R"R'SO$_2$— where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic; or R' and R" are optionally joined together with the nitrogen bound thereto to form a heterocyclic or substituted heterocyclic group; where the first open valency is connected to sulfur and the second open valency may be connected to either of R' or R" or from the heterocyclic/substituted heterocyclic group formed by combination of R' and R"; and where alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$— cycloalkenyl, —OSO$_2$-substituted cylcoalkenyl, —OSO$_2$-aryl, —OSO$_2$-substituted aryl, —OSO$_2$— heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Substituted" refers to a molecule wherein one or more hydrogen atoms are replaced with one or more non-hydrogen atoms, functional groups or moieties. For example, an unsubstituted nitrogen is —NH$_2$, while a substituted nitrogen is —NHCH$_3$. Exemplary substituents include, but are not limited to, halo, e.g., fluorine and chlorine, lower alkyl, lower alkene, lower alkyne, sulfate, sulfone, sulfonate, amino, ammonium, amido, nitrile, lower alkoxy, phenoxy, aromatic, phenyl, polycyclic aromatic, heterocycle, and linking group. In case of conflicting definitions in sections below describing specific moieties, the description in the specific section will control.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., a methyl substituted with 5 fluoro groups). Such impermissible substitution patterns are well known to the skilled artisan.

A dashed line projecting from a substituent, such as:

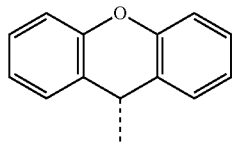

indicates the point of attachment to the base molecule. For a fused ring, dashed lines indicate portions of the base molecule where the fused ring is attached, such as:

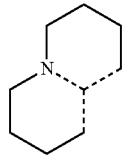

wherein the full molecule could have the structure:

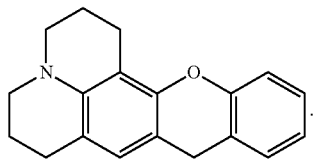

A squiggly line intersecting a bond, such as:

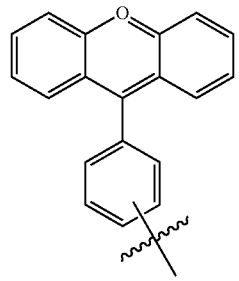

indicates the point of attachment to the base molecule, wherein in the above structure, the point of attachment is any unoccupied position on the phenyl ring.

"Stereoisomer" or "stereoisomers" refer to compounds that differ in the chirality of one or more stereocenters. Stereoisomers include enantiomers and diastereomers.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Patient," "subject" or "individual" refers to mammals and includes humans and non-human mammals, such as monkeys, dogs, cats, horses, cows, pigs or rats.

"Salt" refers to acceptable salts of a compound, which salts are derived from a variety of organic and inorganic counter ions well known in the art and include, by way of example only, sodium, potassium, calcium, magnesium, ammonium, tetraalkylammonium, alkylammonium, triethylammonium, tert-butylammonium, tetralkyl-phosphonium, tetraaryl-phosphonium, lithium and cesium; and when the molecule contains a basic functionality, salts of organic or inorganic acids, such as hydrochloride, hydrobromide, tartrate, mesylate, acetate, maleate, and oxalate.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

The terms "protein" and "polypeptide" are used herein in a generic sense to include polymers of amino acid residues of any length. The term "peptide" is used herein to refer to polypeptides having less than 250 amino acid residues, typically less than 100 amino acid residues. The terms apply to amino acid polymers in which one or more amino acid residues are an artificial chemical analogue of a corresponding naturally occurring amino acid, as well as to naturally occurring amino acid polymers.

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as carboxylic acid or succinimidyl ester, on the compounds of the present disclosure that is capable of chemically reacting with a functional group on a different compound to form a covalent linkage. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, aminooxy, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, (eds.), ORGANIC FUNCTIONAL GROUP PREPARATIONS, Academic Press, San Diego, 1989). Preferred reactive groups include aldehydes, hydrazines and hydrazides.

The term "detectable response" as used herein refers to an occurrence of or a change in, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "dye" as used herein refers to a compound that emits light to produce an observable detectable signal.

The term "fluorophore" or "fluorogenic" as used herein refers to a composition that demonstrates a change in fluorescence upon binding to a biological compound or analyte interest. Preferred fluorophores include fluorescent dyes having a high quantum yield in aqueous media. Exemplary fluorophores include pyrenes, xanthenes, indoles, borapolyazaindacenes, furans, and benzofurans, among others. The fluorophores may be substituted to alter the solubility, spectral properties or physical properties of the fluorophore.

The term "carrier molecule" as used herein refers to a biological or a non-biological component that is covalently bonded to a compound of the present disclosure. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. "Covalently bonded" as used herein indicates a direct covalent linkage or through a number of atoms corresponding to a linker moiety.

The term "Linker" as used herein, refers to a single covalent bond or a series of stable covalent bonds incorporating 1-20 nonhydrogen atoms selected from the group consisting of C, N, O, S and P that covalently attach the fluorogenic or fluorescent compounds to another moiety such as a chemically reactive group or a biological and non-biological component. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a fluorogenic or fluorescent moiety, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present disclosure to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleavable groups are known in the art. See, for example, Jung et al., Biochem. Biophys. Acta, 761: 152-162 (1983); Joshi et al., J. Biol. Chem., 265: 14518-14525 (1990); Zarling et al., J. Immunol., 124: 913-920 (1980); Bouizar et al., Eur. J. Biochem., 155: 141-147 (1986); Park et al., J. Biol. Chem., 261: 205-210 (1986); Browning et al., J. Immunol., 143: 1859-1867 (1989). Moreover a broad range of cleavable, bifunctional (both homo- and heterobifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

The linker can be used to attach the compound to another component of a conjugate, such as a targeting moiety (e.g., antibody, ligand, non-covalent protein-binding group, etc.), an analyte, a biomolecule, a drug and the like.

Dye Compounds:

The present disclosure describes dye compounds containing a hydrazinyl substituent and optionally, one or more negatively charged groups, including but not limited to, sulfonate, phosphate, phosphonate, and carboxylate groups, and methods of using such dye compounds for labeling aldehyde and ketone containing molecules, such as glycans. The compounds provided herein are capable of binding aldehyde and ketone groups present on analytes of interest. Once the hydrazine reacts with an aldehyde or a ketone, a Schiff base (imine) is formed. The resultant compound is highly fluorescent thereby providing an excellent method for detection of aldehydes and ketones in solution. A simple, sensitive reagent for the selective detection of aldehydes and/or ketones, such as the dye compounds provided herein, is a useful tool for high-throughput screening systems in chemistry and biology. In particular, aldehydes have been widely known as among the key end products from the degradation of a variety of biological molecules, e.g. lipids, nucleic acids, carbohydrates, proteins, induced by oxidative stress.

Certain embodiments provide a compound of Formula (I) or a tautomer or salt thereof:

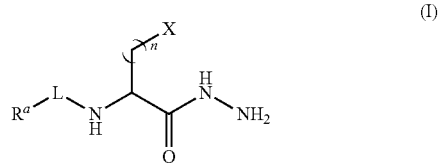

(I)

wherein,
L is a linker;
$R^a$ is a reporter molecule, carrier molecule or a solid support;
n is an integer from 1 to 24; and
X is a molecule containing $SO_3H$, $SO_3^-$, $OPO_3^{2-}$, $OPO_3H_2$, $PO_3H_2$, $PO_3^{2-}$, COOH, or $COO^-$.

In certain embodiments, L is a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is a dye. More particularly, the dye is a pyrene, a xanthene, a cyanine, an indole, a benzofuran, a coumarin, or a borapolyazaindacine.

In certain embodiments, $R^a$ is a chelating moiety, a hapten, an antibody, an enzyme, a radiolabel, a metal ion or metal ion containing substance, a pigment, a chromogen, a phosphor, a fluorogen, a bioluminescent substance, a chemiluminescent substance, or a semiconductor nanocrystal. More particularly, $R^a$ is avidin, streptavidin or an analog thereof.

In certain embodiments, $R^a$ is a solid support.

In certain embodiments, $R^a$ is a carrier molecule. More particularly, the carrier molecule is selected from the group consisting of an amino acid, a peptide, a protein, a carbohydrate, a polysaccharide, a nucleoside, a nucleotide, an oligonucleotide, a nucleic acid polymer, a drug, a lipid, and a synthetic polymer.

In certain embodiments, the compound of Formula (I) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, $R^a$ is:

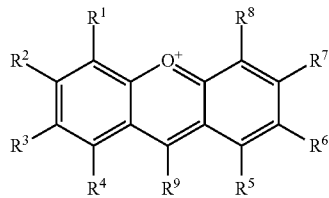

or a tautomer or salt thereof;
wherein,
$R^1$, $R^2$, $R^3$, $R^4$, $R^5$, $R^6$, $R^7$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or one or more of $R^1$ and $R^2$, $R^2$ and $R^3$, $R^3$ and $R^4$, $R^5$ and $R^6$, $R^6$ and $R^7$ or $R^7$ and $R^8$ are taken together to form a fused aryl or heteroaryl group; and one of $R^1$, $R^2$, $R^3$, $R^4$, $R^5$, $R^6$, $R^7$, $R^8$ and $R^9$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In an embodiment, $R^3$, $R^4$, $R^5$, $R^6$ are H. In an embodiment, $R^9$ is the point of attachment to L. In certain embodiments $R^1$ and $R^8$ are each sulfo. In certain embodiments $R^2$ and $R^7$ are each amino. In certain embodiments $R^2$, $R^3$, $R^4$, $R^5$, $R^6$, and $R^7$ are each H. In certain embodiments m is 1. In certain embodiments L is —C=O. In certain embodiments X is selected from N[(CH$_2$)$_3$SO$_3$H]$_2$, SO$_3$H, SO$_3^-$, OPO$_3^{2-}$, OPO$_3$H$_2$, PO$_3$H$_2$, PO$_3^{2-}$, COOH, and COO$^-$. In certain embodiments, n is 1, 2, 3 or 4, for example n may be 1.

In certain embodiments $R^3$, $R^4$, $R^5$, $R^6$ may be H, $R^9$ may be the point of attachment to L, and optionally N may be 1, 2, 3 or 4. In certain embodiments, $R^1$ and $R^8$ are each sulfo; $R^2$ and $R^7$ are each amino; and optionally $R^3$, $R^4$, $R^5$, $R^6$ may be H. In certain embodiments, $R^1$ and $R^8$ are each sulfo; $R^2$ and $R^7$ are each amino; $R^3$, $R^4$, $R^5$, $R^6$, and are each H; L comprises phenyl; X is selected from N[(CH$_2$)$_3$SO$_3$H]$_2$, SO$_3$H, SO$_3^-$, OPO$_3^{2-}$, OPO$_3$H$_2$, PO$_3$H$_2$, PO$_3^{2-}$, COOH, and COO$^-$; n is 1, 2, 3 or 4; and optionally $R^9$ is the point of attachment to L. In certain embodiments the compound is a salt; for example a salt comprising a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, $R^a$ is:

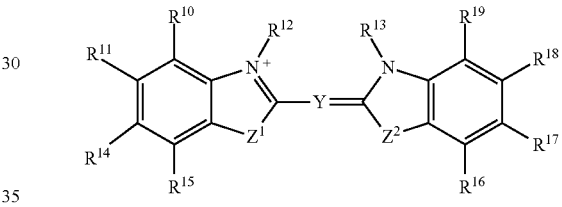

or a tautomer or salt thereof;
wherein,
$Z^1$ and $Z^2$ are each independently O, S, NR$^{23}$ or CR$^{24}$R$^{25}$;
Y is —CR$^{20}$=(CR$^{21}$—CR$^{22}$=)$_p$;
p is 0, 1, 2, or 3;
$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$, $R^{13}$ and $R^{23}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{20}$, $R^{21}$ and $R^{22}$ are each independently, H, alkyl, substituted alkyl, cycloalkyl, substituted cycloalkyl, aryl, substituted aryl, heteroaryl, or substituted heteroaryl;

$R^{24}$ and $R^{25}$ are H, alkyl or substituted alkyl; and
one of $R^{10}$, $R^{11}$, $R^{12}$, $R^{13}$, $R^4$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

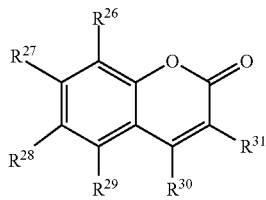

or a tautomer or salt thereof;
wherein,
$R^{26}$, $R^{27}$, $R^{28}$, $R^{29}$, $R^{30}$ and $R^{31}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{26}$, $R^{27}$, $R^{28}$, $R^{29}$, $R^{30}$ and $R^{31}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

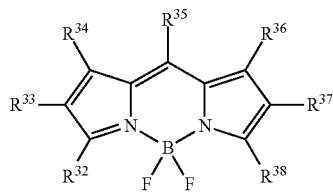

or a tautomer or salt thereof;
wherein,
$R^{32}$, $R^{33}$, $R^{34}$, $R^{35}$, $R^{36}$, $R^{37}$ and $R^{38}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{32}$, $R^{33}$, $R^{34}$, $R^{35}$, $R^{36}$, $R^{37}$ and $R^{38}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

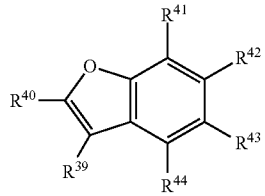

or a tautomer or salt thereof;
wherein,
$R^{39}$, $R^{40}$, $R^{41}$, $R^{42}$, $R^{43}$ and $R^{44}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{39}$, $R^{40}$, $R^{41}$, $R^{42}$, $R^{43}$ and $R^{44}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

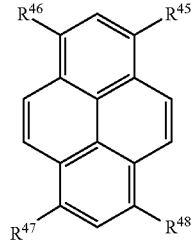

or a tautomer or salt thereof;
wherein,
$R^{45}$, $R^{46}$, $R^{47}$, and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{45}$, $R^{46}$, $R^{47}$, and $R^{48}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, provided herein is a compound of Formula (II) or a tautomer or salt thereof:

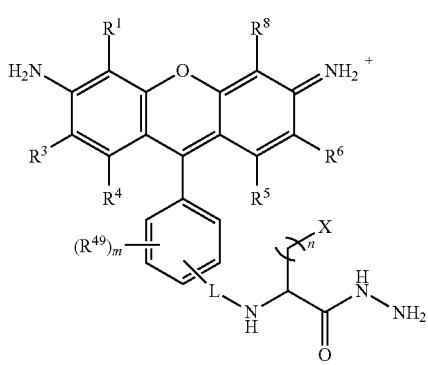

wherein,

L is a linker;

n is an integer from 1 to 24;

X is a molecule containing $SO_3H$, $SO_3^-$, $OPO_3^{2-}$, $OPO_3H_2$, $PO_3H_2$, $PO_3^{2-}$, COOH, or $COO^-$;

$R^1$, $R^3$, $R^4$, $R^5$, $R^6$, $R^8$ and $R^{49}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and m is 0, 1, or 2.

In certain embodiments $R^1$ and $R^8$ are each sulfo. In certain embodiments $R^2$, $R^3$, $R^4$, $R^5$, $R^6$, and $R^7$ are each H. In certain embodiments $R^{49}$ are carboxy. In certain embodiments m is 1. In certain embodiments L is —C═O. In certain embodiments X is selected from $N[(CH_2)_3SO_3H]_2$, $SO_3H$, $SO_3^-$, $OPO_3^{2-}$, $OPO_3H_2$, $PO_3H_2$, $PO_3^{2-}$, COOH, and $COO^-$. In certain embodiments, n is 1, 2, 3 or 4, for example n may be 1. In certain embodiments, $R^1$ and $R^8$ are each sulfo; $R^2$, $R^3$, $R^4$, $R^5$, $R^6$, and $R^7$ are each H; $R^{49}$ is carboxy; m is 1; L is —C═O; X is selected from $N[(CH_2)_3SO_3H]_2$, $SO_3H$, $SO_3^-$, $OPO_3^{2-}$, $OPO_3H_2$, $PO_3H_2$, $PO_3^{2-}$, COOH, and $COO^-$; and n is 1, 2, 3 or 4. In certain embodiments, the compound of Formula (II) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, provided herein is a compound of Formula (III) or a tautomer or salt thereof:

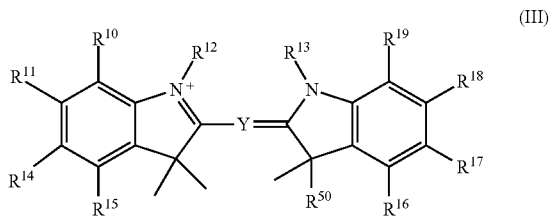

wherein,

Y is —$CR^{20}$═($CR^{21}$—$CR^{22}$═)$_p$;

p is 0, 1, 2, or 3;

$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$ and $R^{13}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{50}$ is alkyl; and wherein one of $R^{13}$ or $R^{50}$ is:

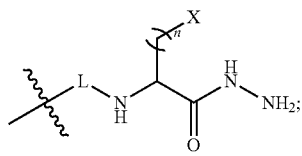

L is a linker;

n is an integer from 1 to 24; and

X is a molecule containing $SO_3H$, $SO_3^-$, $OPO_3^{2-}$, $OPO_3H_2$, $PO_3H_2$, $PO_3^{2-}$, COOH, or $COO^-$.

In certain embodiments, $R^{50}$ is alkyl. In certain embodiments, the compound of Formula (III) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, provided herein is a compound of Formula (IV) or a tautomer or salt thereof:

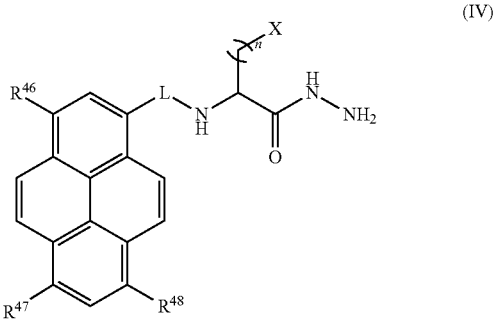

(IV)

wherein,

L is a linker;

n is an integer from 1 to 24;

X is a molecule containing $SO_3H$, $SO_3^-$, $OPO_3^{2-}$, $OPO_3H_2$, $PO_3H_2$, $PO_3^{2-}$, COOH, or $COO^-$; and $R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl.

In certain embodiments, $R^{46}$, $R^{47}$, and $R^{48}$ are each sulfo. In certain embodiments X is carboxy. In certain embodiment n is 1 or 2. In certain embodiments L is

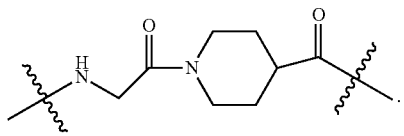 [SMILES: *NCC(=O)N1CCC(C(*)=O)CC1]

In certain embodiments, $R^{46}$, $R^{47}$, and $R^{48}$ are each sulfo; X is carboxy; n is 1 or 2; and L is

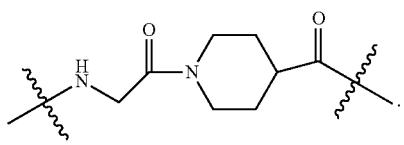 [SMILES: *NCC(=O)N1CCC(C(*)=O)CC1]

In certain embodiments, the compound of Formula (IV) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

The present disclosure also provides compounds comprising an aminooxy substituent, which compounds are capable of binding aldehyde and ketone groups present on analytes of interest. Once the aminooxy reacts with an aldehyde or a ketone, an oxime is formed. The resultant compound is highly fluorescent thereby providing an excellent method for detection of aldehydes and ketones in solution. Hydrolytic stability of the oxime formed from the aminooxy substituent is greater than for the hydrazone formed from the hydrazide substituent. Unsubstituted aminoxy linkers result in a predominantly ring-opened form whereas hydrazide and N-alkylaminoxy linkers give predominantly a ring-closed β-glycoside (see, FIG. 12C).

In certain embodiments, provided herein is a compound of Formula (V) or a tautomer or salt thereof:

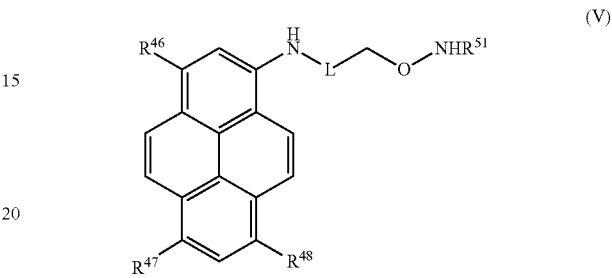

(V)

wherein,

L is a linker;

$R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^{51}$ is selected from H, alkyl and substituted alkyl.

In certain embodiments, $R^{46}$, $R^{47}$, and $R^{48}$ are each sulfo. In certain embodiments $R^{51}$ is H. In certain embodiments and L is selected from the group consisting of: $-(CH_2)_5C(O)NH(CH_2)_2-$, $-(CH_2)_6NHC(O)-$ and $-C(O)-$. For example, L may be $-(CH_2)_5C(O)NH(CH_2)_2-$. For example, L may be $-(CH_2)_6NHC(O)-$. For example, L may be $-C(O)-$. In certain embodiments, $R^{46}$, $R^{47}$, and $R^{48}$ are each sulfo, and $R^{51}$ is H, In certain embodiments, $R^{51}$ is H, and L is selected from the group consisting of: $-(CH_2)_5C(O)NH(CH_2)_2-$, $-(CH_2)_6NHC(O)-$ and $-C(O)-$. In certain embodiments, $R^{46}$, $R^{47}$, and $R^{48}$ are each sulfo, and L is selected from the group consisting of: $-(CH_2)_5C(O)NH(CH_2)_2-$, $-(CH_2)_6NHC(O)-$ and $-C(O)-$.

In certain embodiments, $R^{46}$, $R^{47}$, and $R^{48}$ are each sulfo, $R^{51}$ is H, and L is selected from the group consisting of: $-(CH_2)_5C(O)NH(CH_2)_2-$, $-(CH_2)_6NHC(O)-$ and $-C(O)-$. In certain embodiments, the compound of Formula (V) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In another aspect, compounds are provided selected from the group consisting of:

Compound 1
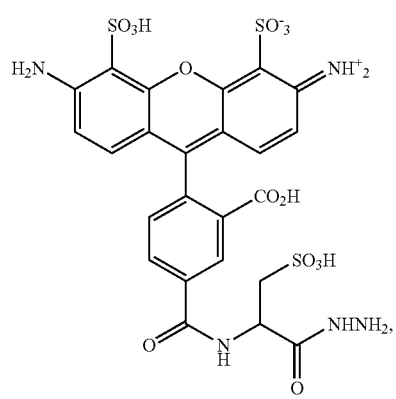
Compound 2
Compound 3
Compound 4
Compound 5
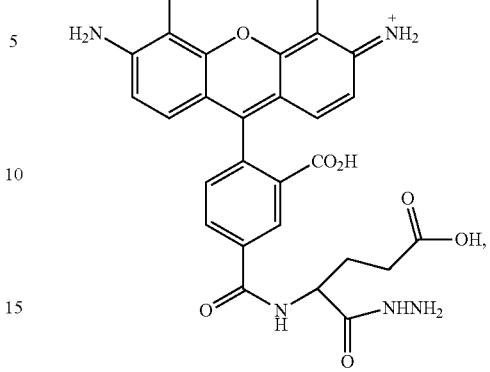
Compound 6
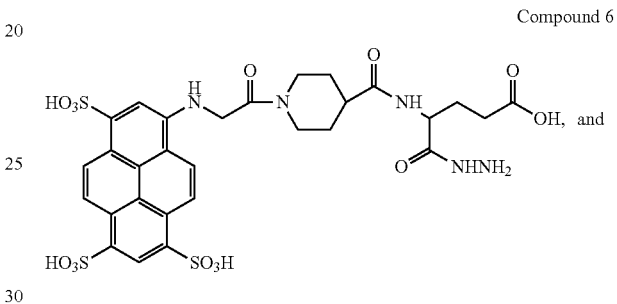
Compound 30
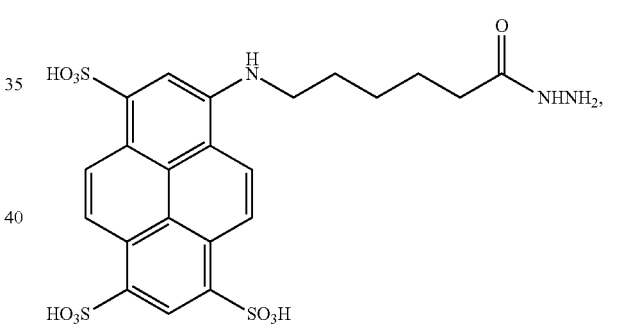
Compound 31
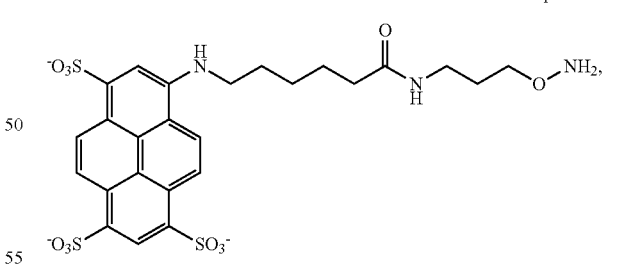
Compound 32
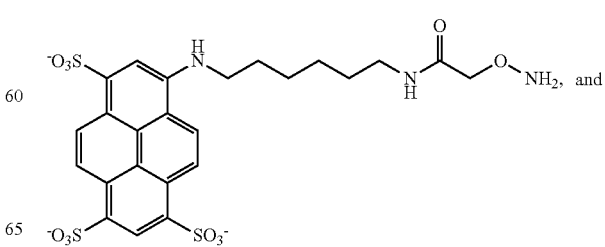

Compound 33

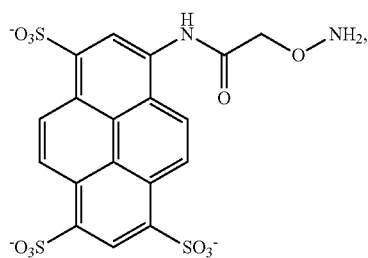

or a salt thereof.

In certain embodiments, the compound is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

Certain embodiments provide compounds comprising any of the dye compounds disclosed herein, wherein the hydrazine group or the aminooxy group is unsubstituted or substituted with an analyte.

A simple, sensitive reagent for the selective detection of aldehydes/ketones is a useful tool for high-throughput screening systems in chemistry and biology. In particular, aldehydes have been widely known as among the key end products from a degradation of a variety of biological molecules, e.g. lipids, nucleic acids, carbohydrates, proteins, induced by oxidative stress.

MDA is known to react with aryl hydrazines to form pyrazoles (Otteneder et al, "Reaction of Malondialdehyde-DNA adducts with Hydrazines-Development of a Facile Assay for Quantification of Malondialdehyde Equivalents in DNA," *Chem. Res. Toxicol.* 2002, 15: 312-8). The compounds disclosed herein may be used for the detection and quantitation of aldehyde/ketone functional groups. The compounds are capable of reacting with a variety of analytes, such as malondialdehyde (MDA), and an exemplary reaction is portrayed in the reaction scheme below.

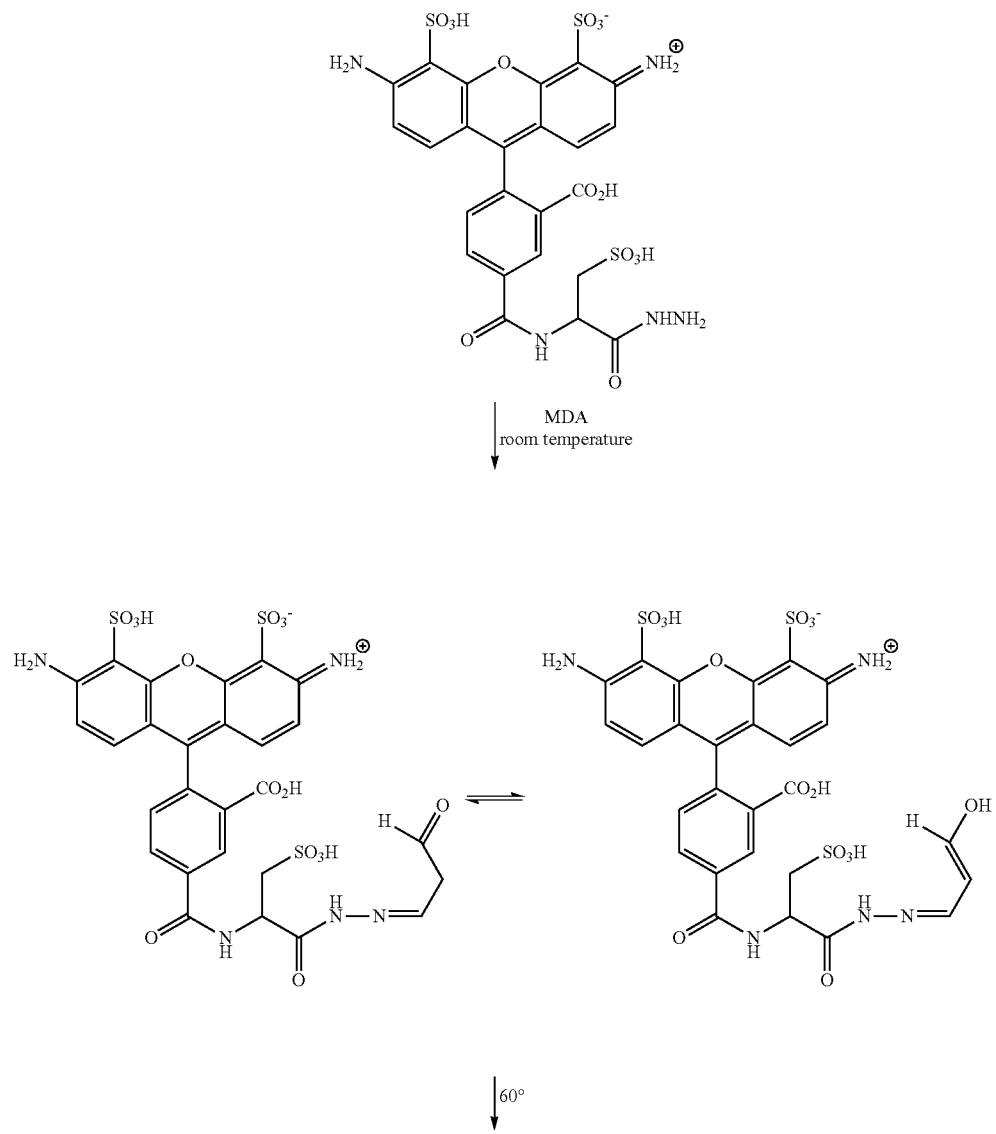

-continued

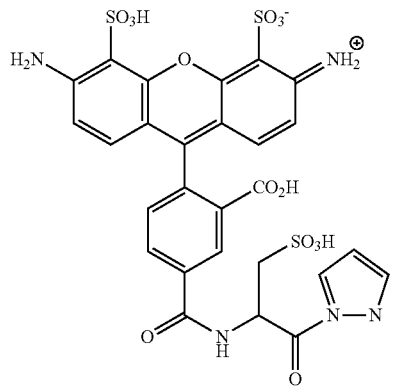

The aldehyde or ketone functional group is typically naturally present on the analyte prior to its conjugation to a dye compound provided herein. Alternatively, the aldehyde or ketone functionality is formed on the target substance by chemical, light, heat, radiation, or enzymatic treatment prior to reaction with a dye compound provided herein. In one aspect of the present disclosure, the target substance is treated with an oxidizing condition, such as a chemical oxidizing agent (for example, a periodate, a strong acid, or ozone), oxidizing radiation, photolysis, or enzymatic oxidation.

Where they are not present, aldehydes and ketones are also introduced into molecules using extrinsic reagents that already contain an aldehyde or ketone. For instance, aldehydes are introduced at aliphatic amine sites with the reagents succinimidyl 4-formylbenzoate or succinimidyl 4-formylphenoxyacetate (Molecular Probes, Eugene Oreg.). These reagents selectively modify proteins on the surface of live cells, and thereby permit the analysis of the topology of peptide and protein exposure on cells surfaces following, for instance, lysis and gel electrophoresis. Additionally, galactosides are enzymatically transferred to a target carbohydrate using UDP-galactose:N-acetylglucosamine galactosyltransferase and, following galactose oxidase-catalyzed oxidation to an aldehyde (as described by Shaper et al. *J. Supramol. Structure* 6: 291-299 (1977)), the target carbohydrate can be modified by a dye compound provided herein. Glycoproteins such as horseradish peroxidase are oxidized to aldehydes and their conjugates subsequently used in various detection schemes according to the instant disclosure.

The present disclosure also provides compounds comprising an aminooxy substituent, which compounds are capable of reacting aldehyde and ketone groups present on analytes of interest. Once the aminooxy reacts with an aldehyde or a ketone, an oxime is formed. The resultant compound is highly fluorescent thereby providing an excellent method for detection of aldehydes and ketones in solution.

Aminooxy or aminoxy-containing compounds are also known as alkoxyamine and these compounds conjugate to carbonyls (aldehydes and ketones) in much the same way as hydrazides; however, in this case, the reaction results in an oxime linkage (see the reaction scheme below wherein R is a labeling reagent and P is a b-glycoprotein or other glycosylated molecule).

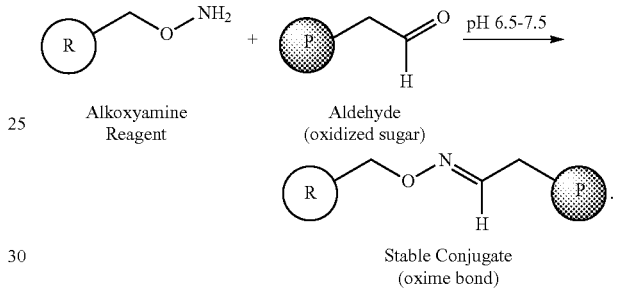

Hydrolytic stability of the oxime formed from the aminooxy substituent is greater than for the hydrazone formed from the hydrazide substituent (Kalia et al. *Angew. Chem. Int. Ed. Engl.* 47:7523 (2008)). Unsubstituted aminoxy linkers result in a predominantly ring-opened form whereas hydrazide and N-alkylaminoxy linkers give predominantly a ring-closed β-glycoside (Liu et al. *Chem. Biol.* 14:847 (2007), Lee et al. *Org. Lett.* 7:4269 (2005), Bohorov et al. *Glycobiology* 16:C21 (2006)). Schematics for various methods for reduced end conjugation of glycans are described in FIG. 12C.

The oligosaccharide components of cell surface glycoproteins play a role in the interactions that regulate many important biological processes, from cell-cell adhesion to signal transduction. Sialic acids are the most abundant terminal components of oligosaccharides on mammalian cell-surface glycoproteins and are synthesized from the six-carbon precursor N— actylmannosamine. When cells in culture are incubated with N-levulinoyl-D-mannosamine, this ketone-containing monosaccharide serves as a substrate in the oligosaccharide synthesis pathway, resulting in ketone-tagged cell-surface oligosaccharides (as described in U.S. Pat. No. 6,075,134 to Bertozzi et al. (2000), incorporated by reference). If these tagged cells are then labeled with a dye compound disclosed herein, they are readily identified or traced using, for example, imaging or flow cytometry.

The conjugated target is typically a peptide, a protein, a nucleoside, a nucleotide, an oligonucleotide, a nucleic acid, a sugar, a polysaccharide, a lipid, a lipopolysaccharide, a ganglioside, a drug, a hormone, or a ligand having a molecular weight less than 2,000 Daltons. Preferably, the conjugated target is a protein, a nucleic acid, a lipid, a lipopolysaccharide, a ganglioside, a drug, or a hormone.

The use of the present disclosure to label aldehyde- and ketone-containing target substances comprises combining a dye compound of the present disclosure with a sample that contains or is thought to contain a desired target, incubating the mixture of dye compound and sample for a time sufficient for the reagent to form a covalent conjugate with the target substance in the sample, such that the conjugate exhibits a detectable fluorescent signal.

The characteristics of the resulting dye compound-target conjugate, including the presence, location, intensity, excitation and emission spectra, fluorescence polarization, fluorescence lifetime, photobleaching rate and other physical properties of the fluorescent signal can be used to detect, differentiate, sort, quantitate, and/or analyze aspects or portions of the sample. The dye compounds provided herein are optionally used in conjunction with one or more additional detection reagents (preferably having detectably different fluorescence characteristics).

Selected target substances containing aldehydes or ketones include, but are not limited to formaldehyde, acetone, benzaldehydes, reducing sugars and polysaccharides in ring-opened forms, steroids, keto acids, aldehyde- or ketone-containing drugs, aldehyde- or ketone-containing environmental pollutants, aldehyde- or ketone-containing organics, acid-treated deoxyribonucleic acids, oxidized sugars, oxidized polysaccharides, oxidized glycols, oxidized glycoproteins, oxidized glycolipids, oxidized glycosaminoglycans, oxidized ribonucleic acids, oxidized biological cells, oxidized N-terminal serine residues of proteins, and oxidized N— terminal threonine residues of proteins.

Typically, when a dye compound of the present disclosure is used in the form of a staining solution, it is preferably in an aqueous or aqueous miscible solution that is compatible with the sample and the intended use. For biological samples, where minimal perturbation of cell morphology or physiology is desired, the staining solution is selected accordingly. For solution assays, the staining solution preferably does not perturb the native conformation of the target substance.

Although typically used in an aqueous or aqueous miscible solution, the staining solution is typically prepared by first dissolving the reagent in a water-miscible organic solvent such as dimethylsulfoxide (DMSO), dimethylformamide (DMF), or a lower alcohol, such as methanol or ethanol. This stock solution is typically prepared at a concentration of greater than about 50-times that used in the final staining solution, then diluted one or more times with an aqueous solvent or a buffer solution such that the dye compound is present in an effective amount. Typically, the reagent is first dissolved in 100% DMF, and then diluted with buffer. The staining solution optionally further comprises additional formulation components, such as acids, buffering agents, inorganic salts, polar organic solvents, antioxidants, and ion chelators.

The pH of the staining solution is optionally modified by the inclusion of a buffering agent. Any buffering agent that is compatible with the target substance in the sample is suitable for inclusion in the staining solution. In a preferred embodiment the buffer is PBS. In another embodiment, the buffering agent is one of the so-called "Good's" buffers. "Good's" buffers include BES (N,N-bis[2-hydroxyethyl]-2-aminoethanesulfonic acid; 2-[bis(2-hydroxyethyl)amino] ethanesulfonic acid), BICINE (N,N-bis[2-hydroxyethyl]glycine), CAPS (3-[cyclohexylamino]-1-propanesulfonic acid), EPPS (N-[2-hydroxyethyl]piperazine-N'-[3-propanesulfonic acid]), HEPES ((N-[2-hydroxyethyl]piperazine-N'-[2-ethanesulfonic acid]), MES (2-[N-morpholino]ethanesulfonic acid), MOPS (3-[N-morpholino]propanesulfonic acid), PIPES (piperazine-N,N'-bis[2-ethanesulfonic acid]; 1,4-piperazinediethanesulfonic acid), TAPS (N-tris [hydroxymethyl]methyl-3-aminopropanesulfonic acid; ([2-hydroxy-1,1-bis(hydroxymethyl)ethyl]amino-1-propanesulfonic acid), TES (N-tris[hydroxymethyl]methyl-2-aminoethanesulfonic acid; 2-([2-hydroxy-1,1-bis(hydroxymethyl)ethyl]amino) ethanesulfonic acid), or TRICINE (N-tris [hydroxymethyl] methylglycine; N-[2-hydroxy-1,1-bis(hydroxymethyl)ethyl] glycine).

Other preferred buffering agents include salts of formate, citrate, acetate, N-(2-hydroxyethyl)-N'-(2-sulfoethyl)piperazine, imidazole, N-(2-hydroxyethylpiperazine)-N'-2-ethanesulfonic acid, Tris(hydroxymethyl)aminomethane acetate, or Tris (hydroxymethyl)aminomethane hydrochloride. In a preferred embodiment, the buffering agent is MES, sodium acetate, or acetic acid, preferably acetic acid. The buffering agent or mixture of buffering agents is typically present in the staining solution at a concentration of 20 mM to 500 mM, preferably about 25 mM to about 100 mM. Where the buffering agent is acetic acid, it is preferably present in a concentration of about 1%-6%, more preferably at about 3%.

An effective amount of dye compound is the amount of dye compound sufficient to give a detectable fluorescence response in combination with the desired target. The dye compound concentration in the solution must be sufficient both to contact the target in the sample and to combine with the target in an amount sufficient to give a signal, but too much dye compound may cause problems with background fluorescence or speckling in gels. The optimal concentration and composition of the staining solution is determined by the nature of the sample (including physical, biological, biochemical and physiological properties), the nature of the dye compound-target interaction (including the transport rate of the reagent to the site of the target), and the nature of the analysis being performed, and can be determined using standard procedures, similar to those described in examples below.

In another embodiment, the target substance contains a carboxylic acid or sulfonic acid functional group, therefore the functional group must first be activated before combining with a staining solution containing a dye compound provided herein, depending upon the properties of the target substance. Typically carbodiimides, such as EDAC, or dicyclohexylcarbodiimide (DCC) are used to activate carboxylic acids, whereas sulfonic acids most often require formation of their sulfonyl chloride by standard means. The reagent adducts of carboxylic acids and sulfonic acids are typically used to characterize the target substance, or the conjugates are used as fluorescent tracers. Carboxylic acid and sulfonic acids do not form stable adducts when stained in gels or solutions, thus differentiating them from aldehydes and ketones.

Reactive Groups:

In an exemplary embodiment, the compounds provided herein comprise a reactive group which is a member selected from an acrylamide, an activated ester of a carboxylic acid, an acyl azide, an acyl nitrile, an aldehyde, an alkyl halide, an anhydride, an aniline, an aminooxy, an aryl halide, an azide, an aziridine, a boronate, a carboxylic acid, a diazoalkane, a haloacetamide, a halotriazine, a hydrazine, a hydrazide, an imido ester, an isocyanate, an isothiocyanate, a maleimide, a phosphoramidite, a reactive platinum complex, a sulfonyl halide, a thiol group, and a photoactivatable group. Preferred reactive groups include aldehydes, hydrazines, hydrazides, aminooxy and ketones.

These reactive groups can be covalently attached either during or after the synthesis of the dyes in order to provide reactive group-containing dyes. In this way, reactive group-containing dyes can be covalently attached to a wide variety of carrier molecules or solid supports that contain or are modified to contain functional groups with suitable reactivity, resulting in chemical attachment of the components. In an exemplary embodiment, the reactive group of a dye compound disclosed herein and the functional group of the carrier molecule of solid support comprise electrophiles and nucleophiles that can generate a covalent linkage between them. Alternatively, the reactive group comprises a photo-activatable group, which becomes chemically reactive only after illumination with light of an appropriate wavelength. Typically, the conjugation reaction between the reactive group and the carrier molecule or solid support results in one or more atoms of the reactive group being incorporated into a new linkage attaching the dye compound to the carrier molecule or solid support. Selected examples of functional groups and linkages are shown in Table 1, where the reaction of an electrophilic group and a nucleophilic group yields a covalent linkage.

TABLE 1

Examples of some routes to useful covalent linkages with electrophile and nucleophile reactive groups

| Electrophilic Group | Nucleophilic Group | Resulting Covalent Linkage |
|---|---|---|
| activated esters* | amines/anilines | carboxamides |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |

TABLE 1-continued

Examples of some routes to useful covalent linkages with electrophile and nucleophile reactive groups

| Electrophilic Group | Nucleophilic Group | Resulting Covalent Linkage |
|---|---|---|
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g. oxysuccinimidyl (—OC$_4$H$_4$O$_2$) oxysulfosuccinimidyl (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates Choice of the reactive group used to attach a dye compound of the present disclosure to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica. Preferably, reactive groups react with an amine or a thiol functional group, or with silica. In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327.

Where the reactive group is an activated ester of a carboxylic acid, such as a succinimidyl ester of a carboxylic acid, a sulfonyl halide, a tetrafluorophenyl ester or an isothiocyanates, the resulting compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and 5,573,904) the resulting compound is particularly useful for conjugation to thiol-containing substances. Where the reactive group is a hydrazide or aminooxy, the resulting compound is particularly useful for conjugation to glycans with a reducing end, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantification.

In a particular aspect, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. In this way, dye compounds provided herein that comprise a photoactivatable reactive group associate with anionic proteins and can be covalently conjugated to the proteins. Photoactivatable reactive groups include, without limitation, benzophenones, aryl azides and diazirines.

In certain embodiments, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. In certain embodiments, the reactive group is a succinimidyl ester of a carboxylic acid, a maleimide, an iodoacetamide, or a silyl halide. In a particular embodiment the reactive group is a succinimidyl ester of a carboxylic acid, a sulfonyl halide, a tetrafluorophenyl ester, an iosothiocyanates or a maleimide.

The selection of a covalent linkage to attach the reporter molecule to the carrier molecule or solid support typically depends on the chemically reactive group on the component to be conjugated. The discussion regarding reactive groups in the section immediately preceding is relevant here as well. In addition to the hydrazinyl or aminooxy appendage, exemplary reactive groups typically present on the biological or non-biological components include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the component (typical for polysaccharides), or a variety of sites may occur (e.g. amines, thiols, alcohols, phenols), as is typical for proteins. A carrier molecule or solid support may be conjugated to more than one reporter molecule, which may be the same or different, or to a substance that is additionally modified by a hapten. Although some selectivity can be obtained by careful control of the reaction conditions, selectivity of labeling is best obtained by selection of an appropriate reactive compound.

Carrier Molecules:

In another exemplary embodiment, the dye compound is covalently bound to a carrier molecule. If the compound has a reactive group, then the carrier molecule can alternatively be linked to the compound through the reactive group. The reactive group may contain both a reactive functional moiety and a linker, or only the reactive functional moiety.

A variety of carrier molecules are useful in the present disclosure. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In another exemplary embodiment, at least one member selected from $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$ and $R^{51}$ comprises a carrier molecule. In another exemplary embodiment one of $R^1$, $R^2$, $R^3$, $R^4$, $R^5$, $R^6$, $R^7$, $R^8$, $R^9$, $R^1$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$ and $R^{51}$ comprises a carrier group bound through a substituted alkyl group or reactive group, such as an alkyl-succinamidyl group.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an antibody binding protein, a fluorescent protein, agarose, and a non-biological microparticle. Typically, the carrier molecule is an antibody, an antibody fragment, antibody-binding proteins, avidin, streptavidin, a toxin, a lectin, or a growth factor. Preferred haptens include biotin, digoxigenin and fluorescent proteins.

Antibody binding proteins include, but are not limited to, protein A, protein G, soluble Fc receptor, protein L, lectins, anti-IgG, anti-IgA, anti-IgM, anti-IgD, anti-IgE or a fragment thereof.

In an exemplary embodiment, the enzymatic substrate is selected from an amino acid, peptide, sugar, alcohol, alkanoic acid, 4-guanidinobenzoic acid, nucleic acid, lipid, sulfate, phosphate, —CH$_2$OCOalkyl and combinations thereof. Thus, the enzyme substrates can be cleaved by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL (GE Healthcare, Fairfield, Conn.), heparin, glycogen, amylopectin, mannan, inulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye compound into cells or cellular organelles.

Alternatively, the carrier molecule is cells, cellular systems, cellular fragments, or subcellular particles. Examples of this type of conjugated material include virus particles, bacterial particles, virus components, biological cells (such as animal cells, plant cells, bacteria, or yeast), or cellular components. Examples of cellular components that can be labeled, or whose constituent molecules can be labeled, include but are not limited to lysosomes, endosomes, cytoplasm, nuclei, histones, mitochondria, Golgi apparatus, endoplasmic reticulum and vacuoles.

In another embodiment the carrier molecule is a metal chelating moiety. While any chelator that binds a metal ion of interest and gives a change in its fluorescence properties is a suitable conjugate, preferred metal chelating moieties are crown ethers, including diaryldiaza crown ethers, as described in U.S. Pat. No. 5,405,975 to Kuhn et al. (1995); derivatives of 1,2-bis-(2-aminophenoxyethane)-N,N,N',N'-tetraacetic acid (BAPTA), as described in U.S. Pat. No. 5,453,517 to Kuhn et al. (1995) (incorporated by reference) and U.S. Pat. No. 5,049,673 to Tsien et al. (1991); derivatives of 2-carboxymethoxy-aniline-N,N-diacetic acid (AP-TRA), as described by Raju et al., Am. J. Physiol., 256: C540 (1989); and pyridyl-based and phenanthroline metal ion chelators, as described in U.S. Pat. No. 5,648,270 to Kuhn et al. (1997).

Aldehyde/ketone-sensing conjugates of the present disclosure are optionally prepared in chemically reactive forms and further conjugated to polymers such as dextrans to improve their utility as sensors as described in U.S. Pat. Nos. 5,405,975 and 5,453,517.

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

In an exemplary embodiment, the carrier molecule comprises a specific binding pair member wherein the present compounds are conjugated to a specific binding pair member and are used to detect an analyte in a sample. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. Exemplary binding pairs are set forth in Table 2.

TABLE 2

Representative Specific Binding Pairs

| | |
|---|---|
| antigen | antibody |
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |
| antibody | antibody-binding proteins |

*IgG is an immunoglobulin
†cDNA and cRNA are the complementary strands used for hybridization Solid Supports:

In certain embodiments, the dye compounds disclosed herein are covalently bonded to a solid support. The solid support may be attached to the dye compounds either through the fluorophore, or through a reactive group, if present, or through a carrier molecule, if present.

Solid supports suitable for use herein are typically substantially insoluble in liquid phases. Solid supports for use herein are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as SEPHAROSE (GE Healthcare, Fairfield, Conn.), poly(acrylate), polystyrene, poly(acrylamide), polyol, agarose, agar, cellulose, dextran, starch, FICOLL (GE Healthcare), heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

In certain embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the dye compounds disclosed herein. Useful reactive groups are disclosed above and are equally applicable to the solid support reactive functional groups herein.

A suitable solid phase support may be selected on the basis of desired end use and suitability for various synthetic protocols. For example, where amide bond formation is desirable to attach the dye compounds disclosed herein to the solid support, resins generally useful in peptide synthesis may be employed, such as polystyrene (e.g., PAM-resin obtained from Bachem Inc., Peninsula Laboratories, etc.), POLYHIPE resin (obtained from Aminotech, Canada), polyamide resin (obtained from Peninsula Laboratories), polystyrene resin grafted with polyethylene glycol (TENTA-GEL, Rapp Polymere, Tubingen, Germany), polydimethylacrylamide resin (available from Milligen/Biosearch, California), or PEGA beads (obtained from Polymer Laboratories).

Analytes:

Analytes of interest are preferably covalently bound to a dye compound provided herein through a hydrazinyl, hydrazide or aminooxy group on the dye compound or a reporter moiety bound to the dye compound. The analytes include: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. In another embodiment, the analyte comprises a carbonyl group. In another embodiment, the analyte comprises an aldehyde group. In another embodiment, the analyte comprises a ketone group.

In one embodiment the analyte described herein is a result of oxidative stress, such as from interaction with a superoxide, hydroxy, peroxy, alkoxy, hydroperoxy, hydrogen peroxide, hypochlorous acid, ozone, a singlet oxygen, or peroxynitrite. In another embodiment the analyte is indicative of activity or inactivity of superoxide dismutase, catalase, glutathione peroxidase or substrates relating thereto, including, vitamin A, E, ascorbate or glutathione. In another embodiment, the analyte is a biomarker for a disease such as Alzheimer's disease, Parkinson's disease, atherosclerosis, multiple sclerosis, or cancer. In certain embodiments the analyte is a result of a reactive oxygen species (ROS) pathway. In another embodiment the analyte is a product of lipid peroxidation.

In another embodiment, the sample comprises live cells, intracellular fluids, extracellular fluids, biological fluids, biological fermentation media, environmental sample, industrial samples, proteins, peptides, buffer solutions biological fluids or chemical reactors. In another embodiment, the sample comprises blood cells, immune cells, cultured cells, muscle tissue, neurons, extracellular vesicles; vascular tissue, blood fluids, saliva, urine; water, soil, waste water, sea water; pharmaceuticals, foodstuffs or beverages. In another embodiment, the sample is immobilized on a polymeric membrane, within a polymeric gel, on a microparticle, on a microarray, on a silicon chip, on a glass slide, on a microwell plate, and on a microfluidic chip.

Dye Compounds and Compositions:

Certain embodiments provide a composition comprising:
(a) an analyte; and
(b) a compound of the invention.
In said embodiments, the compound may be selected from a compound of Formula (I), Formula (II), Formula (III), Formula (IV) and Formula (V). For example, the compound may be a compound of Formula (I). For example, the compound may be a compound of Formula (II). For example, the compound may be a compound of Formula (III). For example, the compound may be a compound of Formula (IV). For example, the compound may be a compound of Formula (V).

Certain embodiments provide a composition comprising:
(a) an analyte; and
(b) a compound of Formula (I) or a tautomer or salt thereof:

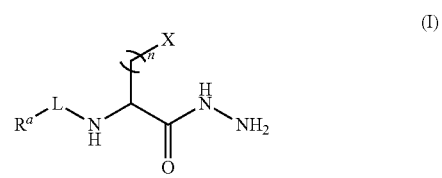

(I)

wherein,

L is a linker;

$R^a$ is a reporter molecule, carrier molecule or a solid support;

n is an integer from 1 to 24; and

X is a molecule containing $SO_3H$, $SO_3^-$, $OPO_3^{2-}$, $OPO_3H_2$, $PO_3H_2$, $PO_3^{2-}$, COOH, or $COO^-$.

In certain embodiments, L is a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is a dye. More particularly, the dye is a pyrene, a xanthene, a cyanine, an indole, a benzofuran, a coumarin, or a borapolyazaindacine.

In certain embodiments, $R^a$ is a chelating moiety, a hapten, an antibody, an enzyme, a radiolabel, a metal ion or metal ion containing substance, a pigment, a chromogen, a phosphor, a fluorogen, a bioluminescent substance, a chemiluminescent substance, or a semiconductor nanocrystal. More particularly, $R^a$ is avidin, streptavidin or an analog thereof.

In certain embodiments, $R^a$ is a solid support.

In certain embodiments, $R^a$ is a carrier molecule. More particularly, the carrier molecule is selected from the group consisting of an amino acid, a peptide, a protein, a carbohydrate, a polysaccharide, a nucleoside, a nucleotide, an oligonucleotide, a nucleic acid polymer, a drug, a lipid, and a synthetic polymer.

In certain embodiments, the compound of Formula (I) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, $R^a$ is:

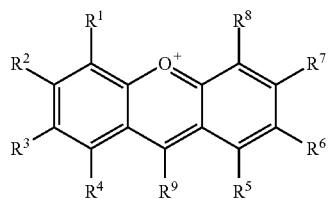

or a tautomer or salt thereof;
wherein,
$R^1$, $R^2$, $R^3$, $R^4$, $R^5$, $R^6$, $R^7$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or one or more of $R^1$ and $R^2$, $R^2$ and $R^3$, $R^3$ and $R^4$, $R^5$ and $R^6$, $R^6$ and $R^7$ or $R^7$ and $R^8$ are taken together to form a fused aryl or heteroaryl group; and
one of $R^1$, $R^2$, $R^3$, $R^4$, $R^5$, $R^6$, $R^7$, $R^8$ and $R^9$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

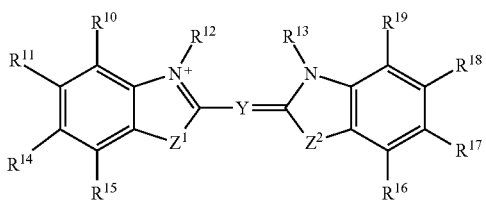

or a tautomer or salt thereof;
wherein,
$Z^1$ and $Z^2$ are each independently O, S, $NR^{23}$ or $CR^{24}R^{25}$;
Y is $-CR^{20}=(CR^{21}-CR^{22}=)_p$;
p is 0, 1, 2, or 3;
$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$, $R^{13}$ and $R^{23}$ are each independently H, alkyl, substituted alkyl, cycloalkyl, substituted cycloalkyl, aryl, substituted aryl, heteroaryl, substituted heteroaryl, heterocyclyl, substituted heterocyclyl;
$R^{20}$, $R^{21}$ and $R^{22}$ are each independently, H, alkyl, substituted alkyl, cycloalkyl, substituted cycloalkyl, aryl, substituted aryl, heteroaryl, or substituted heteroaryl;
$R^{24}$ and $R^{25}$ are H, alkyl or substituted alkyl; and
one of $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

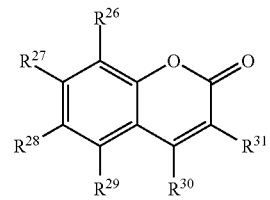

or a tautomer or salt thereof;
wherein,
$R^{26}$, $R^{27}$, $R^{28}$, $R^{29}$, $R^{30}$ and $R^{31}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
one of $R^{26}$, $R^{27}$, $R^{28}$, $R^{29}$, $R^{30}$ and $R^{31}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

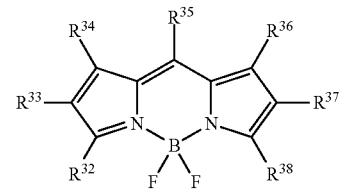

or a tautomer or salt thereof;

wherein, $R^{32}$, $R^{33}$, $R^{34}$, $R^{35}$, $R^{36}$, $R^{37}$ and $R^{38}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{32}$, $R^{33}$, $R^{34}$, $R^{35}$, $R^{36}$, $R^{37}$ and $R^{38}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

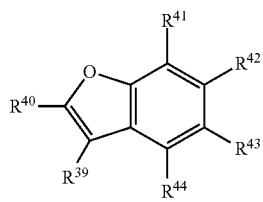

or a tautomer or salt thereof;

wherein, $R^{39}$, $R^{40}$, $R^{41}$, $R^{42}$, $R^{43}$ and $R^{44}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{39}$, $R^{40}$, $R^{41}$, $R^{42}$, $R^{43}$ and $R^{44}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

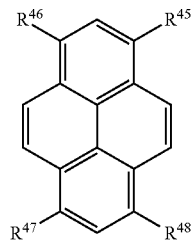

or a tautomer or salt thereof;

wherein, $R^{45}$, $R^{46}$, $R^{47}$, and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{45}$, $R^{46}$, $R^{47}$, and $R^{48}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

Certain embodiments provide a composition comprising:
(a) an analyte; and
(b) a compound of Formula (II) or a tautomer or salt thereof:

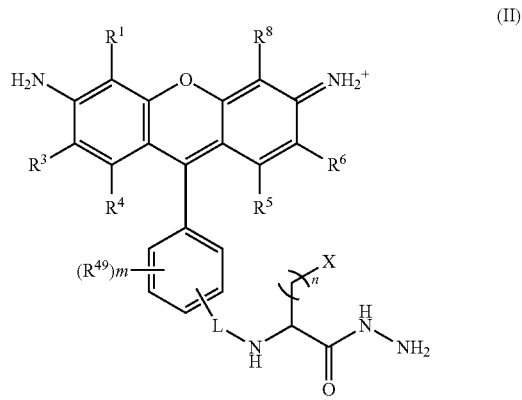

(II)

wherein,

L is a linker;

n is an integer from 1 to 24;

X is a molecule containing $SO_3H$, $SO_3^-$, $OPO_3^{2-}$, $OPO_3H_2$, $PO_3H_2$, $PO_3^{2-}$, COOH, or $COO^-$;

$R^1$, $R^3$, $R^4$, $R^5$, $R^6$, $R^8$ and $R^{49}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and m is 0, 1, or 2.

In certain embodiments, $R^1$ and $R^8$ are each sulfo; $R^2$, $R^3$, $R^4$, $R^5$, $R^6$, and $R^7$ are each H; $R^{49}$ is carboxy; m is 1; L is —C=O; X is selected from —N[(CH$_2$)$_3$SO$_3$H]$_2$, SO$_3$H, SO$_3^-$, OPO$_3^{2-}$, OPO$_3$H$_2$, PO$_3$H$_2$, PO$_3^{2-}$, COOH, and COO$^-$; and n is 1, 2, 3 or 4. In certain embodiments, the compound of Formula (II) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

Certain embodiments provide a composition comprising:
(a) an analyte; and
(b) a compound of Formula (III) or a tautomer or salt thereof:

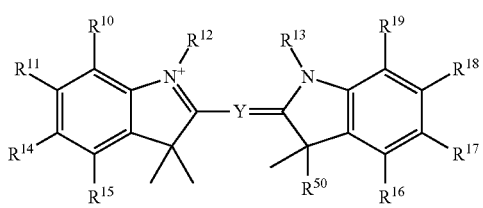

(III)

wherein,
Y is —CR$^{20}$=(CR$^{21}$—CR$^{22}$=)$_p$;
p is 0, 1, 2, or 3;
$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$ and $R^{13}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{50}$ is alkyl; and wherein one of $R^{13}$ or $R^{50}$ is:

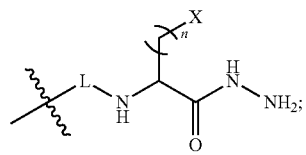

L is a linker;
n is an integer from 1 to 24; and
X is a molecule containing SO$_3$H, SO$_3^-$, OPO$_3^{2-}$, OPO$_3$H$_2$, PO$_3$H$_2$, PO$_3^{2-}$, COOH, or COO$^-$ In certain embodiments, $R^{50}$ is methyl. In certain embodiments, the compound of Formula (III) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

Certain embodiments provide a composition comprising:
(a) an analyte; and
(b) a compound of Formula (IV) or a tautomer or salt thereof:

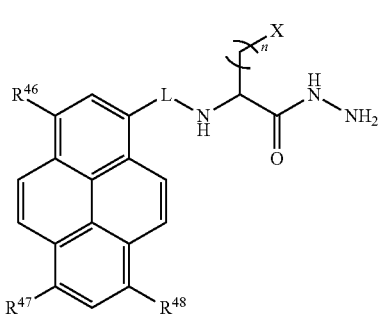

(IV)

wherein,
L is a linker;
n is an integer from 1 to 24;
X is a molecule containing SO$_3$H, SO$_3^-$, OPO$_3^{2-}$, OPO$_3$H$_2$, PO$_3$H$_2$, PO$_3^{2-}$, COOH, or COO$^-$; and
$R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl.

In certain embodiments, $R^{46}$, $R^{47}$, and $R^{48}$ are each sulfo; X is carboxy; n is 1 or 2; and L is

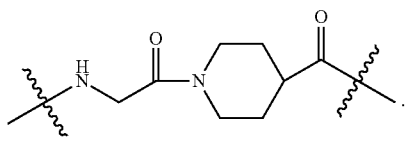 [SMILES: *NCC(=O)N1CCC(C(*)=O)CC1]

In certain embodiments, the compound of Formula (IV) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

Certain embodiments provide a composition comprising:
(a) an analyte; and
(b) a compound of Formula (V) or a tautomer or salt thereof:

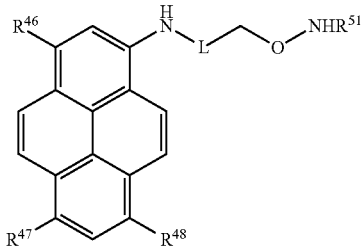
(V)

wherein,
L is a linker;
$R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
$R^{51}$ is selected from H, alkyl and substituted alkyl.

In certain embodiments, $R^{46}$, $R^{47}$, and $R^{48}$ are each sulfo, $R^{51}$ is H, and L is selected from the group consisting of: —(CH$_2$)$_5$C(O)NH(CH$_2$)$_2$—, —(CH$_2$)$_6$NHC(O)— and —C(O)—. In certain embodiments, the compound of Formula (V) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

Certain embodiments provide a composition comprising:
(a) an analyte; and
(b) a compound selected from the group consisting of:

Compound 1

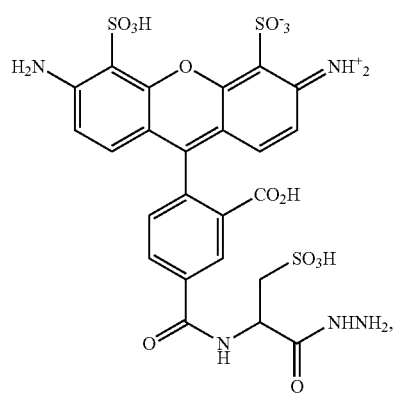

Compound 2

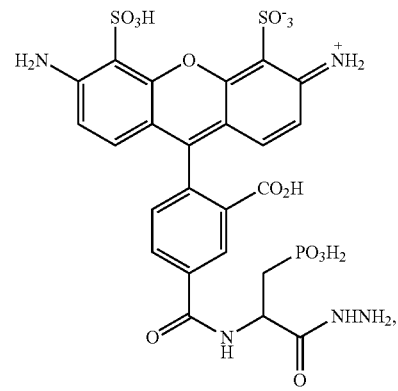

Compound 4

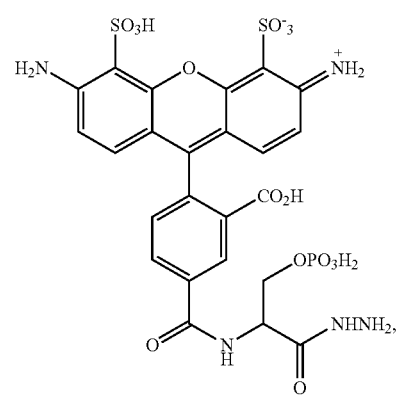

Compound 5

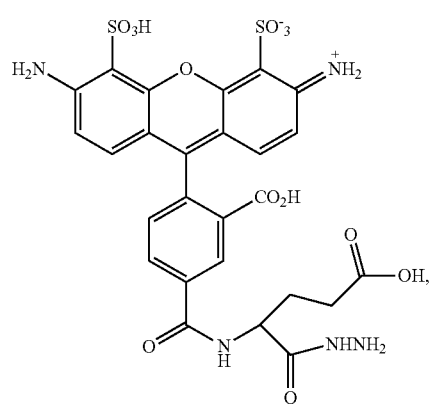

Compound 6

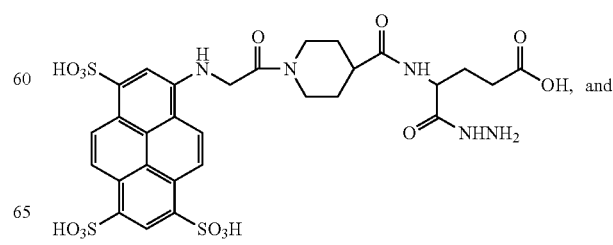

-continued

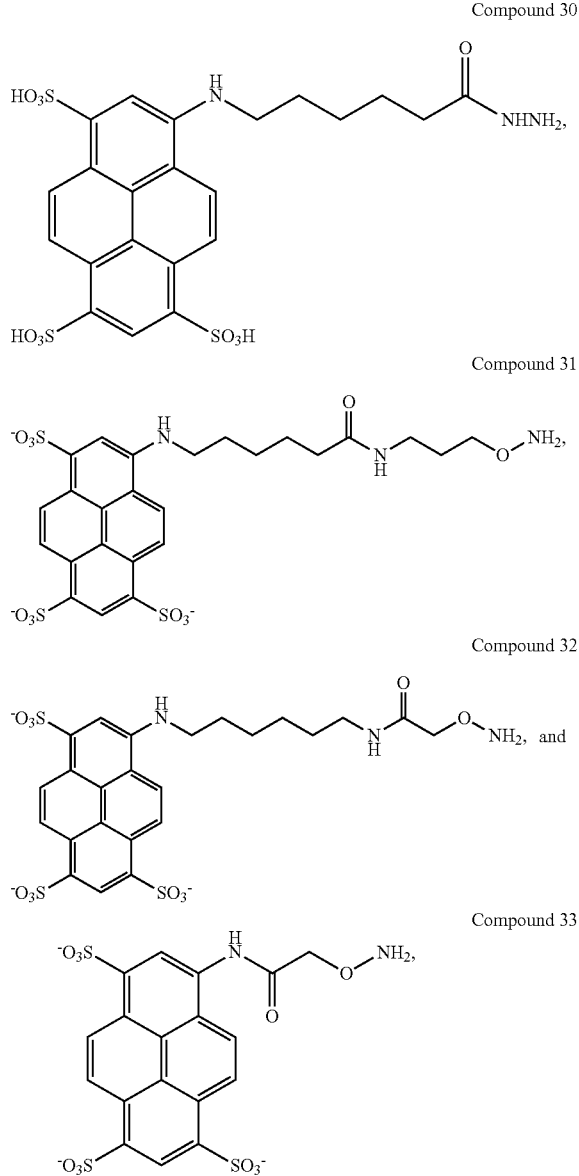

Compound 30

Compound 31

Compound 32

Compound 33 or a salt thereof.

In certain embodiments, the compound is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, the composition further comprises a buffer solution. In certain embodiments, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus.

Methods:

In certain embodiments, a method for determining the presence of an analyte of interest in a sample is provided, the method comprising:

a) contacting the sample with a compound of the invention or a tautomer or salt thereof;

b) incubating the sample and the compound for a sufficient amount of time to form a complex between the compound and analyte;

c) illuminating the complex with an appropriate wavelength to form an illuminated complex; and d) detecting emissions from the illuminated complex, thereby determining the presence of the analyte in the sample.

In certain embodiments, the analyte is a glycan. In certain embodiments, the glycan is cleaved from a biomolecule. In certain embodiments, the analyte and the compound are connected by a covalent bond. In certain embodiments, the analyte is bound to the compound through an imine. In certain embodiments, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. In certain embodiments, the analyte comprises an aldehyde. In certain embodiments, the analyte comprises a carbonyl group. More particularly, the analyte comprises a ketone group or an aldehyde group.

In certain embodiments, the sample comprises live cells, intracellular fluids, extracellular fluids, biological fluids, biological fermentation media, environmental sample, industrial samples, proteins, peptides, buffer solutions biological fluids or chemical reactors. More particularly, the sample comprises blood cells, immune cells, cultured cells, muscle tissue, neurons, extracellular vesicles; vascular tissue, blood fluids, saliva, urine; water, soil, waste water, sea water; pharmaceuticals, foodstuffs or beverages. In certain embodiments, the sample is immobilized on a polymeric membrane, within a polymeric gel, on a microparticle, on a microarray, on a silicon chip, on a glass slide, on a microwell plate, and on a microfluidic chip.

In certain embodiments, a method for determining the presence of an analyte of interest in a sample is provided, the method comprising:

a) contacting the sample with a compound having Formula (I) or a tautomer or salt thereof:

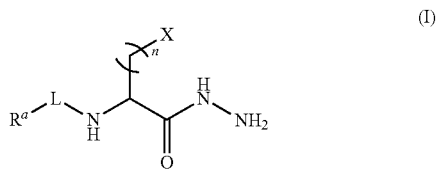

(I)

wherein,

L is a linker;

$R^a$ is a reporter molecule, carrier molecule or a solid support;

n is an integer from 1 to 24; and

X is a molecule containing $SO_3H$, $SO_3^-$, $OPO_3^{2-}$, $OPO_3H_2$, $PO_3H_2$, $PO_3^{2-}$, COOH, or $COO^-$;

b) incubating the sample and the compound for a sufficient amount of time to form a complex between the compound and analyte;

c) illuminating the complex with an appropriate wavelength to form an illuminated complex; and d) detecting emissions from the illuminated complex, thereby determining the presence of the analyte in the sample.

In certain embodiments, the analyte is a glycan. In certain embodiments, the analyte and the compound are connected by a covalent bond. In certain embodiments, the analyte is bound to the compound through an imine. In certain embodiments, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. In certain embodiments, the analyte comprises an aldehyde. In certain embodiments, the analyte comprises a carbonyl group. More particularly, the analyte comprises a ketone group or an aldehyde group.

In certain embodiments, L is a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is a dye. More particularly, the dye is a pyrene, a xanthene, a cyanine, an indole, a benzofuran, a coumarin, or a borapolyazaindacene.

In certain embodiments, $R^a$ is a chelating moiety, a hapten, an antibody, an enzyme, a radiolabel, a metal ion or metal ion containing substance, a pigment, a chromogen, a phosphor, a fluorogen, a bioluminescent substance, a chemiluminescent substance, or a semiconductor nanocrystal. More particularly, $R^a$ is avidin, streptavidin or an analog thereof.

In certain embodiments, $R^a$ is a solid support.

In certain embodiments, $R^a$ is a carrier molecule. More particularly, the carrier molecule is selected from the group consisting of an amino acid, a peptide, a protein, a carbohydrate, a polysaccharide, a nucleoside, a nucleotide, an oligonucleotide, a nucleic acid polymer, a drug, a lipid, and a synthetic polymer.

In certain embodiments, the compound of Formula (I) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, $R^a$ is:

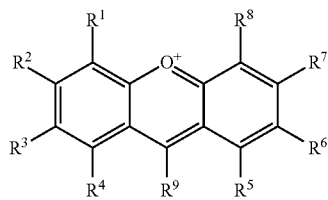

or a tautomer or salt thereof;
wherein,
$R^1$, $R^2$, $R^3$, $R^4$, $R^5$, $R^6$, $R^7$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or one or more of $R^1$ and $R^2$, $R^2$ and $R^3$, $R^3$ and $R^4$, $R^5$ and $R^6$, $R^6$ and $R^7$ or $R^7$ and $R^8$ are taken together to form a fused aryl or heteroaryl group; and one of $R^1$, $R^2$, $R^3$, $R^4$, $R^5$, $R^6$, $R^7$, $R^8$ and $R^9$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

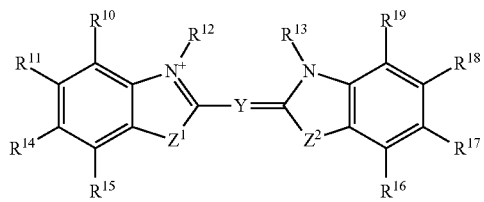

or a tautomer or salt thereof;
wherein,
$Z^1$ and $Z^2$ are each independently O, S, $NR^{23}$ or $CR^{24}R^{25}$;
Y is $-CR^{20}=(CR^{21}-CR^{22}=)_p$;
p is 0, 1, 2, or 3;
$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$, $R^{13}$ and $R^{23}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{20}$, $R^{21}$ and $R^{22}$ are each independently, H, alkyl, substituted alkyl, cycloalkyl, substituted cycloalkyl, aryl, substituted aryl, heteroaryl, or substituted heteroaryl;

$R^{24}$ and $R^{25}$ are H, alkyl or substituted alkyl; and one of $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

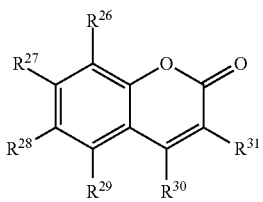

or a tautomer or salt thereof;
wherein,
$R^{26}$, $R^{27}$, $R^{28}$, $R^{29}$, $R^{30}$ and $R^{31}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
one of $R^{26}$, $R^{27}$, $R^{28}$, $R^{29}$, $R^{30}$ and $R^{31}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

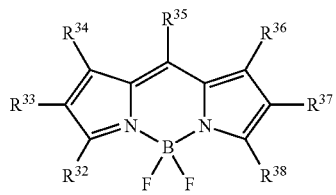

or a tautomer or salt thereof;
wherein,
$R^{32}$, $R^{33}$, $R^{34}$, $R^{35}$, $R^{36}$, $R^{37}$ and $R^{38}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
one of $R^{32}$, $R^{33}$, $R^{34}$, $R^{35}$, $R^{36}$, $R^{37}$ and $R^{38}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

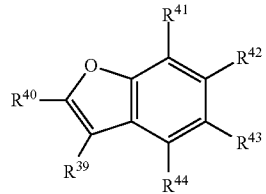

or a tautomer or salt thereof;
wherein,
$R^{39}$, $R^{40}$, $R^{41}$, $R^{42}$, $R^{43}$ and $R^{44}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
one of $R^{39}$, $R^{40}$, $R^{41}$, $R^{42}$, $R^{43}$ and $R^{44}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

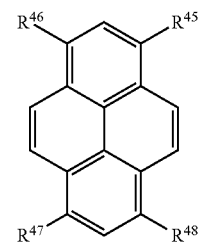

or a tautomer or salt thereof;
wherein,
$R^{45}$, $R^{46}$, $R^{47}$, and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{45}$, $R^{46}$, $R^{47}$, and $R^{48}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, a method for determining the presence of an analyte of interest in a sample is provided, the method comprising:

a) contacting the sample with a compound having Formula (II) or a tautomer or salt thereof:

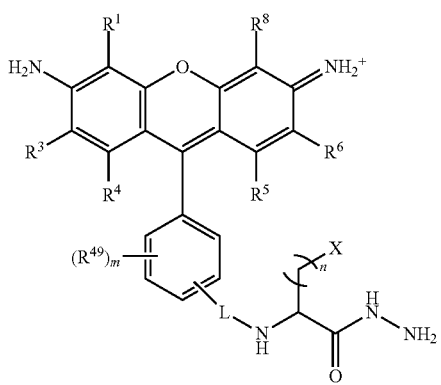

(II)

wherein,

L is a linker;

n is an integer from 1 to 24;

X is a molecule containing $SO_3H$, $SO_3^-$, $OPO_3^{2-}$, $OPO_3H_2$, $PO_3H_2$, $PO_3^{2-}$, COOH, or $COO^-$;

$R^1$, $R^3$, $R^4$, $R^5$, $R^6$, $R^8$ and $R^{49}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and m is 0, 1, or 2;

b) incubating the sample and the compound for a sufficient amount of time to form a complex between the compound and analyte;

c) illuminating the complex with an appropriate wavelength to form an illuminated complex; and d) detecting emissions from the illuminated complex, thereby determining the presence of the analyte in the sample.

In certain embodiments, the analyte is a glycan. In certain embodiments, the glycan is cleaved from a biomolecule. In certain embodiments, the analyte and the compound are connected by a covalent bond. In certain embodiments, the analyte is bound to the compound through an imine. In certain embodiments, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. In certain embodiments, the analyte comprises an aldehyde. In certain embodiments, the analyte comprises a carbonyl group. More particularly, the analyte comprises a ketone group or an aldehyde group.

In certain embodiments, $R^1$ and $R^8$ are each sulfo; $R^2$, $R^3$, $R^4$, $R^5$, $R^6$, and $R^7$ are each H; $R^{49}$ is carboxy; m is 1; L is $-C=O$; X is selected from $N[(CH_2)_3SO_3H]_2$, $SO_3H$, $SO_3^-$, $OPO_3^{2-}$, $OPO_3H_2$, $PO_3H_2$, $PO_3^{2-}$, COOH, and $COO^-$; and n is 1, 2, 3 or 4. In certain embodiments, the compound of Formula (II) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a method for determining the presence of an analyte of interest in a sample is provided, the method comprising:

a) contacting the sample with a compound having Formula (III) or a tautomer or salt thereof:

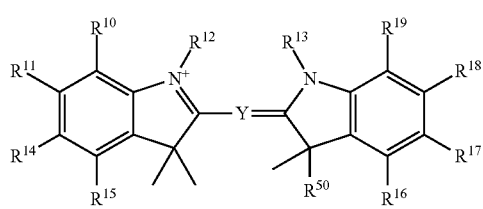

(III)

wherein,

Y is $-CR^{20}=(CR^{21}-CR^{22}=)_p$;

p is 0, 1, 2, or 3;

$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$ and $R^{13}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{50}$ is alkyl; and wherein one of $R^{13}$ or $R^{50}$ is:

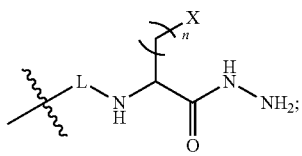

L is a linker;
n is an integer from 1 to 24; and
X is a molecule containing $SO_3H$, $SO_3^-$, $OPO_3^{2-}$, $OPO_3H_2$, $PO_3H_2$, $PO_3^{2-}$, COOH, or $COO^-$;
b) incubating the sample and the compound for a sufficient amount of time to form a complex between the compound and analyte;
c) illuminating the complex with an appropriate wavelength to form an illuminated complex; and
d) detecting emissions from the illuminated complex, thereby determining the presence of the analyte in the sample.

In certain embodiments, the analyte is a glycan. In certain embodiments, the glycan is cleaved from a biomolecule. In certain embodiments, the analyte and the compound are connected by a covalent bond. In certain embodiments, the analyte is bound to the compound through an imine. In certain embodiments, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. In certain embodiments, the analyte comprises an aldehyde. In certain embodiments, the analyte comprises a carbonyl group. More particularly, the analyte comprises a ketone group or an aldehyde group.

In certain embodiments, $R^{50}$ is methyl. In certain embodiments, the compound of Formula (III) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a method for determining the presence of an analyte of interest in a sample is provided, the method comprising:
a) contacting the sample with a compound having Formula (IV) or a tautomer or salt thereof:

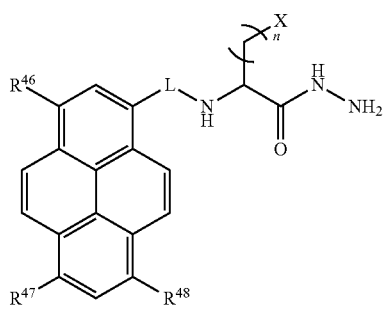

(IV)

wherein,
L is a linker;
n is an integer from 1 to 24;

X is a molecule containing $SO_3H$, $SO_3^-$, $OPO_3^{2-}$, $OPO_3H_2$, $PO_3H_2$, $PO_3^{2-}$, COOH, or $COO^-$; and
$R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

b) incubating the sample and the compound for a sufficient amount of time to form a complex between the compound and analyte;
c) illuminating the complex with an appropriate wavelength to form an illuminated complex; and
d) detecting emissions from the illuminated complex, thereby determining the presence of the analyte in the sample.

In certain embodiments, the analyte is a glycan. In certain embodiments, the glycan is cleaved from a biomolecule. In certain embodiments, the analyte and the compound are connected by a covalent bond. In certain embodiments, the analyte is bound to the compound through an imine. In certain embodiments, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. In certain embodiments, the analyte comprises an aldehyde. In certain embodiments, the analyte comprises a carbonyl group. More particularly, the analyte comprises a ketone group or an aldehyde group.

In certain embodiments, $R^{46}$, $R^{47}$, and $R^{48}$ are each sulfo; X is carboxy; n is 1 or 2; and L is

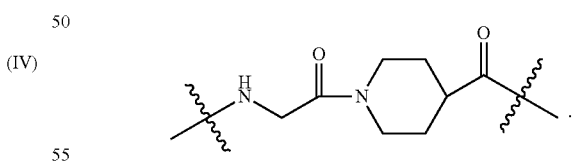

In certain embodiments, the compound of Formula (IV) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a method for determining the presence of an analyte of interest in a sample is provided, the method comprising:
a) contacting the sample with a compound having Formula (V) or a tautomer or salt thereof:

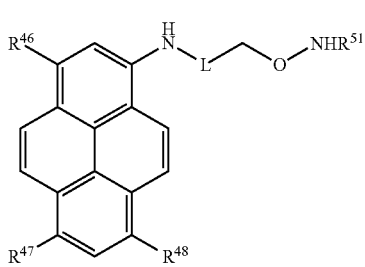

(V)

wherein,

L is a linker;

R⁴⁶, R⁴⁷ and R⁴⁸ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and R⁵¹ is selected from H, alkyl and substituted alkyl;

b) incubating the sample and the compound for a sufficient amount of time to form a complex between the compound and analyte;

c) illuminating the complex with an appropriate wavelength to form an illuminated complex; and d) detecting emissions from the illuminated complex, thereby determining the presence of the analyte in the sample.

In certain embodiments, the analyte is a glycan. In certain embodiments, the glycan is cleaved from a biomolecule. In certain embodiments, the analyte and the compound are connected by a covalent bond. In certain embodiments, the analyte is bound to the compound through an oxime. In certain embodiments, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. In certain embodiments, the analyte comprises an aldehyde. In certain embodiments, the analyte comprises a carbonyl group. More particularly, the analyte comprises a ketone group or an aldehyde group.

In certain embodiments, R⁴⁶, R⁴⁷, and R⁴⁸ are each sulfo, R⁵¹ is H, and L is selected from the group consisting of: —(CH₂)₅C(O)NH(CH₂)₂—, —(CH₂)₆NHC(O)— and —C(O)—. In certain embodiments, the compound of Formula (V) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a method for determining the presence of an analyte of interest in a sample is provided, the method comprising:

a) contacting the sample with a compound selected from the group consisting of:

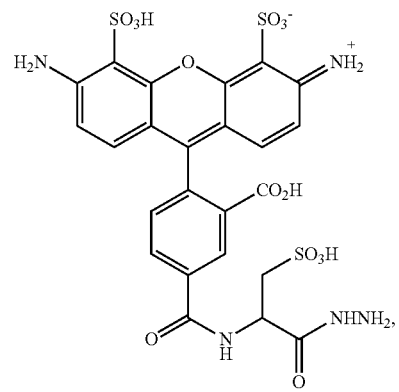

Compound 1

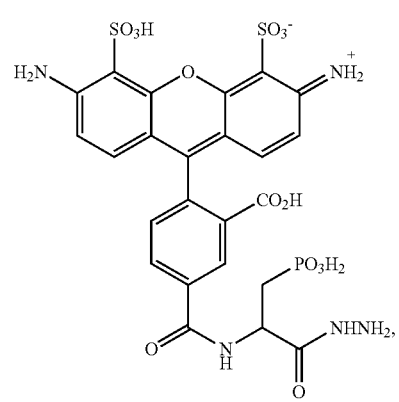

Compound 2

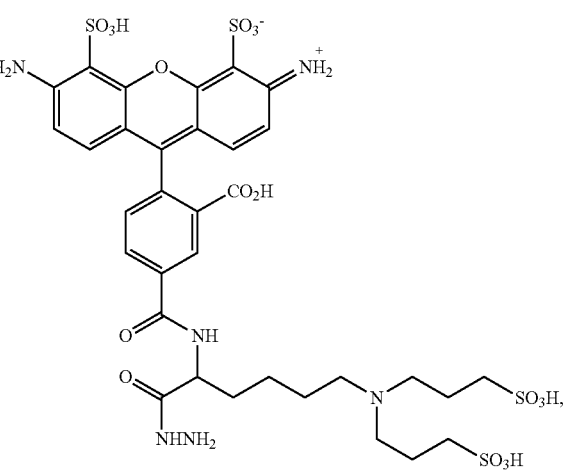

Compound 3

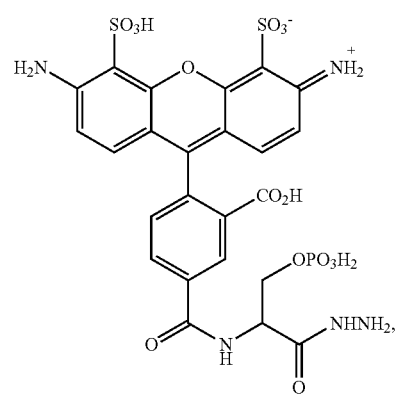

Compound 4

-continued

Compound 5

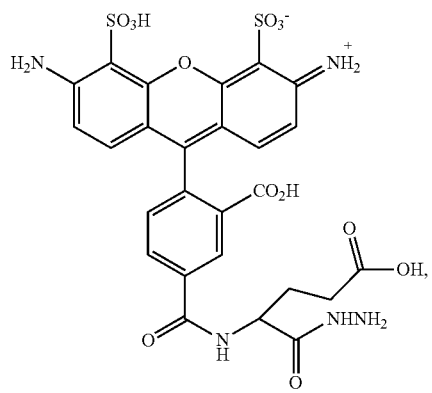

Compound 6

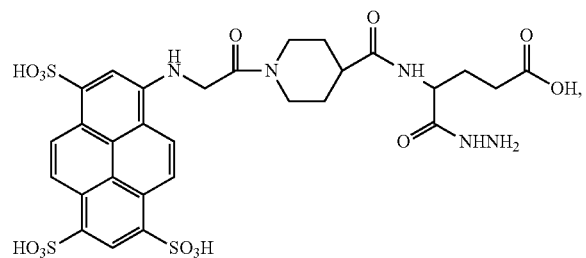

Compound 30

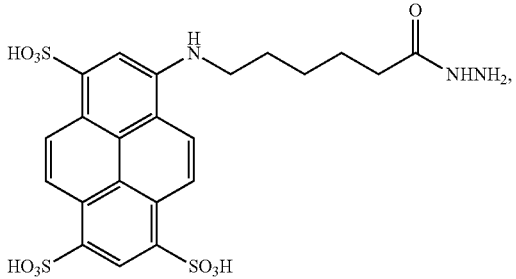

Compound 31

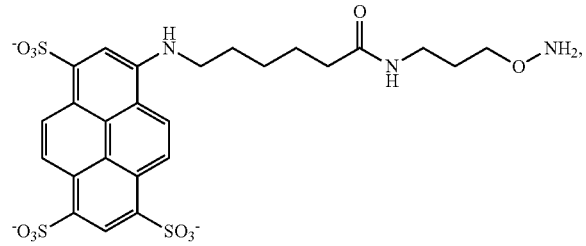

Compound 32

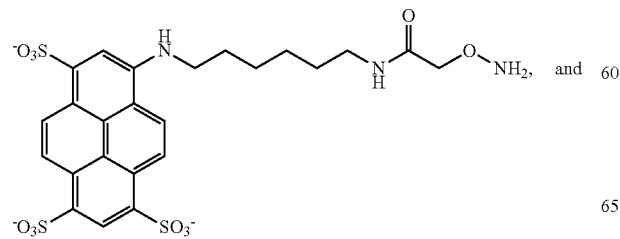

and

-continued

Compound 33

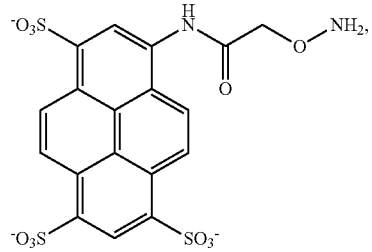

or a salt thereof;
b) incubating the sample and the compound for a sufficient amount of time to form a complex between the compound and analyte;
c) illuminating the complex with an appropriate wavelength to form an illuminated complex; and
d) detecting emissions from the illuminated complex, thereby determining the presence of the analyte in the sample.

In certain embodiments, the compound is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, the analyte is a glycan. In certain embodiments, the glycan is cleaved from a biomolecule. In certain embodiments, the analyte and the compound are connected by a covalent bond. In certain embodiments, the analyte is selected from the group consisting of an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. More particularly, the analyte comprises a ketone group or an aldehyde group.

In certain embodiments, the sample comprises live cells, intracellular fluids, extracellular fluids, biological fluids, biological fermentation media, environmental sample, industrial samples, proteins, peptides, buffer solutions biological fluids or chemical reactors. More particularly, the sample comprises blood cells, immune cells, cultured cells, muscle tissue, neurons, extracellular vesicles; vascular tissue, blood fluids, saliva, urine; water, soil, waste water, sea water; pharmaceuticals, foodstuffs or beverages. In certain embodiments, the sample is immobilized on a polymeric membrane, within a polymeric gel, on a microparticle, on a microarray, on a silicon chip, on a glass slide, on a microwell plate, and on a microfluidic chip.

In certain embodiments, a method for determining the presence of one or more glycans in a sample is provided, the method comprising:
a) contacting the sample with a compound of the invention or a tautomer or salt thereof;
b) incubating the sample and the compound for a sufficient amount of time to form a complex between the compound and the one or more glycans;
c) separating the sample using electrophoresis or chromatography, thereby determining the presence of the one or more glycans in the sample.

In certain embodiments, the glycan and the compound are connected by a covalent bond.

In certain embodiments, a method for determining the presence of one or more glycans in a sample is provided, the method comprising:

a) contacting the sample with a compound having Formula (I) or a tautomer or salt thereof:

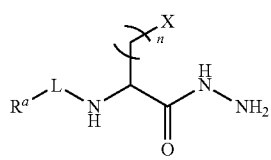

(I)

wherein,

L is a linker;

$R^a$ is a reporter molecule, carrier molecule or a solid support;

n is an integer from 1 to 24; and

X is a molecule containing $SO_3H$, $SO_3^-$, $OPO_3^{2-}$, $OPO_3H_2$, $PO_3H_2$, $PO_3^{2-}$, COOH, or $COO^-$;

b) incubating the sample and the compound for a sufficient amount of time to form a complex between the compound and the one or more glycans;

c) separating the sample using electrophoresis or chromatography, thereby determining the presence of the one or more glycans in the sample.

In certain embodiments, the glycan and the compound are connected by a covalent bond.

In certain embodiments, L is a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is a dye. More particularly, the dye is a pyrene, a xanthene, a cyanine, an indole, a benzofuran, a coumarin, or a borapolyazaindacine.

In certain embodiments, $R^a$ is a chelating moiety, a hapten, an antibody, an enzyme, a radiolabel, a metal ion or metal ion containing substance, a pigment, a chromogen, a phosphor, a fluorogen, a bioluminescent substance, a chemiluminescent substance, or a semiconductor nanocrystal. More particularly, $R^a$ is avidin, streptavidin or an analog thereof.

In certain embodiments, $R^a$ is a solid support.

In certain embodiments, $R^a$ is a carrier molecule. More particularly, the carrier molecule is selected from the group consisting of an amino acid, a peptide, a protein, a carbohydrate, a polysaccharide, a nucleoside, a nucleotide, an oligonucleotide, a nucleic acid polymer, a drug, a lipid, and a synthetic polymer.

In certain embodiments, the compound of Formula (I) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, $R^a$ is:

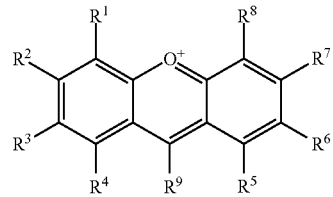

or a tautomer or salt thereof;

wherein, $R^1$, $R^2$, $R^3$, $R^4$, $R^5$, $R^6$, $R^7$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or one or more of $R^1$ and $R^2$, $R^2$ and $R^3$, $R^3$ and $R^4$, $R^5$ and $R^6$, $R^6$ and $R^7$ or $R^7$ and $R^8$ are taken together to form a fused aryl or heteroaryl group; and one of $R^1$, $R^2$, $R^3$, $R^4$, $R^5$, $R^6$, $R^7$, $R^8$ and $R^9$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

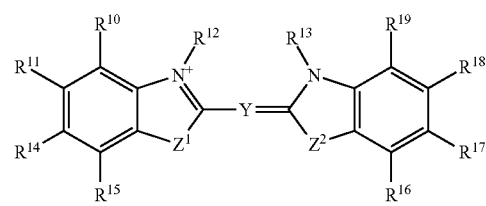

or a tautomer or salt thereof;

wherein, $Z^1$ and $Z^2$ are each independently O, S, $NR^{23}$ or $CR^{24}R^{25}$;

Y is $-CR^{20}=(CR^{21}-CR^{22}=)_p$;

p is 0, 1, 2, or 3;

$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$, $R^{13}$ and $R^{23}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{20}$, $R^{21}$ and $R^{22}$ are each independently, H, alkyl, substituted alkyl, cycloalkyl, substituted cycloalkyl, aryl, substituted aryl, heteroaryl, or substituted heteroaryl;

$R^{24}$ and $R^{25}$ are H, alkyl or substituted alkyl; and one of $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

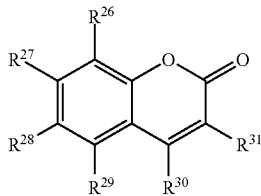

or a tautomer or salt thereof;
wherein, $R^{26}$, $R^{27}$, $R^{28}$, $R^{29}$, $R^{30}$ and $R^{31}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{26}$, $R^{27}$, $R^{28}$, $R^{29}$, $R^{30}$ and $R^{31}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

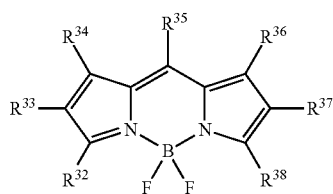

or a tautomer or salt thereof;

wherein, $R^{32}$, $R^{33}$, $R^{34}$, $R^{35}$, $R^{36}$, $R^{37}$ and $R^{38}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{32}$, $R^{33}$, $R^{34}$, $R^{35}$, $R^{36}$, $R^{37}$ and $R^{38}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

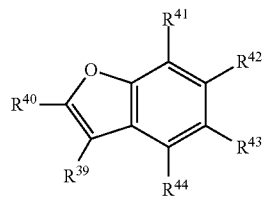

or a tautomer or salt thereof;
wherein, $R^{39}$, $R^{40}$, $R^{41}$, $R^{42}$, $R^{43}$ and $R^{44}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{39}$, $R^{40}$, $R^{41}$, $R^{42}$, $R^{43}$ and $R^{44}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

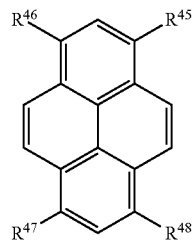

or a tautomer or salt thereof;
wherein,
$R^{45}$, $R^{46}$, $R^{47}$, and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
one of $R^{45}$, $R^{46}$, $R^{47}$, and $R^{48}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, a method for determining the presence of one or more glycans in a sample is provided, the method comprising:
a) contacting the sample with a compound having Formula (II) or a tautomer or salt thereof:

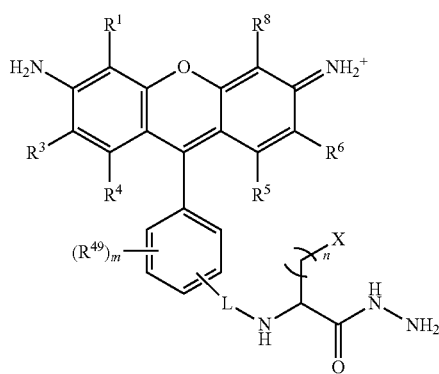

(II)

wherein,
L is a linker;
n is an integer from 1 to 24;

X is a molecule containing $SO_3H$, $SO_3^-$, $OPO_3^{2-}$, $OPO_3H_2$, $PO_3H_2$, $PO_3^{2-}$, COOH, or $COO^-$;
$R^1$, $R^3$, $R^4$, $R^5$, $R^6$, $R^8$ and $R^{49}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
m is 0, 1, or 2;
b) incubating the sample and the compound for a sufficient amount of time to form a complex between the compound and the one or more glycans;
c) separating the sample using electrophoresis or chromatography, thereby determining the presence of the one or more glycans in the sample.

In certain embodiments, the glycan and the compound are connected by a covalent bond.

In certain embodiments, $R^1$ and $R^8$ are each sulfo; $R^2$, $R^3$, $R^4$, $R^5$, $R^6$, and $R^7$ are each H; $R^{49}$ is carboxy; m is 1; L is —C═O; X is selected from $N[(CH_2)_3SO_3H]_2$, $SO_3H$, $SO_3^-$, $OPO_3^{2-}$, $OPO_3H_2$, $PO_3H_2$, $PO_3^{2-}$, COOH, and $COO^-$; and n is 1, 2, 3 or 4. In certain embodiments, the compound of Formula (II) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a method for determining the presence of one or more glycans in a sample is provided, the method comprising:
a) contacting the sample with a compound having Formula (III) or a tautomer or salt thereof:

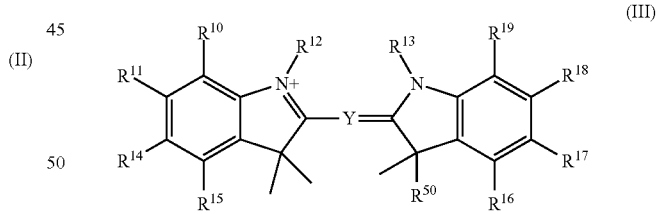

(III)

wherein,
Y is $-CR^{20}=(CR^{21}-CR^{22}=)_p$;
p is 0, 1, 2, or 3;
$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$ and $R^{13}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{50}$ is alkyl; and wherein one of $R^{13}$ or $R^{50}$ is:

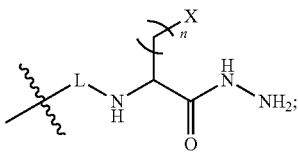

L is a linker;

n is an integer from 1 to 24; and

X is a molecule containing $SO_3H$, $SO_3^-$, $OPO_3^{2-}$, $OPO_3H_2$, $PO_3H_2$, $PO_3^{2-}$, COOH, or $COO^-$;

b) incubating the sample and the compound for a sufficient amount of time to form a complex between the compound and the one or more glycans;

c) separating the sample using electrophoresis or chromatography, thereby determining the presence of the one or more glycans in the sample.

In certain embodiments, the glycan and the compound are connected by a covalent bond.

In certain embodiments, $R^{50}$ is methyl. In certain embodiments, the compound of Formula (III) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a method for determining the presence of one or more glycans in a sample is provided, the method comprising:

a) contacting the sample with a compound having Formula (IV) or a tautomer or salt thereof:

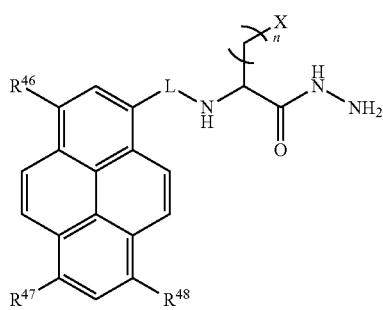

(IV)

wherein,

L is a linker;

n is an integer from 1 to 24;

X is a molecule containing $SO_3H$, $SO_3^-$, $OPO_3^{2-}$, $OPO_3H_2$, $PO_3H_2$, $PO_3^{2-}$, COOH, or $COO^-$; and $R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

b) incubating the sample and the compound for a sufficient amount of time to form a complex between the compound and the one or more glycans;

c) separating the sample using electrophoresis or chromatography, thereby determining the presence of the one or more glycans in the sample.

In certain embodiments, the glycan and the compound are connected by a covalent bond.

In certain embodiments, $R^{46}$, $R^{47}$, and $R^{48}$ are each sulfo; X is carboxy; n is 1 or 2; and L is

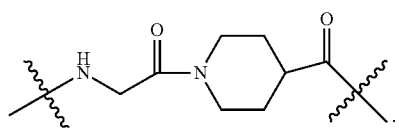 [SMILES: *NCC(=O)N1CCC(C(*)=O)CC1]

In certain embodiments, the compound of Formula (IV) is a salt.

More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a method for determining the presence of one or more glycans in a sample is provided, the method comprising:

a) contacting the sample with a compound having Formula (V) or a tautomer or salt thereof:

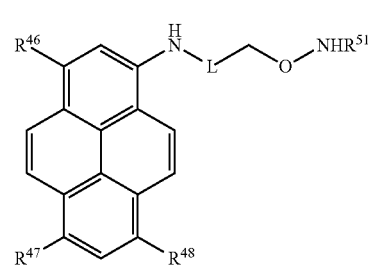

(V)

wherein,

L is a linker;

$R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^{51}$ is selected from H, alkyl and substituted alkyl;

b) incubating the sample and the compound for a sufficient amount of time to form a complex between the compound and the one or more glycans;

c) separating the sample using electrophoresis or chromatography, thereby determining the presence of the one or more glycans in the sample.

In certain embodiments, $R^{46}$, $R^{47}$, and $R^{46}$ are each sulfo, $R^{51}$ is H, and L is selected from the group consisting of: —(CH$_2$)$_5$C(O)NH(CH$_2$)$_2$—, —(CH$_2$)$_6$NHC(O)— and —C(O)—. In certain embodiments, the compound of Formula (V) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, the glycan and the compound are connected by a covalent bond.

In certain embodiments, a method for determining the presence of one or more glycans in a sample is provided, the method comprising:

a) contacting the sample with a compound selected from the group consisting of:

Compound 1

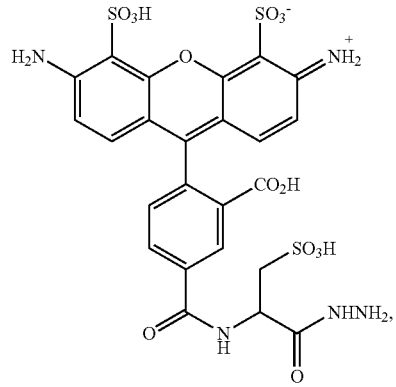

Compound 2

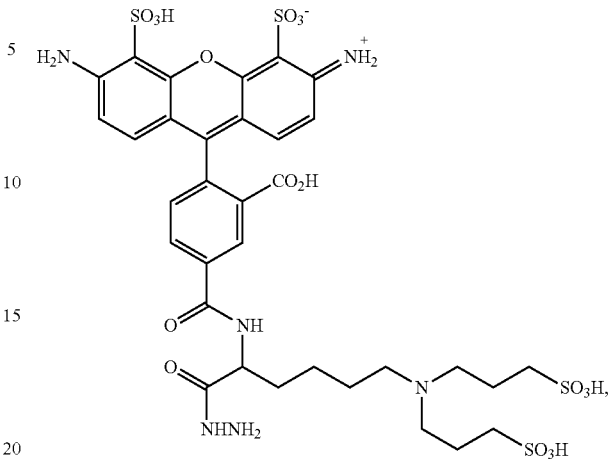

Compound 3

Compound 4

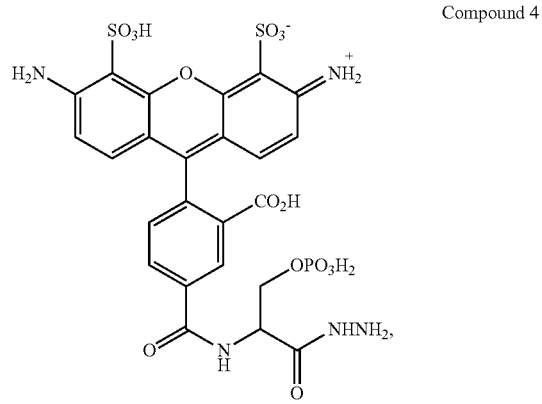

Compound 5

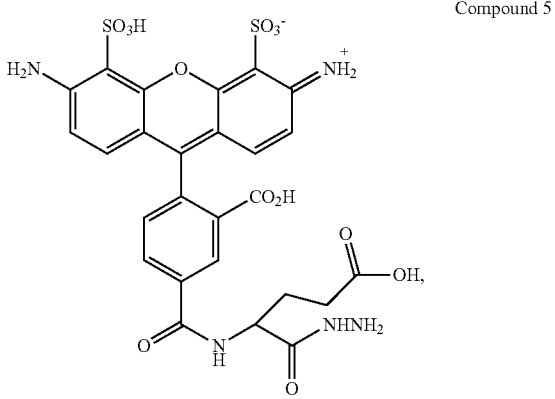

Compound 6

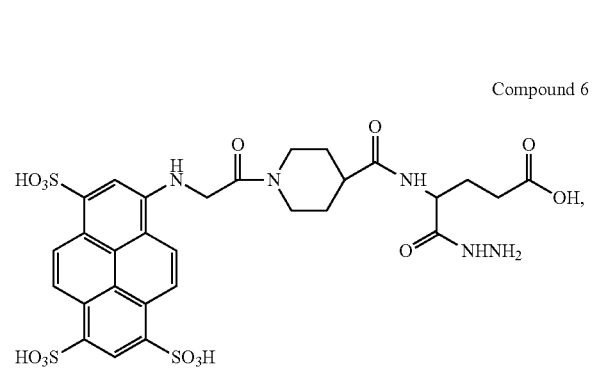

-continued

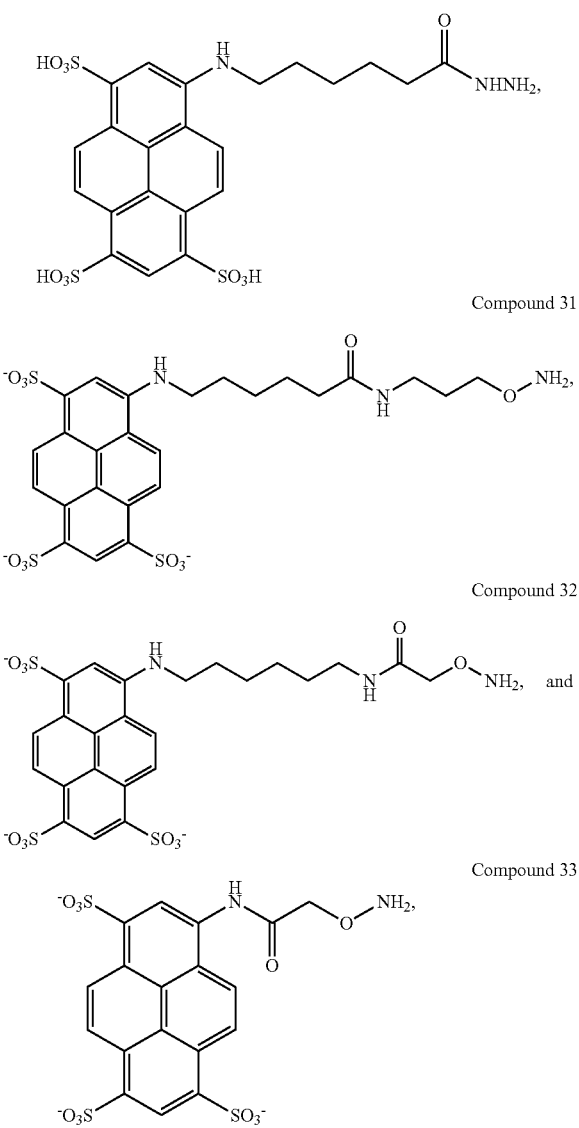

Compound 30

Compound 31

Compound 32

Compound 33 or a salt thereof;
b) incubating the sample and the compound for a sufficient amount of time to form a complex between the compound and the one or more glycans;
c) separating the sample using electrophoresis or chromatography, thereby determining the presence of the one or more glycans in the sample.

In certain embodiments, the compound is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion. In certain embodiments, the glycan and the compound are connected by a covalent bond.

In certain embodiments, dyes other than the hydrazinyl dye compounds and aminooxy dye compounds provided herein may be used. As used herein, the dye may be a visible dye, a fluorescent dye, or a chemiluminescent dye. In various embodiments, the fluorescent dye may be a pyrene dye, a naphthalene dye, an aminopyridine dye, a xanthene dye which may be a fluorescein, rhodol or rhodamine dye, a cyanine dye, a coumarin dye, a borapolyazaindacine dye, a benzofuran dye, or an indole dye. In some embodiments, the fluorescent dye may be aminopyrene trisulfonic acid (APTS). In certain embodiments, the APTS dye may be selected from those described in co-owned, co-pending U.S. Provisional Patent Application Ser. No. 62/087,208, titled "Charged Reactive Oligomers" and PCT Patent Application titled "Charged Reactive Oligomers, each of which is herein incorporated by reference in its entirety, including, but not limited to:

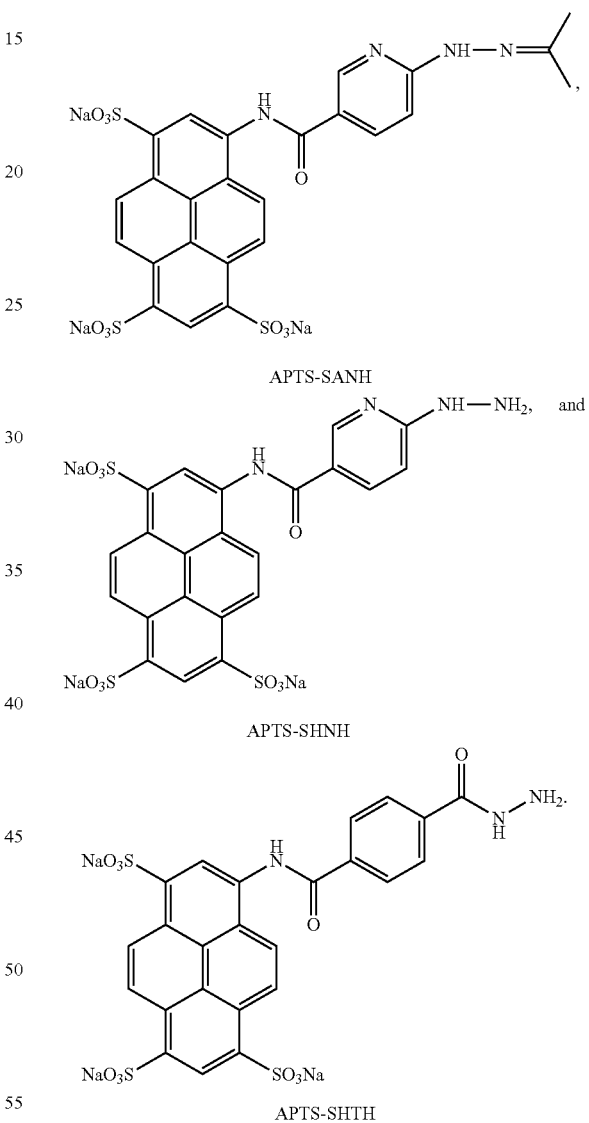

APTS-SANH

APTS-SHNH

APTS-SHTH

In other embodiments, the fluorescent dye may be a fluorescein dye or a rhodamine dye. In various embodiments, more than one dye may be incorporated in the labeling species. When more than one dye may be incorporated in the labeling species, the fluorescent dye may be a polymeric dye or an energy transfer dye. An energy transfer dye may have a donor dye and an acceptor dye, where the donor dye may be configured to absorb energy at one wavelength and emit energy at a second wavelength which emitted energy excites the acceptor dye at the second wavelength. The acceptor dye then emits at a third wavelength, which may be detectable. If more than one labeling species may be used in a glycan detection assay where more than one energy transfer dye may be used to label various different glycans, then the more than one energy transfer dye are configured to be detected at different wavelengths, and therefore are spectrally resolvable.

In other embodiments, the energy transfer dye may be attached to the linker at the same point of attachment, i.e. may be attached at one atom of the labeling species. In other embodiments, the energy transfer dye may be attached to different atoms in the labeling species, while still being configured to donate and accept excitation energy for energy transfer dye performance.

In other embodiments, the labeling species may be labeled with a quencher dye which may be configured to quench fluorescence of a fluorescent dye. In yet other embodiments, the labeling species may contain a fluorescent dye and a quencher dye.

In certain embodiments, the dye includes, but is not limited to Cascade Blue, FAM™, JOE™, VIC™, HEX™, TET™, NED™, PET®, TAMRA™, ROX™, R110, R6G, Texas Reds, aminopyrene trisulfonic acid (APTS), NBD, BigDye™, 2-AA (anthranilic acid), 2-AB (2-aminobenzamide), aminoxyTMT™ mass tag labeling reagents (available from Thermo Scientific), or a tautomer or salt thereof, or a combination thereof.

Certain embodiments provide a method for detecting a glycan in a biomolecule, comprising:
(a) cleaving the glycan from the biomolecule generating a cleaved glycan;
(b) separating the cleaved glycan;
(c) labeling the cleaved glycan with a reactive nucleic acid oligomer to form a charged glycan;
(d) migrating the charged glycan under the influence of an electric field in a channel, and
(e) detecting the charged glycan,
wherein the reactive nucleic acid oligomer comprises:
i) a reactive moiety at a first site on the nucleic acid oligomer; and
ii) optionally, a detectable tag at a second site on the nucleic acid oligomer.

In certain embodiment, the charged glycan is negatively charged. In certain embodiments, the biomolecule includes, but is not limited to, a glycoprotein, a glycolipid, a proteoglycan, a phosphoprotein, or a glycan core containing phospholipid-protein. In certain embodiments, the reactive nucleic acid oligomer comprises 1 to 20 nucleotides. In certain embodiments, the detection includes, but is not limited to, detecting the UV absorbance of the nucleic acid oligomer, detecting fluorescence, detecting light in the visible spectrum, detecting a spin label, detecting chemiluminescence, detecting conductance, detecting an electrical signal, or detecting a secondary biological reaction product. In certain embodiments, the detectable tag comprises a dye compound of the present disclosure. (Additional description of this method is provided in co-owned, U.S. Provisional Application Ser. No. 62/087,208, titled "Charged Reactive Oligomers" and PCT Patent Application No. PCT/US2015/063791, titled "Charged Reactive Oligomers, each of which is herein incorporated by reference in its entirety).

In certain embodiments, the method is performed using electrophoresis. In certain embodiments, the method is performed using capillary electrophoresis. In certain embodiments, the method is performed using a glycan analysis system (see, co-owned, co-pending U.S. Provisional Patent Application Ser. No. 62/087,208, titled "Charged Reactive Oligomers" and PCT Patent Application No. PCT/US2015/063791, titled "Charged Reactive Oligomers, each of which is herein incorporated by reference in its entirety).

In certain embodiments, dyes other than the hydrazinyl dye compounds and aminooxy dye compounds provided herein may be used. As used herein, the dye may be a visible dye, a fluorescent dye, or a chemiluminescent dye. In various embodiments, the fluorescent dye may be a pyrene dye, a naphthalene dye, an aminopyridine dye, a xanthene dye which may be a fluorescein, rhodol or rhodamine dye, a cyanine dye, a coumarin dye, a borapolyazaindacine dye, a benzofuran dye, or an indole dye. In some embodiments, the fluorescent dye may be aminopyrene trisulfonic acid (APTS). In certain embodiments, the APTS dye may be selected from those described in co-owned, co-pending U.S. Provisional Patent Application Ser. No. 62/087,208, titled "Charged Reactive Oligomers" and PCT Patent Application No. PCT/US2015/063791, titled "Charged Reactive Oligomers, each of which is herein incorporated by reference in its entirety, including, but not limited to:

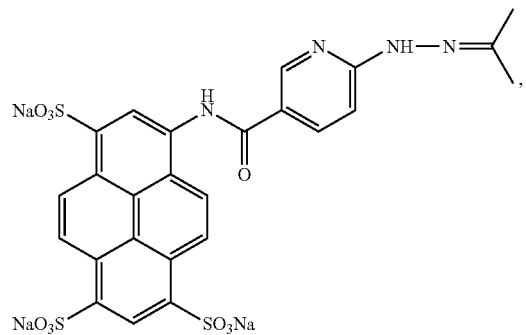

APTS-SANH

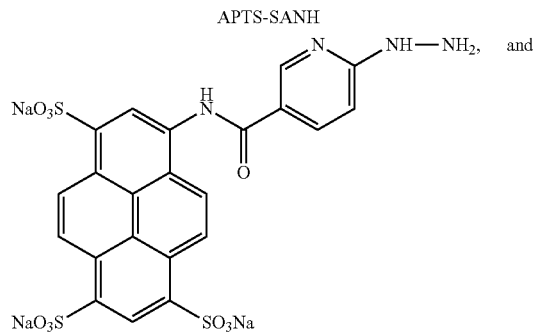

APTS-SHNH

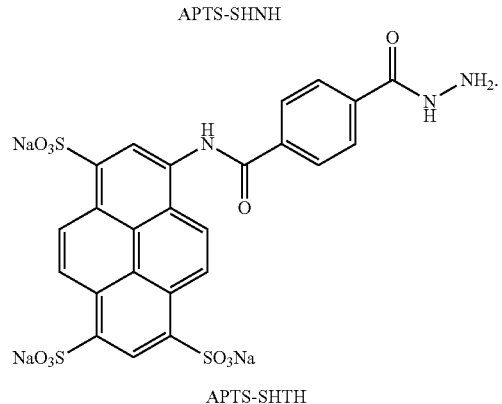

APTS-SHTH

In other embodiments, the fluorescent dye may be a fluorescein dye or a rhodamine dye. In various embodiments, more than one dye may be incorporated in the labeling species. When more than one dye may be incorporated in the labeling species, the fluorescent dye may be a polymeric dye or an energy transfer dye. An energy transfer dye may have a donor dye and an acceptor dye, where the donor dye may be configured to absorb energy at one wavelength and emit energy at a second wavelength which emitted energy excites the acceptor dye at the second wavelength. The acceptor dye then emits at a third wavelength, which may be detectable. If more than one labeling species may be used in a glycan detection assay where more than one energy transfer dye may be used to label various different glycans, then the more than one energy transfer dye are configured to be detected at different wavelengths, and therefore are spectrally resolvable.

In other embodiments, the energy transfer dye may be attached to the linker at the same point of attachment, i.e. may be attached at one atom of the labeling species. In other embodiments, the energy transfer dye may be attached to different atoms in the labeling species, while still being configured to donate and accept excitation energy for energy transfer dye performance.

In other embodiments, the labeling species may be labeled with a quencher dye which may be configured to quench fluorescence of a fluorescent dye. In yet other embodiments, the labeling species may contain a fluorescent dye and a quencher dye.

In certain embodiments, the dye includes, but is not limited to Cascade Blue, FAM™ JOE™, VIC™, HEX™, TET™, NED™, PET®, TAMRA™, ROX™, R110, R6G, Texas Red®, aminopyrene trisulfonic acid (APTS), NBD, BigDye™, 2-AA (anthranilic acid), 2-AB (2-aminobenzamide), aminoxyTMT™ mass tag labeling reagents (available from Thermo Scientific), or a tautomer or salt thereof, or a combination thereof.

In certain embodiments, the method is performed using chromatography. In certain embodiments, the method is performed using high-performance liquid chromatography (HPLC) or liquid chromatography-mass spectroscopy (LC-MS).

In certain embodiments, the sample contains one or more glycans that can be the same or different. In certain embodiments, the method can be performed on one or more samples that each contains one or more glycans. In certain embodiments, each of the samples can be incubated with a different dye compound provided herein to allow for multiplexing.

In one embodiment, a known quantity of a reference glycan or mixture of glycans can be included in a glycan sample that is to be analyzed according to the methods that are described herein. The reference glycan can then be used to provide a relative quantification for other glycans in the sample.

In one embodiment, the reference glycan is selected so that it is unlikely to occur naturally in the glycan sample. This will ensure that the reference glycan does not interfere with the analysis. Alternatively, the reference glycan can be labeled with a dye compound provided herein that allows it to be differentiated from other glycans in the sample that may be labeled with a different dye compound or a collection of different dye compounds provided herein. The addition of a known quantity of reference glycan to the glycan sample enables each component of the glycan sample to be quantified.

Absolute quantification of glycans can be accomplished by spiking the sample to be analyzed with an appropriate labeled standard. Relative quantitation of glycans can be accomplished by comparison of fluorescence peak areas of the species that are resolved by methods such as capillary electrophoresis.

Thus, in certain embodiments, the present disclosure provides a method of characterizing a sample containing one or more glycans, the method comprising:

a) providing a sample containing one or more glycans and a known quantity of a reference glycan standard, wherein the reference glycan standard is labeled with a dye compound provided herein;

b) contacting the sample with a dye compound provided herein that is different from the dye compound used in step (a);

c) separating the sample by electrophoresis; and d) quantifying at least one glycan in the sample relative to the reference glycan standard.

In certain embodiments, the method is performed using capillary electrophoresis. In certain embodiments, the method is performed using a glycan analysis system (see, co-owned, co-pending U.S. Provisional Patent Application Ser. No. 62/087,208, titled "Charged Reactive Oligomers" and PCT Patent Application No. PCT/US2015/063791, titled "Charged Reactive Oligomers, each of which is herein incorporated by reference in its entirety).

According to various embodiments, the glycans may be identified by comparison of their retention times (on an electrophoretogram) against a ladder standard. The ladder standard may be a set of fluorescently labeled carbohydrate oligomers differing by one saccharide molecule, two saccharide molecules or any selected interval of monosaccharide units. The ladder standard may be, but is not limited to a dextran ladder. Alternatively, the ladder standard may be a set of fluorescently labeled oligonucleotides or any other charged oligomers, so long as the migration of the ladder standard is reproducible and permits comparison with the migration time of the labeled glycans under analysis. The ladder standard, which may be, for example, a dextran ladder standard, may be run in parallel with the glycan samples, and specific glycans may then be identified by locating the time point at which they elute relative to the ladder. Known retention times for specific glycan structures and molecular weights may previously be recorded in an empirically-derived database, which may then be searched. An analysis software may then compare retention times (relative to the ladder standard) of peaks from an electrophoretogram of unknown glycans with the retention time database to identify the glycans. The software may include a database specific for IgG glycans, among other glycans and glycoforms.

Figure 12A:
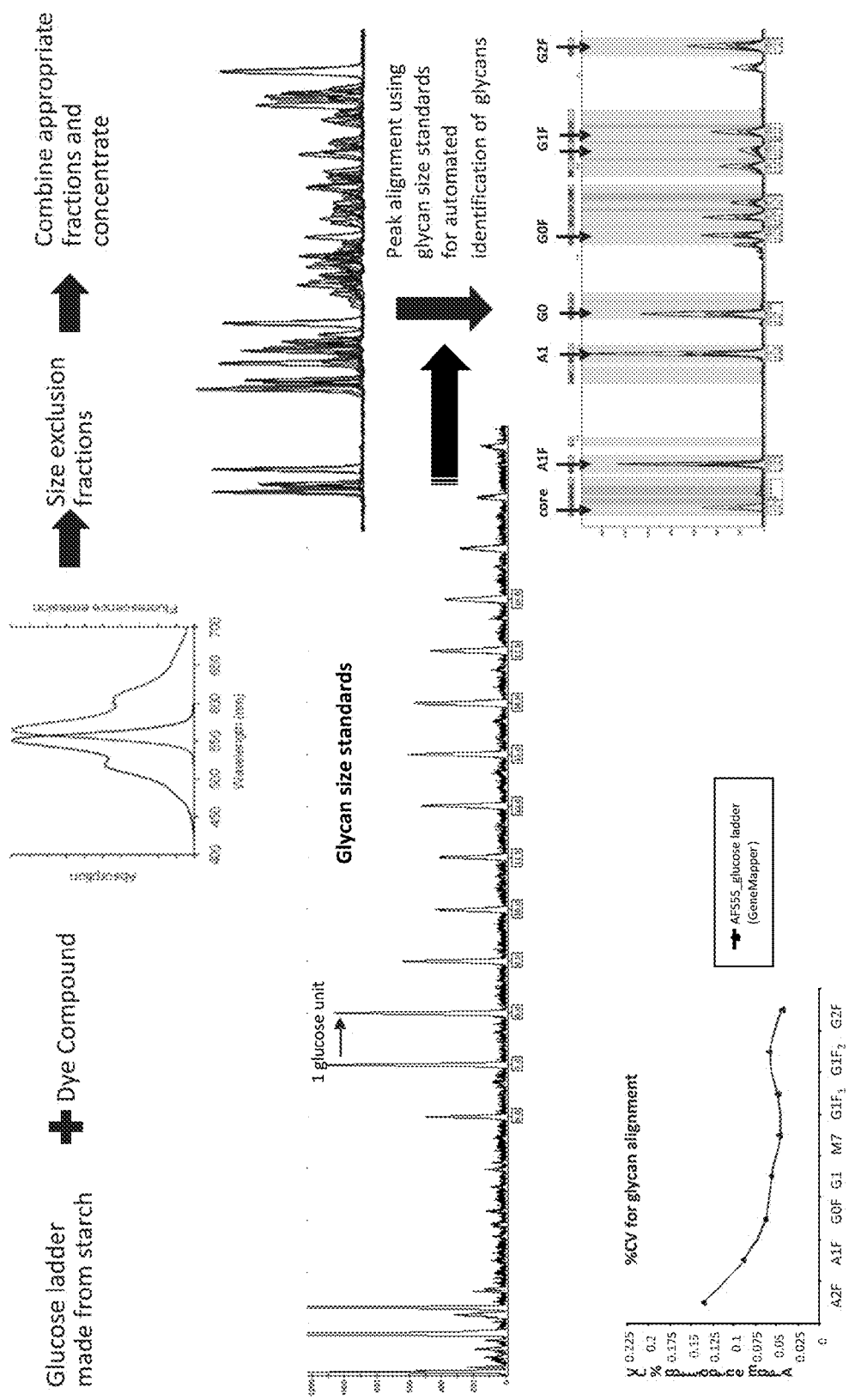
FIG. 12A: Schematic outline of preparing and use of glycan size standards according to certain embodiments of the present disclosure.
Figure 12B:
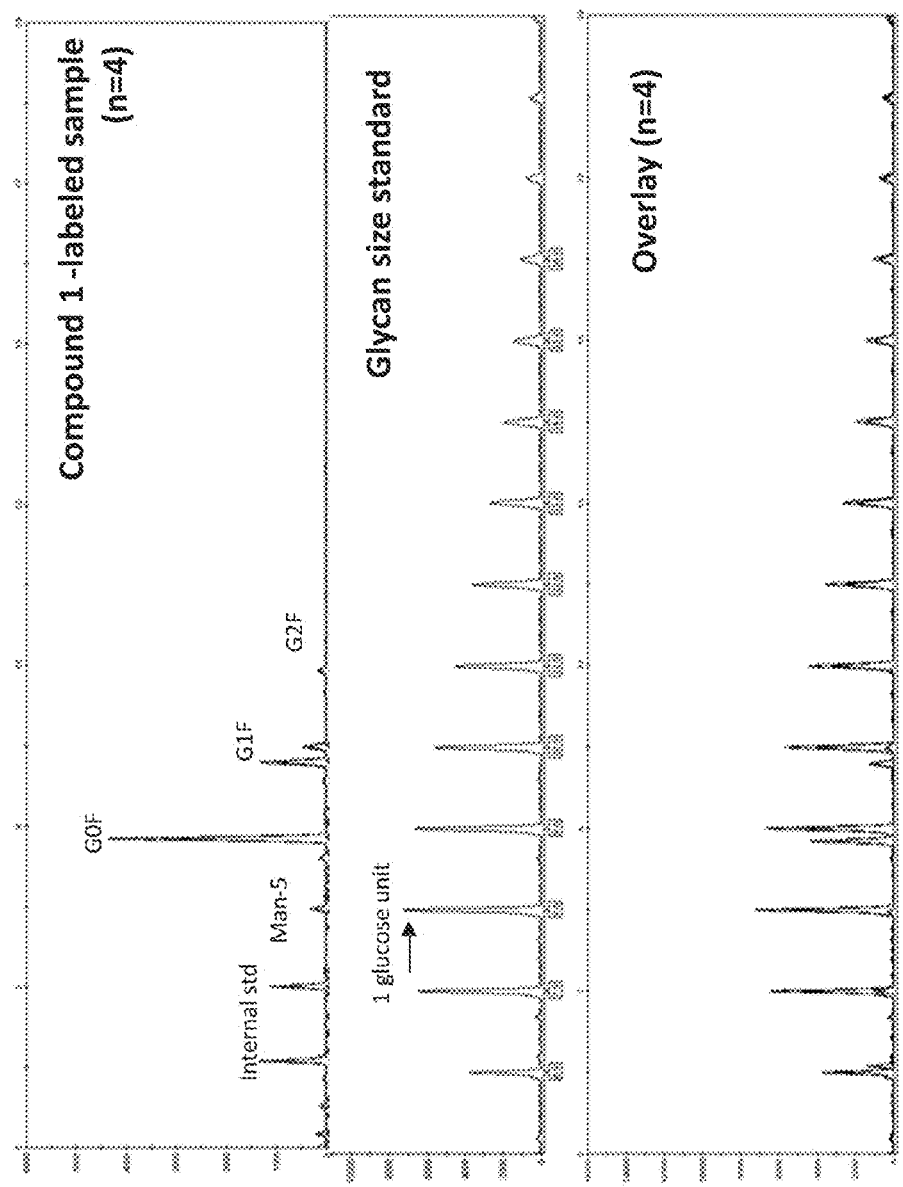
FIG. 12B: Representative electrophoretograms showing that the size standards are separated by one glucose unit and are detected in a different channel than the labeled glycan in a 3500 GENETIC ANALYZER (see, co-owned, co-pending U.S. Provisional Patent Application Ser. No. 62/087,208, titled "Charged Reactive Oligomers" and PCT Patent Application No. PCT/US2015/063791 titled "Charged Reactive Oligomers, each of which is herein incorporated by reference in its entirety). Top=Compound 1-labeled sample; Middle=glycan size standard; Bottom=Overlay of the top and middle electrophoretograms.
Figure 12C:
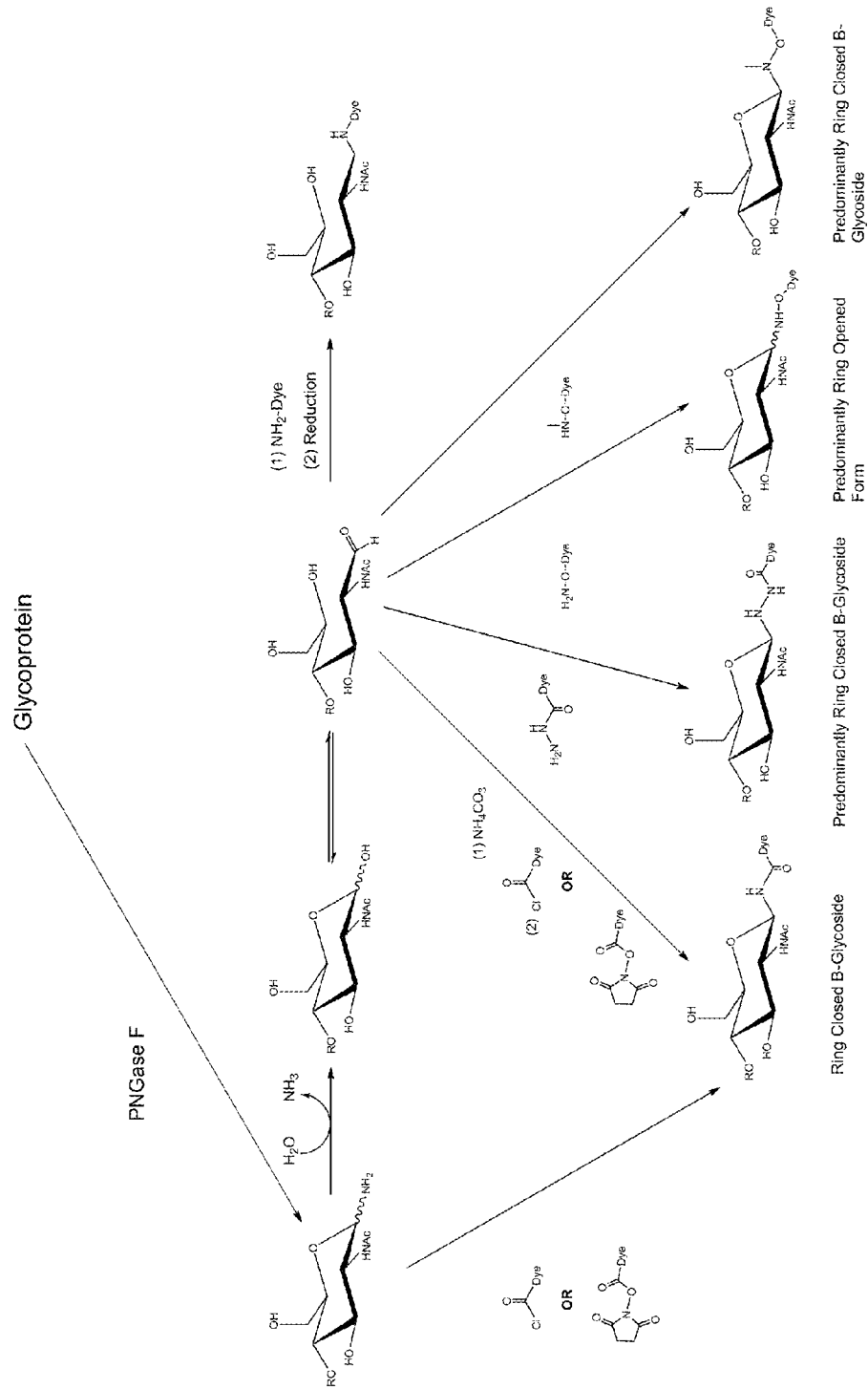
FIG. 12C: Schematic of various methods for reduced end conjugation of glycans.
Figure 12D:
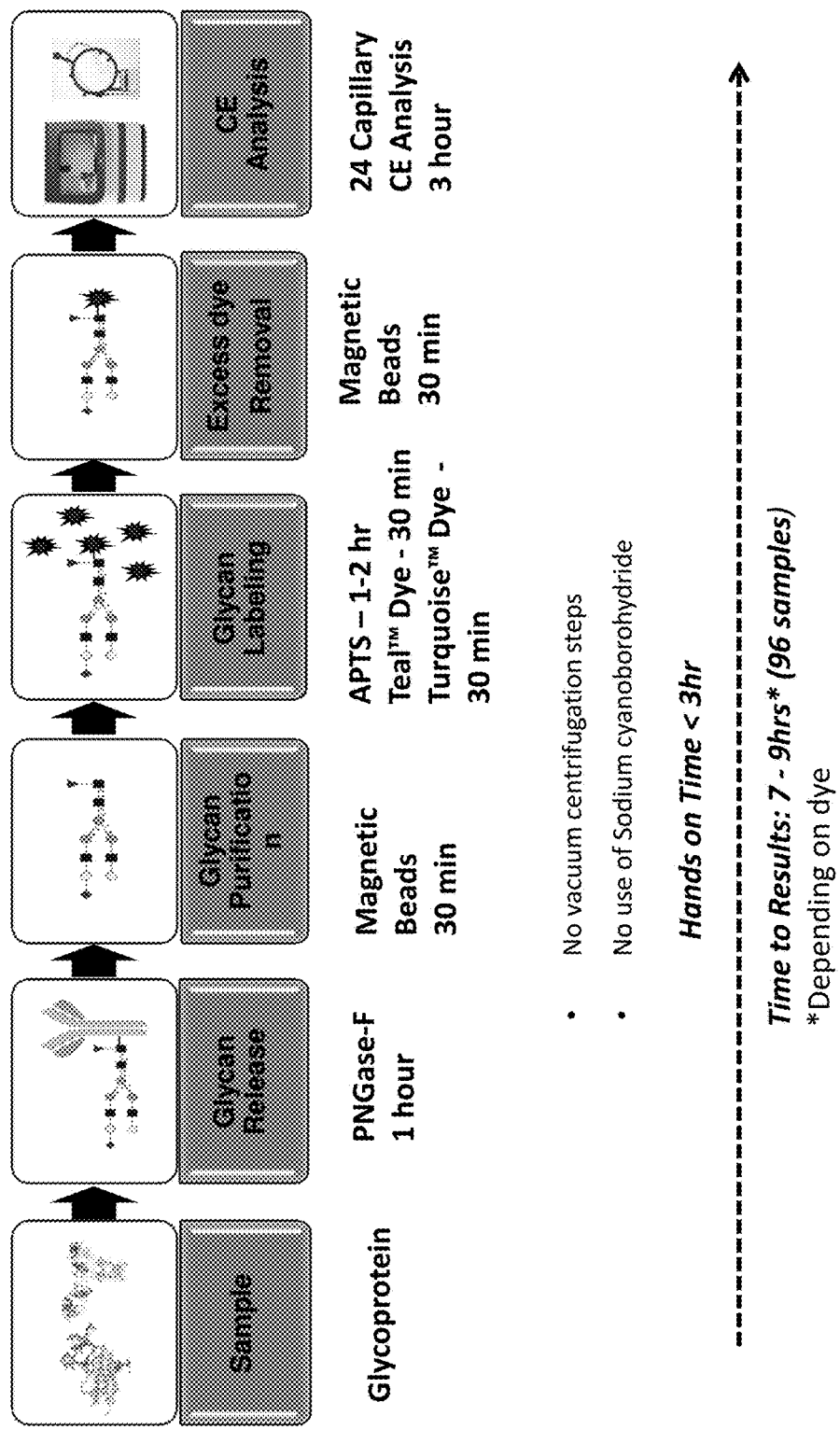
FIG. 12D: Schematic of an exemplary workflow for glycan analysis according to certain embodiments disclosed herein.

Labeling glycans with multiple dye compounds described herein which have superior sensitivity enables a simpler sample prep for glycan analysis and a more efficient workflow (See, FIG. 12D). The sensitive dye compounds provided herein also provide reproducible, overlapping glycan peaks in assays (for example, an overlay of 288 injections produced completely overlapping glycan peaks). The superior dye sensitivity also requires lower glycoprotein (sample) input.

Sample handling is further simplified by using magnetic bead based sample prep. Thus, in a typical sample preparation, the hands-on-time can be reduced, for example, to <3 hrs for 96 samples, while current methods can take up to 24 hours for sample prep. In certain aspects, sample prep and data for 96 samples can be collected within 7-9 hours, depending on the dye type used in labeling. A typical, exemplary glycan analysis workflow is depicted in FIG. 12D: enzymatic glycan release (1 hour), magnetic bead glycan purification (30 min), glycan dye labeling (2 hour), optional (depending on choice of dye), excess dye removal (30 min), CE analysis (3 hour).

Some additional advantages seen due to the use of the dye compounds provided herein are: 1) lesser number of pipetting steps during sample prep since steps like purification of excess dye after labeling are unnecessary when certain dyes are used in labeling, 2) elimination of the use of toxic sodium cyanoborohydride from the CE analysis method, and 3) elimination of vacuum centrifugation steps. Among the glycan species that were resolved well using the methods described include: sialyated glycans, glycan structural isomers, fucose species, high mannose species, and others.

A sample comprising a biomolecule or a glycoconjugate may be obtained from a wide variety of sources including, but not limited to, therapeutic formulations and biological samples, which may include but is not limited to cell cultures, patient samples (including tissue, sputum, blood or urine) or manufacturing processes for therapeutics or other commercially relevant biomolecule or glycoconjugates of interest. In certain embodiments, the biomolecule or glycoconjugate may be a glycoprotein or a glycolipid. In the methods provided herein, the at least one glycan may be cleaved chemically, for example, by periodate, producing the at least glycan with an aldehyde functionality which can be further modified to aid in its detection. Alternatively, the at least one glycan may be cleaved using at least one glycan-cleaving enzyme, producing the at least one glycan having a reducing functionality, i.e. a hemiacetal or the like, which can be further modified to aid in its detection. In certain embodiments, more than one glycan-cleaving enzyme may be used to produce differing patterns of glycan cleavage. In certain embodiments, the at least one glycan-cleaving enzyme may be a glycosidase. In certain embodiments, the at least one glycan-cleaving enzyme may be an endoglycosidase.

Glycosidases are specific enzymes that recognize the sugar linkages, and in some cases, the neighboring sugar in the oligo/polysaccharide before cleaving at the precise linkage. Glycosidases used in the methods provided herein may be an endoglycosidase, an exoglycosidase, or a combination thereof. Endoglycosidases cleave oligo or polysaccharides, or glycans, from a biomolecule or glycoconjugate, producing a reducing sugar terminus of a cleaved glycan structure which can be further labeled with various labeling species for detection and identification. Exoglycosidases have varied specificities which can be harnessed to specifically and sequentially cleave glycan structures from a terminus, and so explore glycan structure in a given biomolecule or glycoconjugate. In certain embodiments of the methods provided herein, cleavage with an endoglycosidase may be performed to release a glycan that may be all or the majority of the polysaccharide attached to the biomolecule or glycoconjugate. In some embodiments, a suitable endoglycosidase used for cleaving a glycan from the biomolecule or glycoconjugate may be endoglycosidase F, endoglycosidase F1, endoglycosidase F2, endoglycosidase H, endoglycosidase S, or endoglycosidase D. Alternatively, one or more exoglycosidase may be used to cleave glycans from the terminus of the glycan, and may include, but is not limited to, one or more of α1-2 fucosidase, α1-2,3 mannosidase, α1-3 6 galactosidase, α1-6 mannosidase, α2-3 neuramidase α2-3 neuramidase S, α2-3,6,8 neuramidase, α2-3, 6, 8, 9 neuramidase A, β-N-acetylhexosamidase$_f$, β-N—acetylglucosamidase, β-N-acetylglucosamidase S, β1-3 galactosidase, β1-4 galactosidase, β1-4 galactosidase S, and the like.

In certain embodiments, cleaving a glycan from each of the denatured glycoprotein samples may include cleaving the glycans using PNGase F, or using endoglycosidase-H, or using one or more of endoglycosidase D, endoglycosidase F1, endoglycosidase F2, and endoglycosidase F3, or using one or more of ABS (*arthrobacter ureafaciens* sialidase), NAN 1 (recombinant sialidase), AMF (almond meal alpha-fucosidase), BKF (bovine kidney alpha-fucosidase), BTG (bovine testes beta-galactosidase), SPG (*streptococcus peneumoniae* beta-galactosidase), GUH (*streptococcus pheumoniae* hexosaminidase, recombinant in *E. coli*), and JBM (jack bean mannosidase), or using peptide-N-(N-acetyl-β-glucosaminyl)asparagine amidase, for example. Cleaving the glycan using peptide-N-(N-acetyl-β-glucosaminyl) asparagine amidase may include cleaving N-linked glycans.

According to various exemplary embodiments, N-linked glycans may be enzymatically cleaved using PNGase, and glycans may be fluorescently labeled at their reducing end with a modified dye directly containing either a hydrazide or oxyamine functional group (e.g., a carbonyl reactive group) in a 100 microliters sample well, plate, tube, or the cleaved glycans may be fluorescently labeled using the charged reactive oligomers (see, co-owned, co-pending U.S. Provisional Patent Application Ser. No. 62/087,208, titled "Charged Reactive Oligomers" and PCT Patent Application No. PCT/US2015/063791, titled "Charged Reactive Oligomers, each of which is herein incorporated by reference in its entirety). Labeling may involve the formation of a hydrazone between a sugar carbonyl and the dye compound hydrazide or the formation of an oxime between the sugar carbonyl and the dye compound hydroxylamine. The labeled glycans may inherit a negative charge due to sulfonic acids that may be in the dye, or through the charged reactive oligomers (with or without linkers, further, with or without mobility modifiers), and, as a result, they may migrate in any differential charge field, for e.g., an electric field. The labeled glycans can be separated, for e.g., by capillary gel electrophoresis and may be detected by fluorescence using, for example, a laser diode (e.g., 488 nm) for excitation and a CCD camera (including, e.g., a 510 nm bandpass filter) for detection. Detection may generate an electrophoretogram showing peaks representing individual glycans as they migrate past the laser/detector (for example, see FIGS. 8A-8B).

Illumination:

The sample or medium in which the dye compound is present is illuminated with a wavelength of light selected to give a detectable optical response, and observed with a means for detecting the optical response. Equipment that is useful for illuminating the present compounds and compositions disclosed herein includes, but is not limited to, hand-held ultraviolet lamps, mercury arc lamps, xenon lamps, lasers and laser diodes. These illumination sources are optically integrated into laser scanners, fluorescence microplate readers or standard or microfluorometers.

The dye compounds provided herein may, at any time after or during an assay, be illuminated with a wavelength of light that results in a detectable optical response, and observed with a means for detecting the optical response. Upon illumination, such as by an ultraviolet or visible wavelength emission lamp, an arc lamp, a laser, or even sunlight or ordinary room light, the fluorescent compounds, including those bound to the complementary specific binding pair member, display intense visible absorption as well as fluorescence emission. Selected equipment that is useful for illuminating the fluorescent compounds provided herein includes, but is not limited to, hand-held ultraviolet lamps, mercury arc lamps, xenon lamps, argon lasers, laser diodes, and YAG lasers. These illumination sources are optionally integrated into laser scanners, fluorescence microplate readers, standard or mini fluorometers, or chromatographic detectors. This fluorescence emission is optionally detected by visual inspection, or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, a fluorescence microscope or a fluorometer, the instrument is optionally used to distinguish and discriminate between the fluorescent compounds provided herein and a second fluorophore with detectably different optical properties, typically by distinguishing the fluorescence response of the fluorescent compounds provided herein from that of the second fluorophore. Where a sample is examined using a flow cytometer, examination of the sample optionally includes isolation of particles within the sample based on the fluorescence response by using a sorting device. In another embodiment, the illumination source is used to form a covalent bond between the present dye and an analyte of interest. In this instance the dye comprises a photoactivatable reactive group, such as those discussed above.

Applications:

It will be appreciated that the dye compounds described herein can be utilized in any of a variety of applications. In general, the dye compounds, compositions, kits and methods provided herein are useful in any application that involves the structural characterization of analytes such as glycans.

The dye compounds and methods of the present disclosure can be applied to glycan samples obtained from a wide variety of sources including, but not limited to, therapeutic formulations and biological samples. A biological sample may undergo one or more analysis and/or purification steps prior to or after being analyzed according to the present disclosure. To give but a few examples, in some embodiments, a biological sample is treated with one or more proteases and/or glycosidases (e.g., so that glycans are released); in some embodiments, glycans in a biological sample are labeled with one or more dye compounds provided herein. Any of a variety of separation and/or isolation steps may be applied to a biological sample in accordance with the present disclosure.

The dye compounds and methods of the present disclosure can be utilized to analyze glycans in any of a variety of states including, for example, free glycans, glycoconjugates (e.g., glycopeptides, glycolipids, proteoglycans, etc.), or cells or cell components, etc.

The dye compounds and methods of the present disclosure can be used to significantly expedite one or more stages of process development for the production of a therapeutic or other commercially relevant glycoprotein of interest. Non-limiting examples of such process development stages that can be improved using methods of the present disclosure include cell selection, clonal selection, media optimization, culture conditions, process conditions, and/or purification procedure. Those of ordinary skill in the art will be aware of other process development stages that can be improved.

The methods and dye compounds disclosed herein can also be used to monitor the extent and/or type of glycosylation occurring in a particular cell culture, thereby allowing adjustment or possibly termination of the culture in order, for example, to achieve a particular desired glycosylation pattern or to avoid development of a particular undesired glycosylation pattern.

The methods and dye compounds disclosed herein can also be utilized to assess glycosylation characteristics of cells and or cell lines that are being considered for production of a particular desired glycoprotein (for example, even before the cells or cell lines have been engineered to produce the glycoprotein, or to produce the glycoprotein at a commercially relevant level).

In some embodiments, a desired glycosylation pattern for a particular target glycoprotein is known, and the technology described herein allows the monitoring of culture samples to assess progress of the production along a route known to produce the desired glycosylation pattern. For example, where the target glycoprotein is a therapeutic glycoprotein, for example, having undergone regulatory review in one or more countries, it will often be desirable to monitor cultures to assess the likelihood that they will generate a product with a glycosylation pattern as close to identical with the established glycosylation pattern of the pharmaceutical product as possible, whether or not it is being produced by exactly the same route. As used herein, "close to identical" refers to a glycosylation pattern having at least 90%, 95%, 98%, or 99% correlation to the established glycosylation pattern of the pharmaceutical product. In such embodiments, samples of the production culture are typically taken at multiple time points and are compared with an established standard or with a control culture in order to assess relative glycosylation.

Whether or not monitoring production of a particular target protein for quality control purposes, the dye compounds, compositions, methods and kits of the present disclosure may be utilized, for example, to monitor glycosylation at particular stages of development, or under particular growth conditions.

In some particular embodiments of the present disclosure, the methods and dye compounds provided herein can be used to characterize and/or control or compare the quality of therapeutic products. To give but one example, the present methods and dye compounds can be used to assess glycosylation in cells producing a therapeutic protein product. Particularly given that glycosylation can often affect the activity, bioavailability, or other characteristics of a therapeutic protein product, methods for assessing cellular glycosylation during production of such a therapeutic protein product are particularly desirable. Among other things, the methods and dye compounds provided herein can facilitate real time analysis of glycosylation in production systems for therapeutic proteins.

Representative therapeutic glycoprotein products whose production and/or quality can be monitored in accordance with the present disclosure include, for example, any of a variety of hematologic agents (including, for example, erythropoietins, blood-clotting factors, etc.), interferons, colony stimulating factors, antibodies, enzymes, and hormones.

In some embodiments, the disclosure provides methods in which glycans from different sources or samples are compared with one another. In certain embodiments, the disclosure provides methods used to monitor the extent and/or type of glycosylation occurring in different cell cultures. In some such examples, multiple samples from the same sourced are obtained over time, so that changes in glycosylation patterns (and particularly in cell surface glycosylation patterns) are monitored. In some embodiments, one of the samples is a reference sample. For example, in certain embodiments, the methods and dye compounds provided herein can be used to monitor the extent and/or type of glycosylation occurring in different cell cultures.

In some embodiments, the methods and dye compounds disclosed herein can be used to compare glycans from different cell culture samples prepared under conditions that differ in one or more selected parameters (e.g., cell type, culture type, culture conditions, culture time, isolation steps, etc.) but are otherwise identical in order to determine the effects of the single selected parameter on the glycosylation pattern. Among other applications, therefore, use of the dye compounds and methods disclosed herein may facilitate determination of the effects of particular parameters on glycosylation patterns in cells.

In some embodiments, glycans from different batches of a glycoprotein of interest (e.g., therapeutic glycoprotein), whether prepared by the same method or by different methods, and whether prepared simultaneously or separately, are compared. In such embodiments, the methods and dye compounds provided herein are used to facilitate quality control of glycoprotein preparation. Alternatively or additionally, some such embodiments facilitate monitoring of progress of a particular culture producing a glycoconjugate of interest (e.g., when samples are removed from the culture at different time points and are analyzed and compared to one another). In any of these embodiments, features of the glycan analysis can be recorded, for example in a quality control record. As indicated above, in some embodiments, a comparison is with a historical record of a prior or standard batch and/or with a reference sample of glycoprotein.

In certain embodiments, the methods, dye compounds, compositions and kits of the present disclosure may be utilized in studies to modify the glycosylation characteristics of a cell, for example to establish a cell line and/or culture conditions with one or more desirable glycosylation characteristics. Such a cell line and/or culture conditions can then be utilized, if desired, for production of a particular target glycoconjugate (e.g., glycoprotein) for which such glycosylation characteristic(s) is/are expected to be beneficial.

In certain embodiments, the methods and dye compounds of the present disclosure are applied to glycans that are present on the surface of cells. In some such embodiments, the analyzed glycans are substantially free of non-cell-surface glycans. In some such embodiments, the analyzed glycans, when present on the cell surface, are present in the context of one or more cell surface glycoconjugates (e.g., glycoproteins or glycolipids).

In some particular embodiments, cell surface glycans are analyzed in order to assess glycosylation of one or more target glycoproteins of interest, particularly where such target glycoproteins are not cell surface glycoproteins. Such embodiments can allow one to monitor glycosylation of a target glycoprotein without isolating the glycoprotein itself. In certain embodiments, the methods disclosed herein utilize cell-surface glycans as a readout of or proxy for glycan structures on an expressed glycoprotein of interest. In certain embodiments, such methods include, but are not limited to, post process, batch, screening or "in line" measurements of product quality. Such methods can provide for an independent measure of the glycosylation pattern of a produced glycoprotein of interest using a byproduct of the production reaction (e.g., the cells) without requiring the use of destruction of any produced glycoprotein. Furthermore, methods of the present disclosure can avoid the effort required for isolation of product and the potential selection of product glycoforms that may occur during isolation.

In certain embodiments, the methods, dye compounds, compositions and kits of the present disclosure are applied to glycans that are secreted from cells. In some such embodiments, the analyzed glycans are produced by cells in the context of a glycoconjugate (e.g., a glycoprotein or glycolipid).

The methods, dye compounds, compositions and kits described herein can be used to detect desirable or undesirable glycans, for example to detect or quantify the presence of one or more contaminants in a product, or to detect or quantify the presence of one or more active or desired species.

In various embodiments the methods provided herein can be used to detect biomarkers indicative of, e.g., a disease state, prior to the appearance of symptoms and/or progression of the disease state to an untreatable or less treatable condition, by detecting one or more specific glycans whose presence or level (whether absolute or relative) may be correlated with a particular disease state (including susceptibility to a particular disease) and/or the change in the concentration of such glycans over time.

In certain embodiments, the methods facilitate detection of glycans that are present at very low levels in a source (e.g., a biological sample). In such embodiments, it is possible to separate over 10, 20, 30, 40, 50, 60, 70, 80, 90 or 100 glycan components of a mixture.

In some embodiments, the techniques may be combined with one or more other technologies for the detection, analysis, and or isolation of glycans or glycoconjugates.

Kits:

Additional embodiments of the present disclosure include kits comprising the labeling reagents described herein for use in labeling carrier molecules or solid supports. In addition to the compounds, the kits include instructions on how to reporter molecule the carrier molecule or solid support.

In certain embodiments, a kit is provided for detecting an analyte in a sample, wherein the kit comprises:

a) a compound of the invention or a tautomer or salt thereof; and b) instructions for detecting the analyte according to one or more methods described herein.

In certain embodiments, a kit is provided for detecting an analyte in a sample, wherein the kit comprises:

a) a compound of Formula (I) or a tautomer or salt thereof:

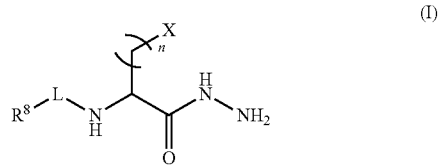

(I)

wherein,

L is a linker;

$R^a$ is a reporter molecule, carrier molecule or a solid support;

n is an integer from 1 to 24; and

X is a molecule containing $SO_3H$, $SO_3^-$, $OPO_3^{2-}$, $OPO_3H_2$, $PO_3H_2$, $PO_3^{2-}$, COOH, or $COO^-$; and b) instructions for detecting the analyte according to one or more of the methods described herein.

In certain embodiments, L is a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is a dye. More particularly, the dye is a pyrene, a xanthene, a cyanine, an indole, a benzofuran, a coumarin, or a borapolyazaindacine.

In certain embodiments, $R^a$ is a chelating moiety, a hapten, an antibody, an enzyme, a radiolabel, a metal ion or metal ion containing substance, a pigment, a chromogen, a phosphor, a fluorogen, a bioluminescent substance, a chemiluminescent substance, or a semiconductor nanocrystal. More particularly, $R^a$ is avidin, streptavidin or an analog thereof.

In certain embodiments, $R^a$ is a solid support.

In certain embodiments, $R^a$ is a carrier molecule. More particularly, the carrier molecule is selected from the group consisting of an amino acid, a peptide, a protein, a carbohydrate, a polysaccharide, a nucleoside, a nucleotide, an oligonucleotide, a nucleic acid polymer, a drug, a lipid, and a synthetic polymer.

In certain embodiments, the compound of Formula (I) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, $R^a$ is:

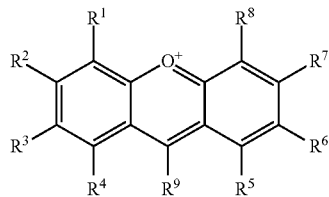

or a tautomer or salt thereof;
wherein,
$R^1$, $R^2$, $R^3$, $R^4$, $R^5$, $R^6$, $R^7$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or one or more of $R^1$ and $R^2$, $R^2$ and $R^3$, $R^3$ and $R^4$, $R^5$ and $R^6$, $R^6$ and $R^7$ or $R^7$ and $R^8$ are taken together to form a fused aryl or heteroaryl group; and one of $R^1$, $R^2$, $R^3$, $R^4$, $R^5$, $R^6$, $R^7$, $R^8$ and $R^9$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

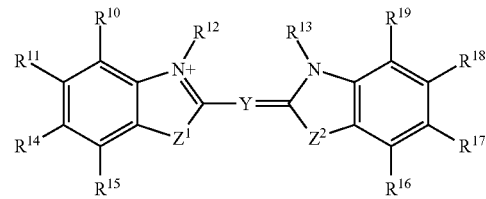

or a tautomer or salt thereof;
wherein,
$Z^1$ and $Z^2$ are each independently O, S, $NR^{23}$ or $CR^{24}R^{25}$;
Y is $-CR^{20}=(CR^{21}-CR^{22}=)_p$;
p is 0, 1, 2, or 3;
$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;
$R^{12}$, $R^{13}$ and $R^{23}$ are each independently H, alkyl, substituted alkyl, cycloalkyl, substituted cycloalkyl, aryl, substituted aryl, heteroaryl, substituted heteroaryl, heterocyclyl, substituted heterocyclyl;
$R^{20}$, $R^{21}$ and $R^{22}$ are each independently, H, alkyl, substituted alkyl, cycloalkyl, substituted cycloalkyl, aryl, substituted aryl, heteroaryl, or substituted heteroaryl;
$R^{24}$ and $R^{25}$ are H, alkyl or substituted alkyl; and
one of $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

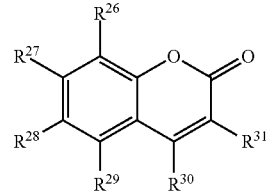

or a tautomer or salt thereof;
wherein,
$R^{26}$, $R^{27}$, $R^{28}$, $R^{29}$, $R^{30}$ and $R^{31}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{26}$, $R^{27}$, $R^{28}$, $R^{29}$, $R^{30}$ and $R^{31}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

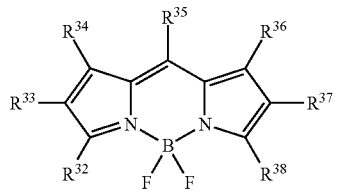

or a tautomer or salt thereof;
wherein, $R^{32}$, $R^{33}$, $R^{34}$, $R^{35}$, $R^{36}$, $R^{37}$ and $R^{38}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{32}$, $R^{33}$, $R^{34}$, $R^{35}$, $R^{36}$, $R^{37}$ and $R^{38}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

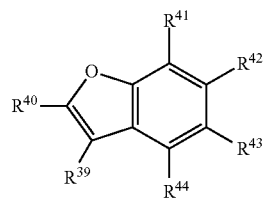

or a tautomer or salt thereof;
wherein, $R^{39}$, $R^{40}$, $R^{41}$, $R^{42}$, $R^{43}$ and $R^{44}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{39}$, $R^{40}$, $R^{41}$, $R^{42}$, $R^{43}$ and $R^{44}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, $R^a$ is:

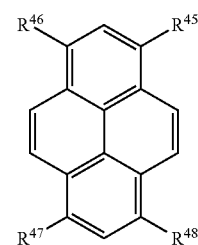

or a tautomer or salt thereof;
wherein, $R^{45}$, $R^{46}$, $R^{47}$, and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{45}$, $R^{46}$, $R^{47}$, and $R^{48}$ is the point of attachment to L through a covalent bond, -alkyl-, -substituted alkyl-, -alkenyl-, -substituted alkenyl-, -carboxamidyl-, -substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-, -sulfonamidyl-, -substituted sulfonamidyl-, -thio-, -amino-, or -substituted amino-.

In certain embodiments, a kit is provided for detecting an analyte in a sample, wherein the kit comprises:

a) a compound of Formula (II) or a tautomer or salt thereof:

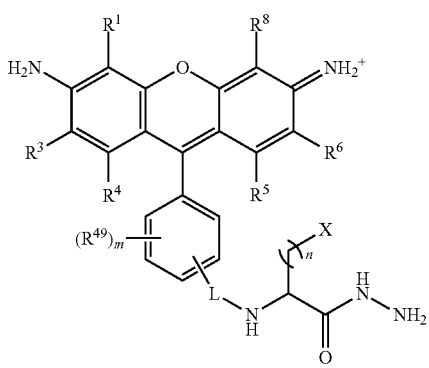

(II)

wherein,

L is a linker;

n is an integer from 1 to 24;

X is a molecule containing $SO_3H$, $SO_3^-$, $OPO_3^{2-}$, $OPO_3H_2$, $PO_3H_2$, $PO_3^{2-}$, COOH, or $COO^-$;

$R^1$, $R^3$, $R^4$, $R^5$, $R^6$, $R^8$ and $R^{49}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and m is 0, 1, or 2; and b) instructions for detecting the analyte according to one or more of the methods described herein.

In certain embodiments, $R^1$ and $R^8$ are each sulfo; $R^2$, $R^3$, $R^4$, $R^5$, $R^6$, and $R^7$ are each H; $R^{49}$ is carboxy; m is 1; L is —C═O; X is selected from $N[(CH_2)_3SO_3H]_2$, $SO_3H$, $SO_3^-$, $OPO_3^{2-}$, $OPO_3H_2$, $PO_3H_2$, $PO_3^{2-}$, COOH, and $COO^-$; and n is 1, 2, 3 or 4. In certain embodiments, the compound of Formula (II) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a kit is provided for detecting an analyte in a sample, wherein the kit comprises:

a) a compound of Formula (III) or a tautomer or salt thereof:

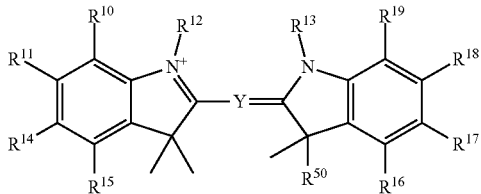

(III)

wherein,

Y is —$CR^{20}$═($CR^{21}$—$CR^{22}$═$)_p$;

p is 0, 1, 2, or 3;

$R^{10}$, $R^{11}$, $R^{14}$, $R^{15}$, $R^{16}$, $R^{17}$, $R^{18}$ and $R^{19}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^{12}$ and $R^{13}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{50}$ is alkyl; and wherein one of $R^{13}$ or $R^{50}$ is:

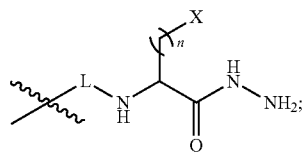

L is a linker;

n is an integer from 1 to 24; and

X is a molecule containing $SO_3H$, $SO_3^-$, $OPO_3^{2-}$, $OPO_3H_2$, $PO_3H_2$, $PO_3^{2-}$, COOH, or $COO^-$; and b) instructions for detecting the analyte according to one or more of the methods described herein.

In certain embodiments, $R^{50}$ is methyl. In certain embodiments, the compound of Formula (III) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a kit is provided for detecting an analyte in a sample, wherein the kit comprises:

a) a compound of Formula (IV) or a tautomer or salt thereof:

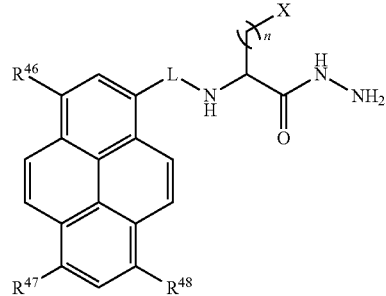

(IV)

wherein,

L is a linker;

n is an integer from 1 to 24;

X is a molecule containing $SO_3H$, $SO_3^-$, $OPO_3^{2-}$, $OPO_3H_2$, $PO_3H_2$, $PO_3^{2-}$, COOH, or $COO^-$; and $R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and b) instructions for detecting the analyte according to one or more of the methods described herein.

In certain embodiments, $R^{46}$, $R^{47}$, and $R^{48}$ are each sulfo; X is carboxy; n is 1 or 2; and L is

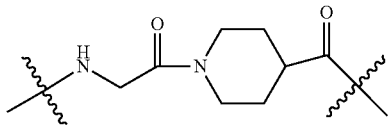 [SMILES: *NCC(=O)N1CCC(C(*)=O)CC1]

In certain embodiments, the compound of Formula (IV) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a kit is provided for detecting an analyte in a sample, wherein the kit comprises:

a) a compound of Formula (V) or a tautomer or salt thereof:

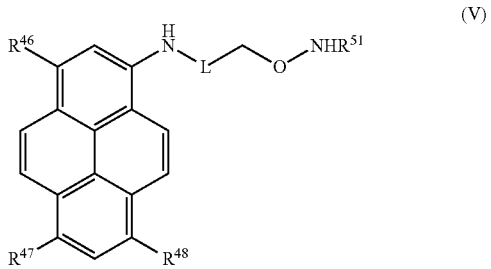

(V)

wherein,

L is a linker;

$R^{46}$, $R^{47}$ and $R^{48}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^{51}$ is selected from H, alkyl and substituted alkyl; and b) instructions for detecting the analyte.

In certain embodiments, $R^{46}$, $R^{47}$, and $R^{48}$ are each sulfo, $R^{51}$ is H, and L is selected from the group consisting of: $-(CH_2)_5C(O)NH(CH_2)_2-$, $-(CH_2)_6NHC(O)-$ and $-C(O)-$. In certain embodiments, the compound of Formula (V) is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, a kit is provided for detecting an analyte in a sample, wherein the kit comprises:

a) a compound selected from the group consisting of:

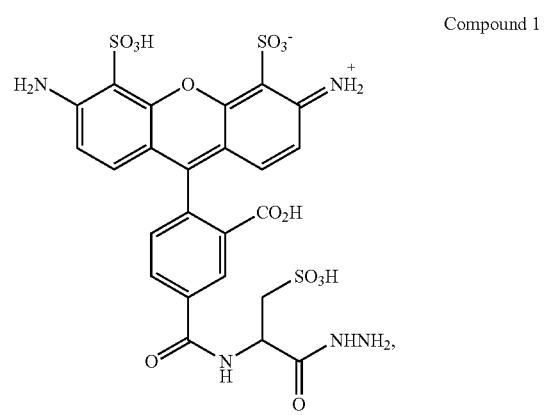

Compound 1

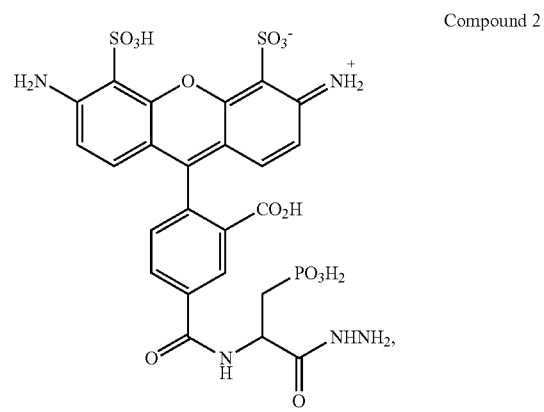

Compound 2

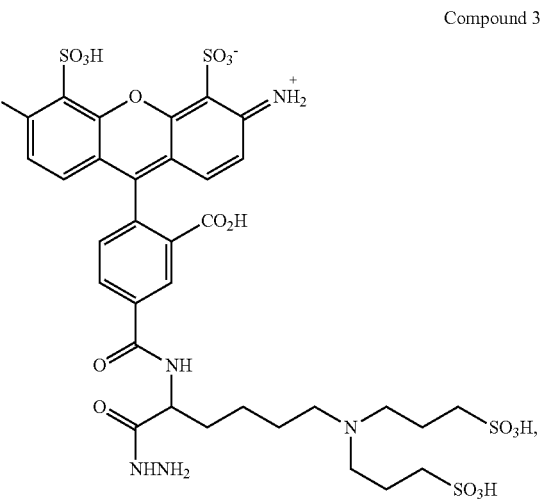

Compound 3

-continued

Compound 4

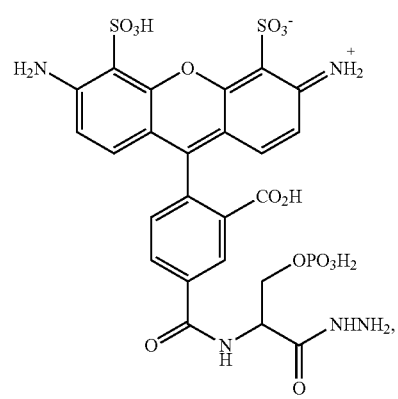

Compound 5

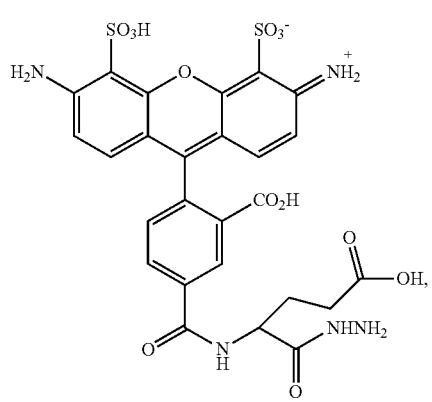

Compound 6

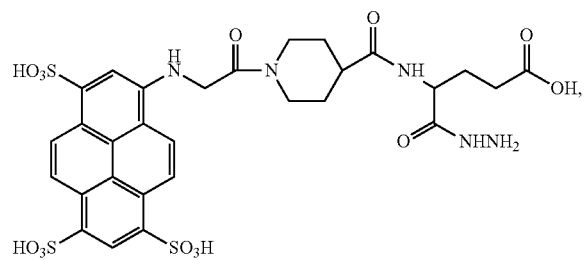

Compound 30

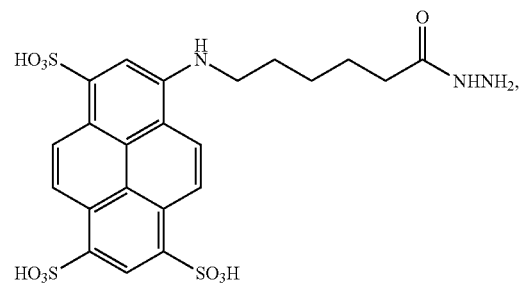

Compound 31

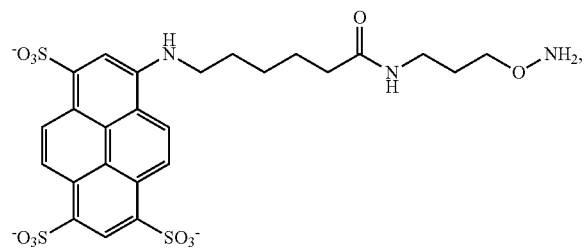

Compound 32

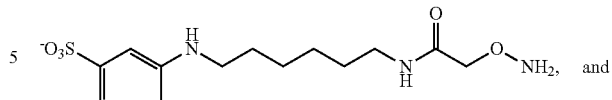

Compound 33

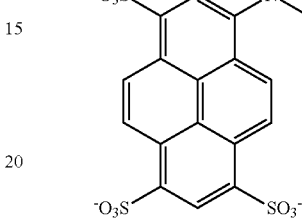

or a salt thereof; and b) instructions for detecting the analyte according to one or more of the methods described herein.

In certain embodiments, the compound is a salt. More particularly, the salt comprises a potassium, sodium, ammonium, alkylammonium, tetralkylammonium, triethylammonium, tert-butylammonium, tetralkyl-phosphonium, tetraaryl-phosphonium, lithium or cesium ion.

In certain embodiments, the kit further comprises instructions for covalently bonding the compound to the analyte. In certain embodiments, the kit further comprises one or more of the following: a buffering agent, a purification medium, a vial comprising the analyte, or an organic solvent, one or more reagents for releasing the glycan from a biomolecule, and optionally, one or more reagents to purify the released glycan from the reaction mixture. In certain embodiments, the reagent for releasing the glycan from a biomolecule is selected from a physical method, a chemical or an enzyme. In certain embodiments, the enzyme is PNGase F.

In certain embodiments, the purification medium is selected from the group consisting of a resin, a bead, a cartridge, a solid support, a plate and a well. In certain embodiments, the bead is a magnetic bead.

In certain embodiments, the kit further comprises instructions for labeling glycans in a sample in preparation of glycan analysis, the method comprising:

treating the sample with a release reagent, such as PNGase F enzyme, with an appropriate buffer under conditions suitable for the release of the glycan from the biomolecule, thereby forming a reaction mixture;

adding beads and buffer to the reaction mixture;

separating the supernatant from the beads;

washing the beads with wash buffer;

eluting the glycans from the beads with elution buffer;

performing dye labeling of the glycans using one or more dye compounds provided herein, thereby forming a glycan-containing solution;

optionally, removing excess dye using fresh beads; washing beads, separating the beads from excess dye/wash solution; and eluteing glycans from the beads; and collecting the glycan-containing solution.

In certain embodiments, the glycan solution may be stored for future use according to instructions provided, or analyzed for its glycan profile using a CE analyzer or uPLC analyzer or a combination thereof.

In certain embodiments, the kit further comprises instructions for covalently bonding the compound to the analyte. In certain embodiments, the kit further comprises one or more of the following: a buffering agent, a purification medium, a vial comprising the analyte, or an organic solvent.

Certain embodiments provide a kit for detecting an analyte in a sample, wherein the kit comprises:

a) a compound according to Formula (I), Formula (II), Formula (III), Formula (IV) or Formula (V); and b) instructions for detecting an analyte in the sample according to one or more of the methods described herein.

Certain embodiments provide a kit for detecting an analyte in a sample, wherein the kit comprises:

a) a composition comprising a compound according to Formula (I), Formula (II), Formula (III), Formula (IV) or Formula (V); and b) instructions for detecting an analyte in the sample according to one or more of the methods described herein.

Certain embodiments provide a kit for labeling and/or detecting a glycans in a sample, wherein the kit comprises:

a) a compound according to Formula (I), Formula (II), Formula (III), Formula (IV) or Formula (V); and b) instructions for labeling and/or detecting a glycans in a sample according to one or more of the methods described herein.

Certain embodiments provide a kit for labeling and/or detecting a glycans in a sample, wherein the kit comprises:

a) a composition comprising a compound according to Formula (I), Formula (II), Formula (III), Formula (IV) or Formula (V); and b) instructions for labeling and/or detecting a glycans in a sample according to one or more of the methods described herein.

Various ancillary materials will frequently be employed in an assay in accordance with the present disclosure. In an exemplary embodiment, buffers and/or stabilizers are present in the kit components. In another exemplary embodiment, the kits comprise indicator solutions or indicator "dipsticks", blotters, culture media, cuvettes, and the like. In yet another exemplary embodiment, the kits comprise indicator cartridges (where a kit component is bound to a solid support) for use in an automated detector. In another exemplary embodiment, the kit further comprises molecular weight markers, wherein said markers are selected from phosphorylated and non-phosphorylated polypeptides, calcium-binding and non-calcium binding polypeptides, sulfonated and non-sulfonated polypeptides, and sialylated and non-sialylated polypeptides. In another exemplary embodiment, the kit further comprises a member selected from a fixing solution, a detection reagent, a standard, a wash solution, and combinations thereof.

A detailed description of the present teachings having been provided above, the following examples are given for the purpose of illustrating the teachings and shall not be construed as being a limitation on the scope of the disclosure or claims.

EXAMPLES

Example 1: Synthesis and Preparation of Dye Compounds Comprising a Sulfonate Group FIG. 1 depicts an exemplary synthesis scheme for preparing dye compounds provided herein comprising a molecule containing a sulfonates group. In this exemplary scheme, L-cysteic acid (Compound 8, 3 mg) and N,N-diisopropylethylamine (DIEA) (5 µL) were dissolved in DMF (1 mL) to which Compound 7 was added. The reaction was stirred overnight. The cloudy orange mixture turned clear. The reaction mixture was purified by RP-column with water/Methanol to yield Compound 9 as a red powder after lyophilization.

Compound 9 (20 mg) was dissolved in DMF (1 mL). DIEA (10 µL) and di(N— succinimidyl)carbonate (DSC) (6 mg) were added into the solution. The reaction was stirred for 1 hour when thin-layer chromatography (TLC) showed the reaction was complete. The reaction mixture was added into diethyl ether (10 mL). The precipitated product, Compound 10, was collected after centrifugation.

Compound 10 (15 mg) was added into the solution of tert-butyl carbazate (Compound 11.2 mg) and DIEA (10 µL) in DMF (1 mL). The reaction was stirred for 1 hour. The reaction mixture was purified by RP-column with water-Methanol to yield t-boc protected Compound 1 which was dissolved in 2 mL of methanol followed by addition of 0.5 mL of concentrated HCl. The reaction was stirred for 1 hour. The reaction mixture was purified by RP-column with water-Methanol to afford Compound 1.

Figure 2:
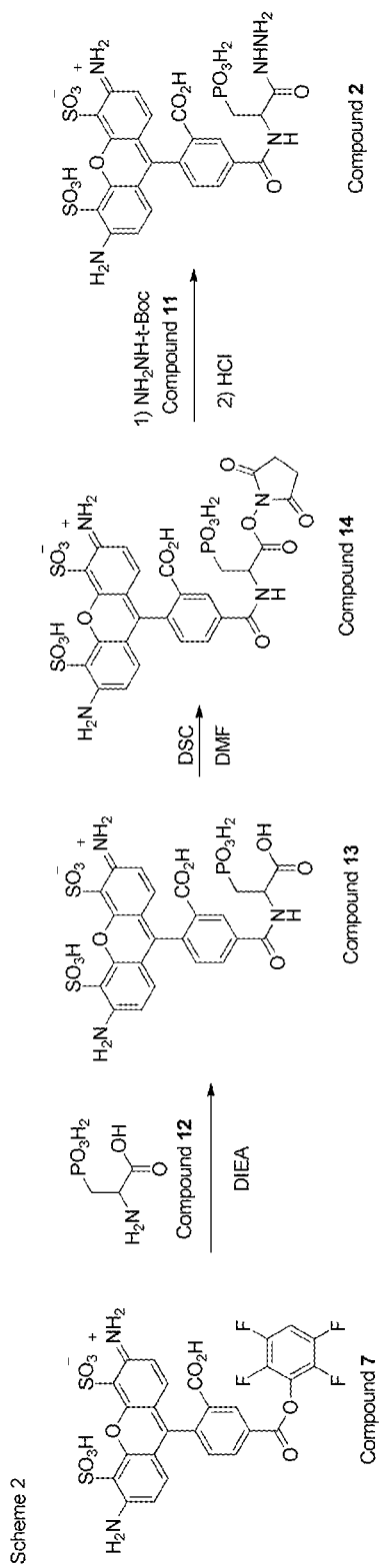
FIG. 2: Schematic of an exemplary synthesis scheme for the preparation of dye compounds comprising a phosphonate group according to certain embodiments disclosed herein.

Example 2: Preparation and Synthesis of Dye Compounds Comprising a Phosphonate Group FIG. 2 depicts an exemplary synthesis scheme for preparing dye compounds provided herein comprising a molecule containing a phosphonate group. In this exemplary scheme, DL-2-amino-β-phosphono propionic acid (Compound 12, 3 mg) and DIEA (5 µL) were dissolved in DMF (1 mL) to which Compound 7 (20 mg) was added. The reaction was stirred overnight. The cloudy orange mixture turned clear. The reaction mixture was purified by RP-column with water/Methanol to yield Compound 13 as red powder after lyophilization.

Compound 13 (20 mg) was dissolved in DMF (1 mL). DIEA (10 µL) and DSC (6 mg) were added into the solution. The reaction was stirred for 1 hour when TLC showed the reaction was complete. The reaction mixture was added into diethyl ether (10 mL). The precipitated product, Compound 14, was collected after centrifugation.

Compound 14 (13 mg) was added into the solution of tert-butyl carbazate (Compound 11, 2 mg) and DIEA (10 µL) in DMF (1 mL). The reaction was stirred for 1 hour. The reaction mixture was purified by RP-column with water-Methanol to yield t-boc protected Compound 2 which was dissolved in 2 mL of methanol to which 0.5 mL of concentrated HCl was added. The reaction was stirred for 1 hour. The reaction mixture was purified by RP-column with water-Methanol to afford the desired Compound 2.

Figure 3:
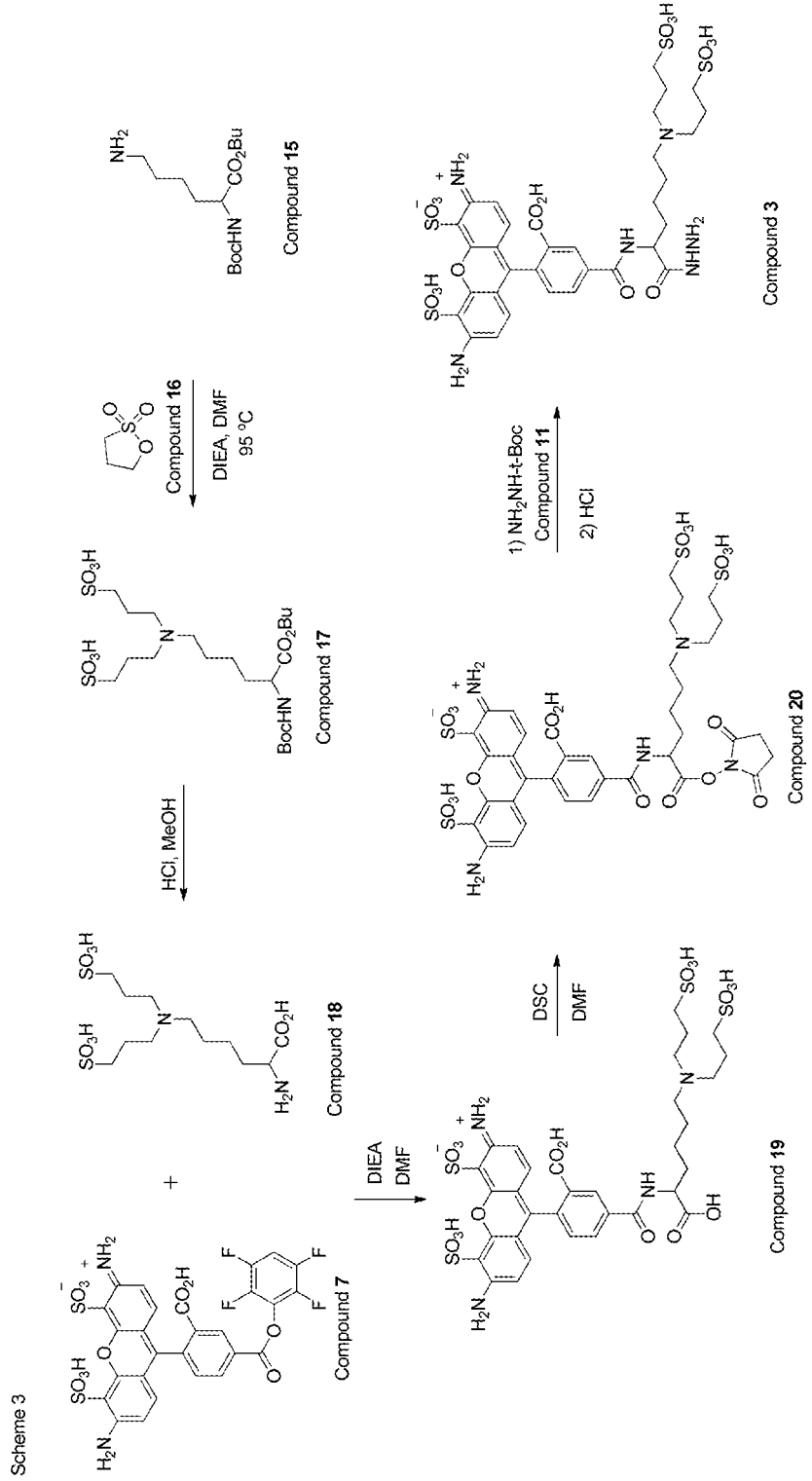
FIG. 3: Schematic of an exemplary synthesis scheme for the preparation of dye compounds comprising a multiple sulfonate groups according to certain embodiments disclosed herein.

Example 3: Synthesis and Preparation of Dye Compounds Comprising Multiple Sulfonate Groups FIG. 3 depicts an exemplary synthesis scheme for preparing dye compounds provided herein comprising a molecule containing multiple sulfonates groups. In this exemplary scheme, N-Boc-L-lysine tert-butyl ester (Compound 15, 100 mg) was mixed with propane-sultone (Compound 16, 100 mg). The mixture was heated to 90° C. for 1 hour. After cool down, the mixture was dissolved in DMF and purified by RP-column with water-methanol to afford Compound 17. Compound 17 (120 mg) was dissolved in 4 mL of methanol, 0.5 mL of concentrated HCl was added. The reaction was stirred for 1 hour. The reaction mixture was purified by RP-column with water-Methanol to afford the desired Compound 18.

Compound 7 (30 mg) was added into the solution of Compound 18 (30 mg) and DIEA (20 μL) in 3 mL of DMF. The mixture was stirred overnight. The reaction mixture was purified by RP-column with water-Methanol to yield Compound 19. Compound 19 (30 mg) was dissolved in DMF (3 mL). DIEA (20 μL) and DSC (13 mg) were added into the solution. The reaction was stirred for 1 hour when TLC showed the reaction was complete. The reaction mixture was added into diethyl ether (10 mL). The precipitated product, Compound 20, was collected after centrifugation.

Compound 20 (25 mg) was added into the solution of tert-butyl carbazate (5 mg) and DIEA (20 μL) in DMF (2 mL). The reaction was stirred for 1 hour. The reaction mixture was purified by RP-column with water-Methanol to yield t-boc protected Compound 5 which was dissolved in 2 mL of methanol to which 0.5 mL of concentrated HCl was added. The reaction was stirred for 1 hour. The reaction mixture was purified by RP-column with water-Methanol to afford the desired Compound 3.

Figure 4:
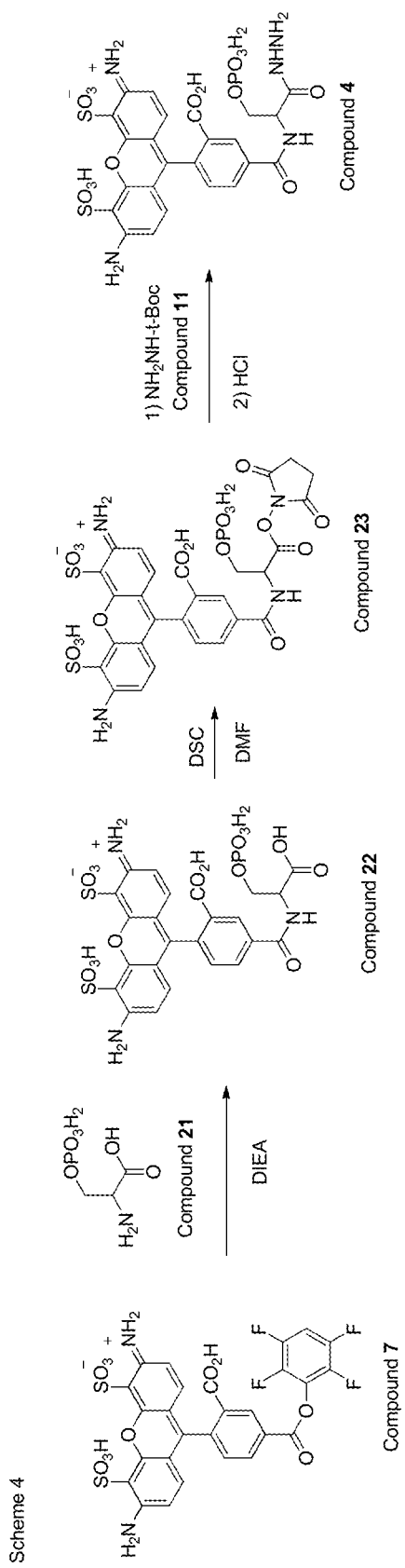
FIG. 4: Schematic of an exemplary synthesis scheme for the preparation of dye compounds comprising a phosphate group according to certain embodiments disclosed herein.

Example 4: Preparation and Synthesis of Dye Compounds Comprising a Phosphate Group FIG. 4 depicts an exemplary synthesis scheme for preparing dye compounds provided herein comprising a molecule containing a phosphate group. In this exemplary scheme, Compound 4 is prepared in a similar manner as described in Example 1 starting from Compound 7 and O-phospho-L-serine, Compound 21.

Figure 5:
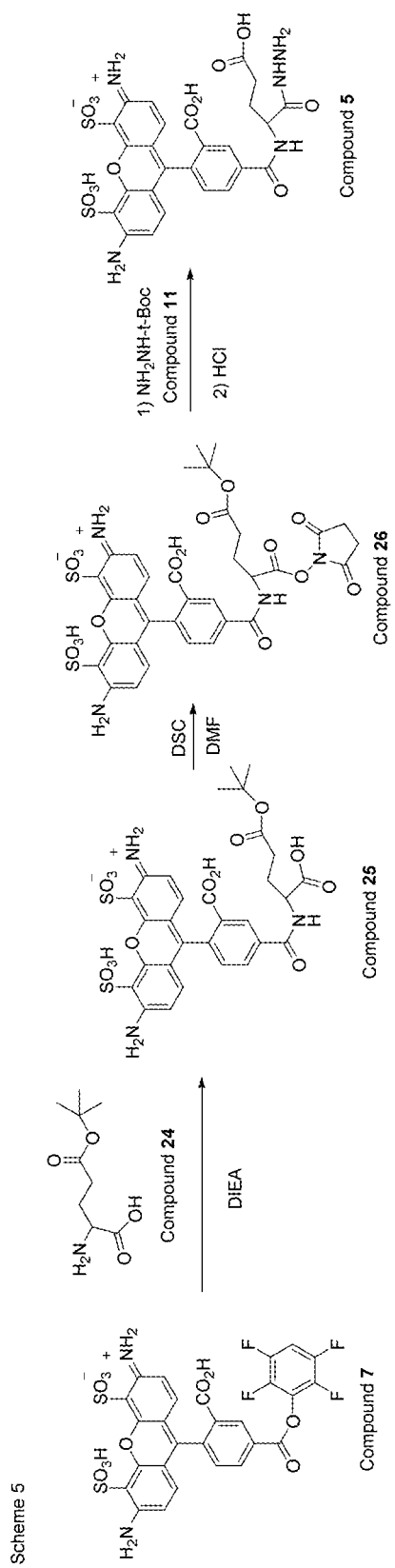
FIG. 5: Schematic of an exemplary synthesis scheme for the preparation of dye compounds comprising a carboxyl group according to certain embodiments disclosed herein.

Example 5: Preparation and Synthesis of Dye Compounds Comprising a Carboxyl Group FIG. 5 depicts an exemplary synthesis scheme for preparing dye compounds provided herein comprising a molecule containing a carboxyl group. In this exemplary scheme, Compound 5 is prepared in a similar manner as described in Example 1 starting from Compound 7 and L-glutamic acid 5-tert-butyl ester, Compound 24.

Figure 6:
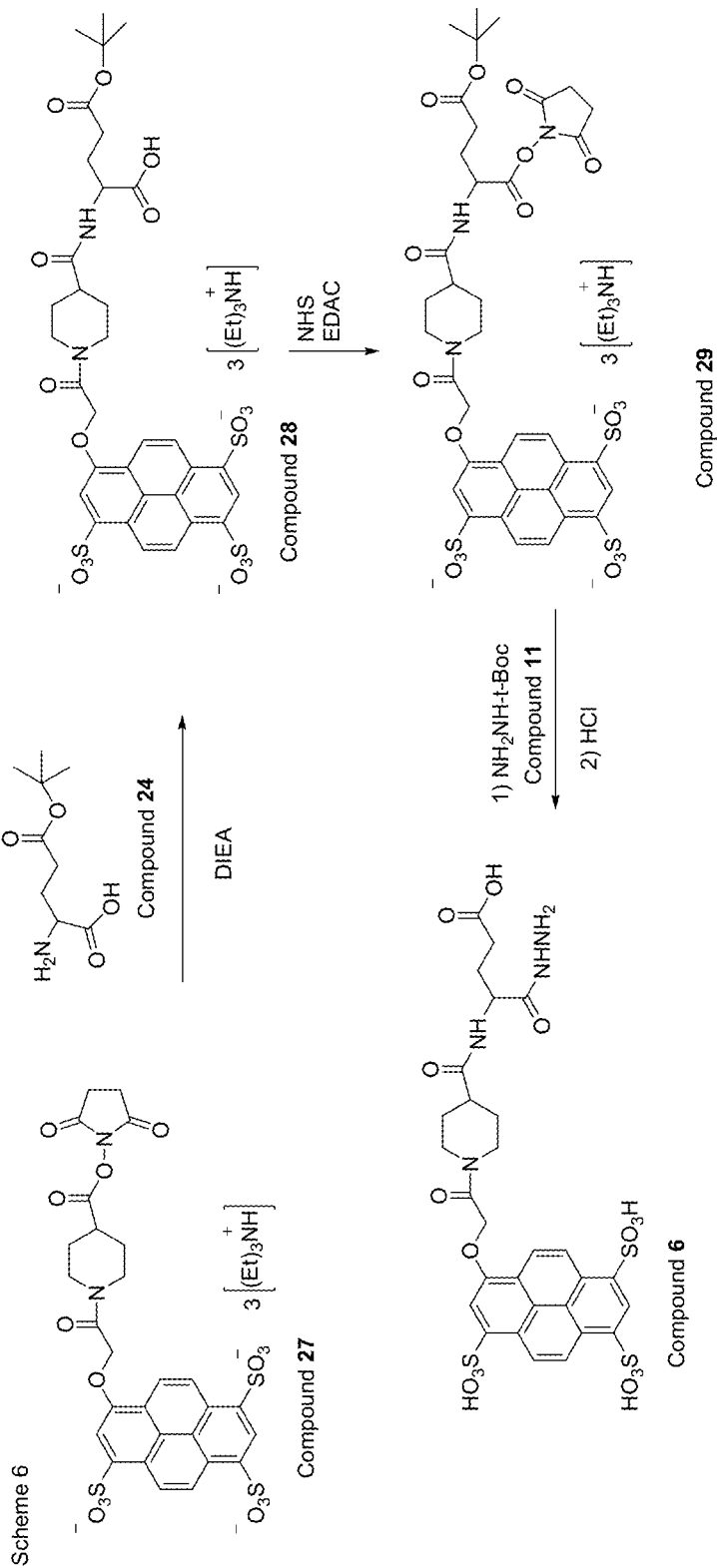
FIG. 6: Schematic of an exemplary synthesis scheme for the preparation of dye compounds comprising a carboxyl group according to certain embodiments disclosed herein.

Example 6: Preparation and Synthesis of Dye Compounds Comprising a Carboxyl Group FIG. 6 depicts an exemplary synthesis scheme for preparing dye compounds provided herein comprising a molecule containing a carboxyl group. In this exemplary scheme, Compound 6 is prepared in a similar manner as described in Example 5 starting from Compound 27 and L-glutamic acid 5-tert-butyl ester, Compound 24.

Example 7: Preparation and Synthesis of Compound 30

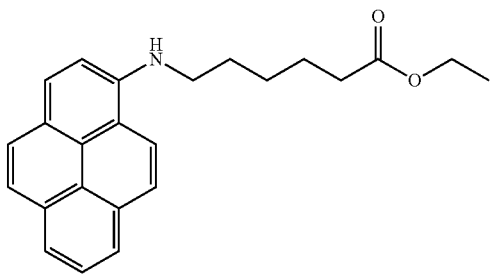 [SMILES: CCOC(=O)CCCCCNc1ccc2ccc3cccc4ccc1c2c34]

Aminopyrene (MW=219.28) was mixed with ethyl 6-bromohexanoate (1.4 eq, MW=233.11) in DMF with diisopropylamine (4.5 eq, 129.24). The solution was heated at reflux for 24 hour under Ar. The DMF was removed and the crude product is dissolved in ethyl acetate and washed with sodium bicarbonate. The solution was dried and recrystallized from hot ethyl acetate/hexane in two crops to give the ethyl 6-(pyren-1-ylamino)hexanoate. $H^1$NMR (CDCl$_3$): δ 7.7-8.2 (m, 6H), 4.15 (t, 2H), 2.35 (m, 2H), 1.71 (m, 2H), 1.62 (m, 2H), 1.34 (m, 2H).

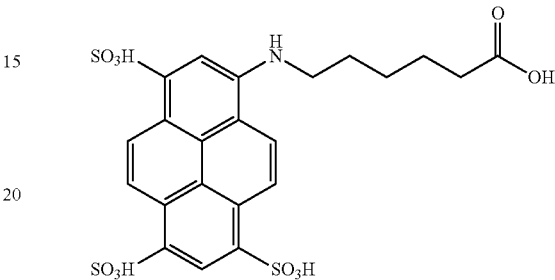

Ethyl 6-(pyren-1-ylamino)hexanoate was then reacted with cold fuming sulfuric acid, warmed to room temperature and stirred 24 hours. The reaction was quenched on ice, the solution neutralized with sodium hydroxide, desalted, and ion exchanged on a C18 column with 0.1M TEAB to give the 6-((3,6,8-trisulfopyren-1-yl)amino)hexanoic acid TEA salt. $H^1$NMR (D$_2$O): δ 9.00 (s, 1H), 8.95 (d, 1H), 8.80 (d, 1H), 8.65 (d, 1H), 8.45 (d, 1H), 8.00 (s, 1H), 3.42 (t, 2H), 2.20 (t, 2H), 1.70 (m, 2H), 1.55 (m, 2H), 1.32 (m, 2H).

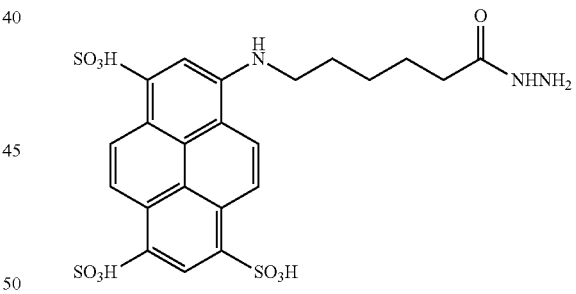

6-((3,6,8-trisulfopyren-1-yl)amino)hexanoic acid was then reacted with PyBOP (1 eq; MW=520.39) and hydrazine (1 eq; MW=32.05) in DMF with diisopropylamine (1.2 eq; MW=129.24) for 10 min. The DMF solvent was removed, re-dissolved in water and washed with ethyl acetate. The water layer, upon concentration, was purified on a large C18 column with MeOH/water to 8-((6-hydrazinyl-6-oxohexyl)amino)pyrene-1,3,6-trisulfonic acid as an amber/grey foamed solid. $H^1$NMR (D$_2$O): δ 9.13 (s, 1H), 9.05 (d, 2H), 8.96 (d, 2H), 8.80 (d, 2H), 8.52 (d, 2H), 8.0 (s, 2H), 3.0 (t, 2H), 3.32 (m, 2H), 2.16 (m, 2H), 1.50-1.7 (m, 4H0, 1.32 (m, 2H). MS M−H: 584.2; UVmax=465 nm, Fluorescence max=525 nm, The synthesis scheme is shown below.

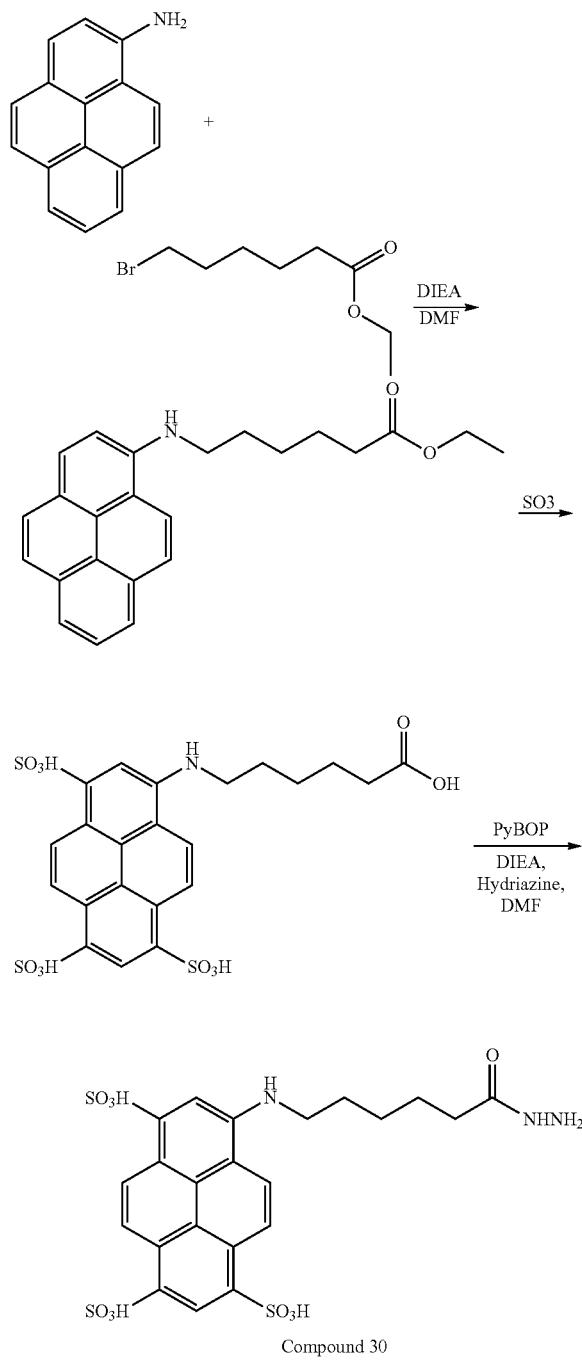

Compound 30

Figure 7A:
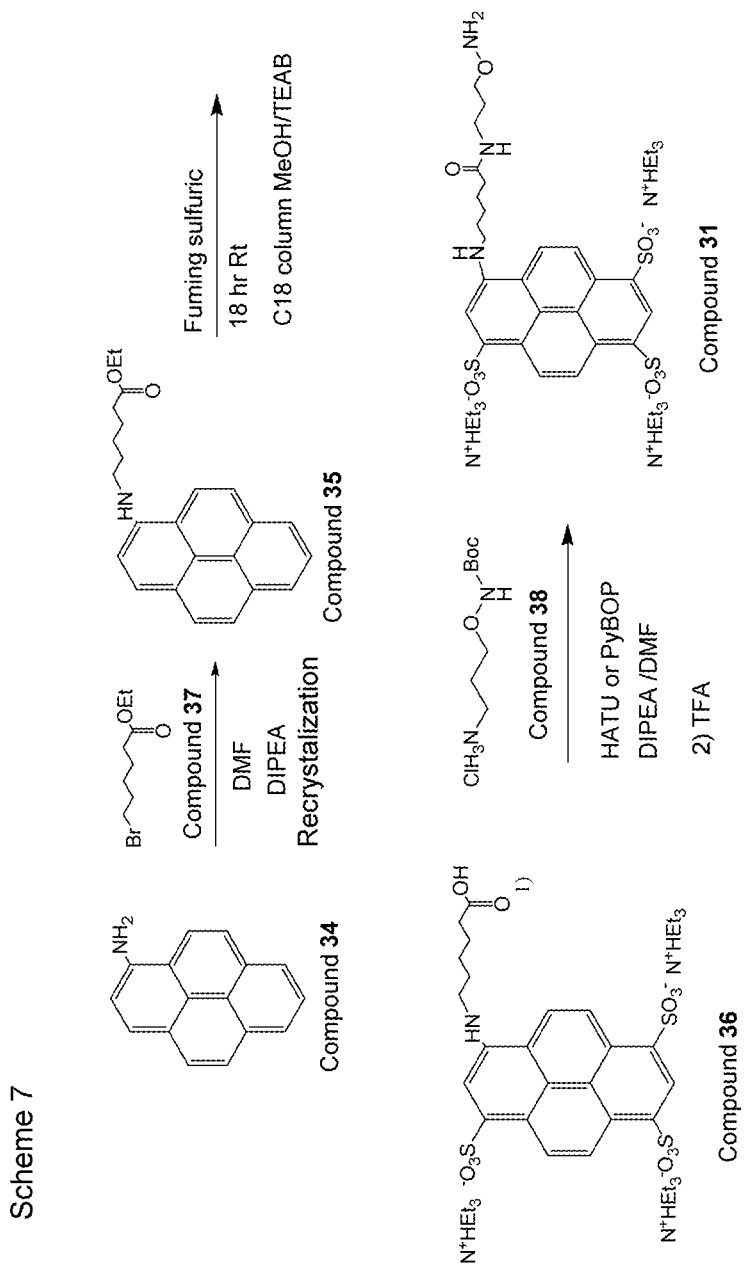
FIG. 7A: Schematic of an exemplary synthesis scheme for the preparation of Compound 31 according to certain embodiments disclosed herein.

Example 8: Preparation and Synthesis of Dye Compounds Comprising an Aminooxy Group FIG. 7A depicts an exemplary synthesis scheme for preparing dye compounds provided herein comprising a molecule containing an aminooxy group. In this exemplary scheme, Compound 31 is prepared by mixing compound 36 (previously described) with tert-butyl N-(3-aminopropoxy) carbamate hydrochloride (MW=227, 1.5 eq) and diisopropylethylamine (MW=129, 8 eq) in DMF and is cooled in an ice bath. To this was added HATU (MW=379, 1.5 eq) and the reaction was stirred for 10 min. The DMF was removed to yield a brown residue. A solution of TFA and DCM (1:1) was cooled in an ice bath and then added to the residue, also in an ice bath. This was stirred for 30 min. The TFA/DCM was removed and the resulting brown residue was dissolved in 50 mL water, washed 3×50 mL ethyl acetate, and the water layer concentrated to dryness. The resulting solid was purified on C18 column using 0%-15%-20% MeOH/0.1 M triethylammonium acetate. The pure fractions were desalted on a pad of C18 to yield Compound 31 (50%) as a yellow/amber resin: m/z (negative ion) expected 642.09; found 642.01.

Figure 7B:
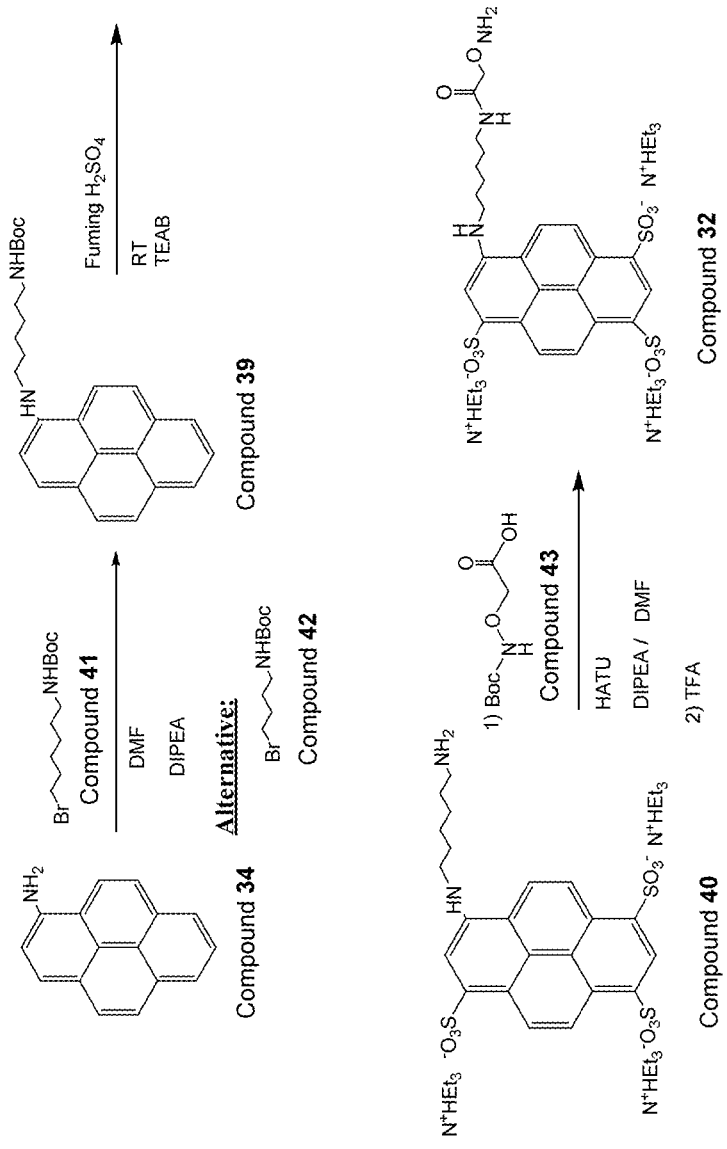
FIG. 7B: Schematic of an exemplary synthesis scheme for the preparation of Compound 32 according to certain embodiments disclosed herein.

FIG. 7B depicts an exemplary synthesis scheme for preparing dye compounds provided herein comprising a molecule containing an aminooxy group. In this exemplary scheme, Compound 32 is prepared as follows: Compound 39 is prepared by refluxing aminopyrene compound 34 with tert-butyl (6-bromohexyl)carbamate (MW=280, 1.4 eq) and diisopropylethylamine (MW=129, 4.5 eq) in anhydrous DMF for 23 hrs. The DMF was removed, the residue dissolved in DCM, washed with 5% sodium bicarbonate, dried over anhydrous sodium sulfate, and the DCM removed. The residue was purified by flash column chromatography (20-25% ethyl acetate/hexane) and then further purified by recrystallization from ethyl acetate/hexane to yield a golden-yellow crystal (17%).

Compound 40 is prepared by reacting compound 39 with ice cold fuming sulfuric acid, warming to room temperature, and stirring for 1 hr. The reaction solution is poured over ice, neutralized to pH 7, and desalted using a C18 pad. The resulting amber solid is purified by C18 column chromatography using 0%-10%-15% MeOH/0.1M triethylammonium acetate. The pure fractions are desalted on a C18 pad to yield a yellow solid (47%).

Compound 32 is prepared by mixing compound 40 with (tert-butoxycarbonyl)aminooxy acetic acid (MW=191, 1.4 eq), and diisopropylethylamine (MW=129, 8 eq) in DMF. The reaction solution was cooled in an ice bath. To this was added HATU (MW=379, 1.5 eq) and the reaction was stirred for 10 min. at 5° C. The DMF was removed and the amber resin was purified by C18 column chromatography using 0%-40% MeOH/0.1 M triethylammonium bicarbonate. The pure fractions were concentrated to dryness. A solution of TFA and DCM (1:1) was cooled in an ice bath and then added to the residue, also in an ice bath. This was stirred for 30 min. at 5° C. and then 30 min at room temperature. The solvent was removed to yield a yellow solid (93%); m/z (negative) expected 628.07, found 628.11.

Figure 7C:
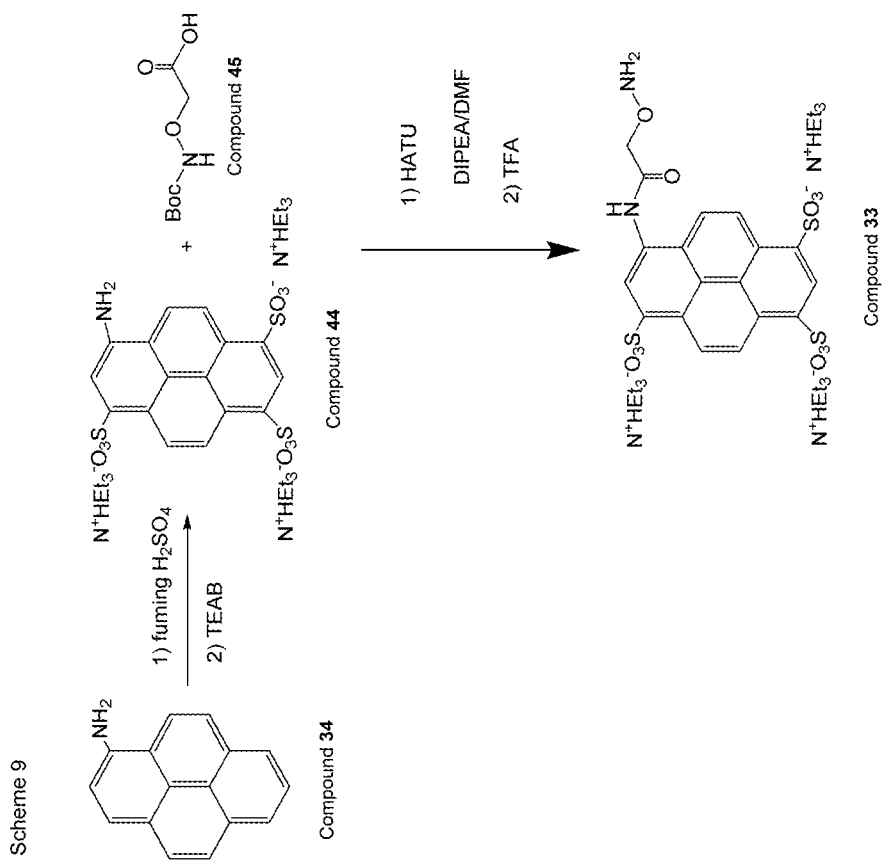
FIG. 7C: Schematic of an exemplary synthesis scheme for the preparation of Compound 33 according to certain embodiments disclosed herein.

FIG. 7C depicts an exemplary synthesis scheme for preparing dye compounds provided herein comprising a molecule containing an aminooxy group. In this exemplary scheme, Compound 33 is prepared.

Example 9: Method of Labeling and Detecting Glycans

IgG was purified from media using the POROS Protein A MABCAPTURE resin (Life Technologies, Carlsbad, Calif.). N-linked glycans were enzymatically removed with PNGase F and glycans were purified using graphite carbon SPE. Glycans were labeled with APTS using standard reductive amination (DMSO/15% acetic acid/1M sodium cyanoborohydride) and then dried, or with Compound 30 or Compound 1 in 0.1% acetic acid with no drying. Labeled glycans were purified using BIORAD BIOGEL P2 size exclusion chromatography (Bio-Rad, Hercules, Calif.). Glycans were analyzed using a 3500 GENETIC ANALYZER (Life Technologies, Carlsbad, Calif.) (see, co-owned, co-pending U.S. Provisional Patent Application Ser. No. 62/087,208, titled "Charged Reactive Oligomers" and PCT Patent Application No. PCT/US2015/063791, titled "Charged Reactive Oligomers, each of which is herein incorporated by reference in its entirety). Glycans were identified by retention time relative to the LIZ600 DNA size standard ladder. Glycans were quantified using 100 pmole maltohexose (M6) and/or maltopentose (M5) internal standards, when applicable.

Existing fluorescent labeling of glycans involves reductive amination with APTS. The dye compounds provided herein using hydrazide chemistry significantly improve glycan labeling.

Figure 8A:
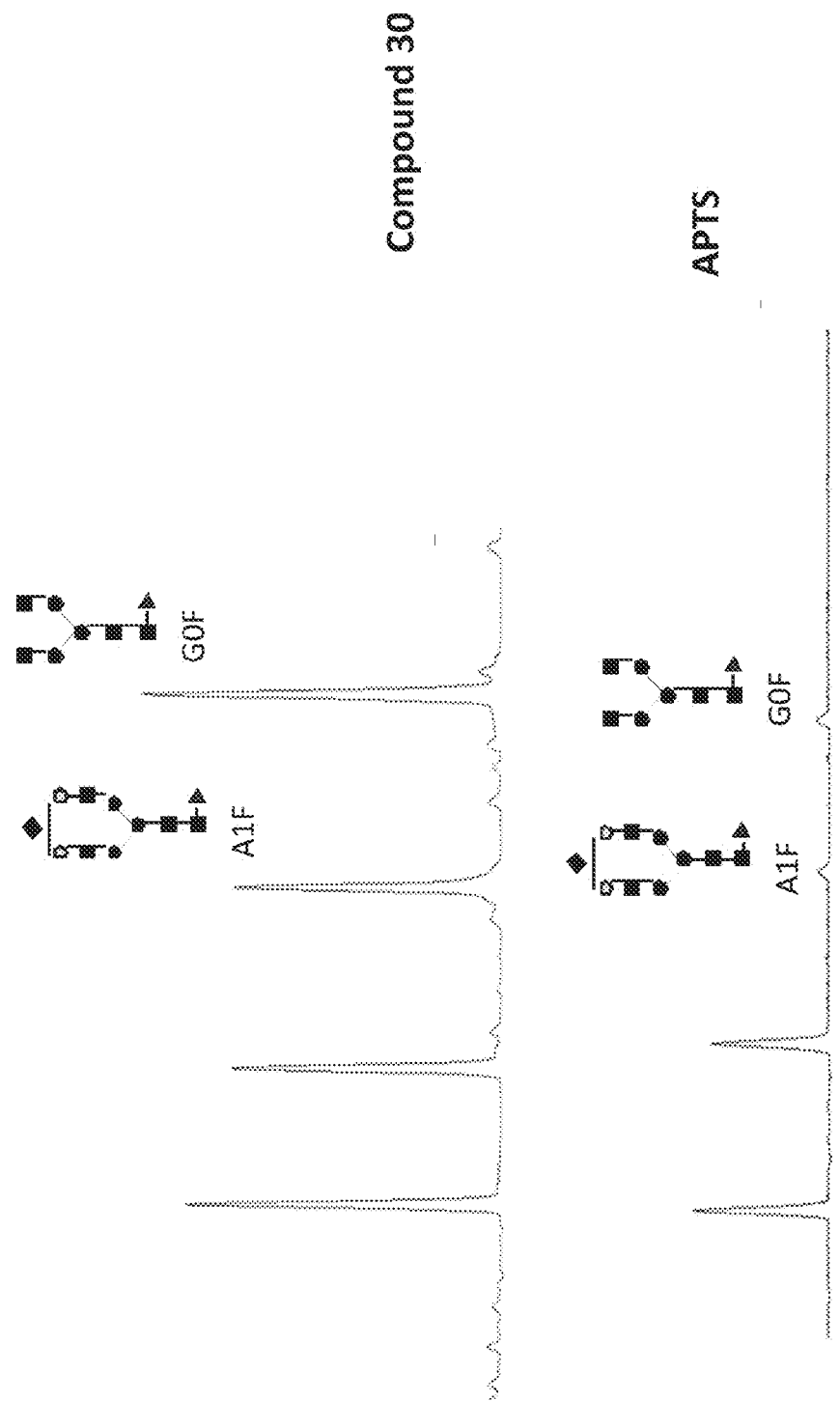
FIG. 8A: A representative electrophoretogram demonstrating Compound 30 more effectively labels glycans than APTS in methods according to certain embodiments disclosed herein.
Figure 8B:
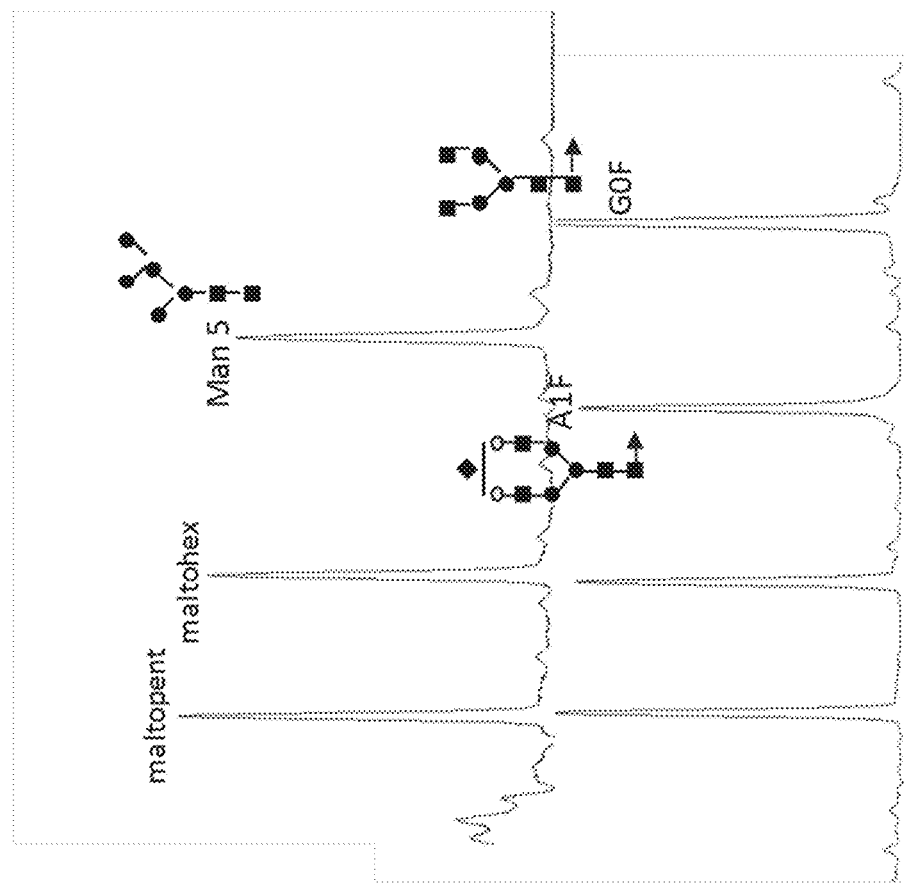
FIG. 8B: A representative electrophoretogram demonstrating Compound 30 allows for separation of Man 5 and A1F glycans in methods according to certain embodiments disclosed herein.
Figure 8C:
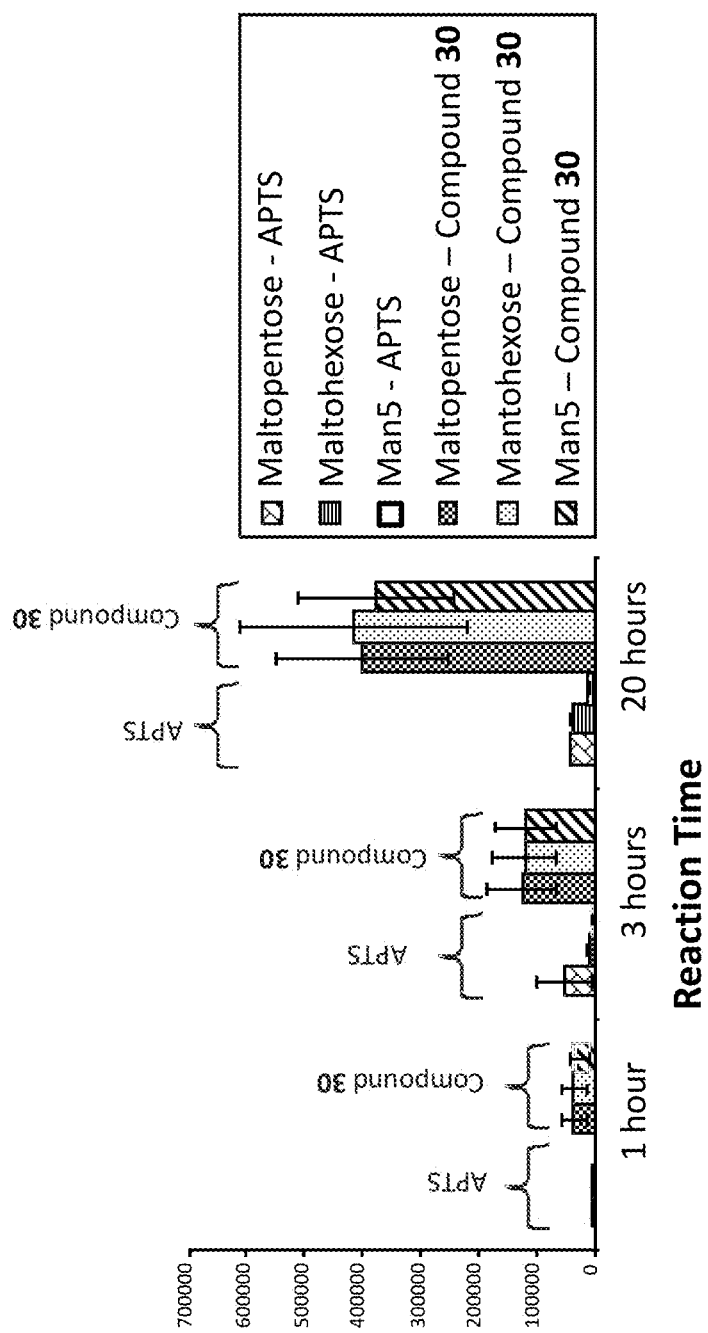
FIG. 8C: Comparison of reaction time using APTS and Compound 30 in methods according to certain embodiments disclosed herein.
Figure 9A:
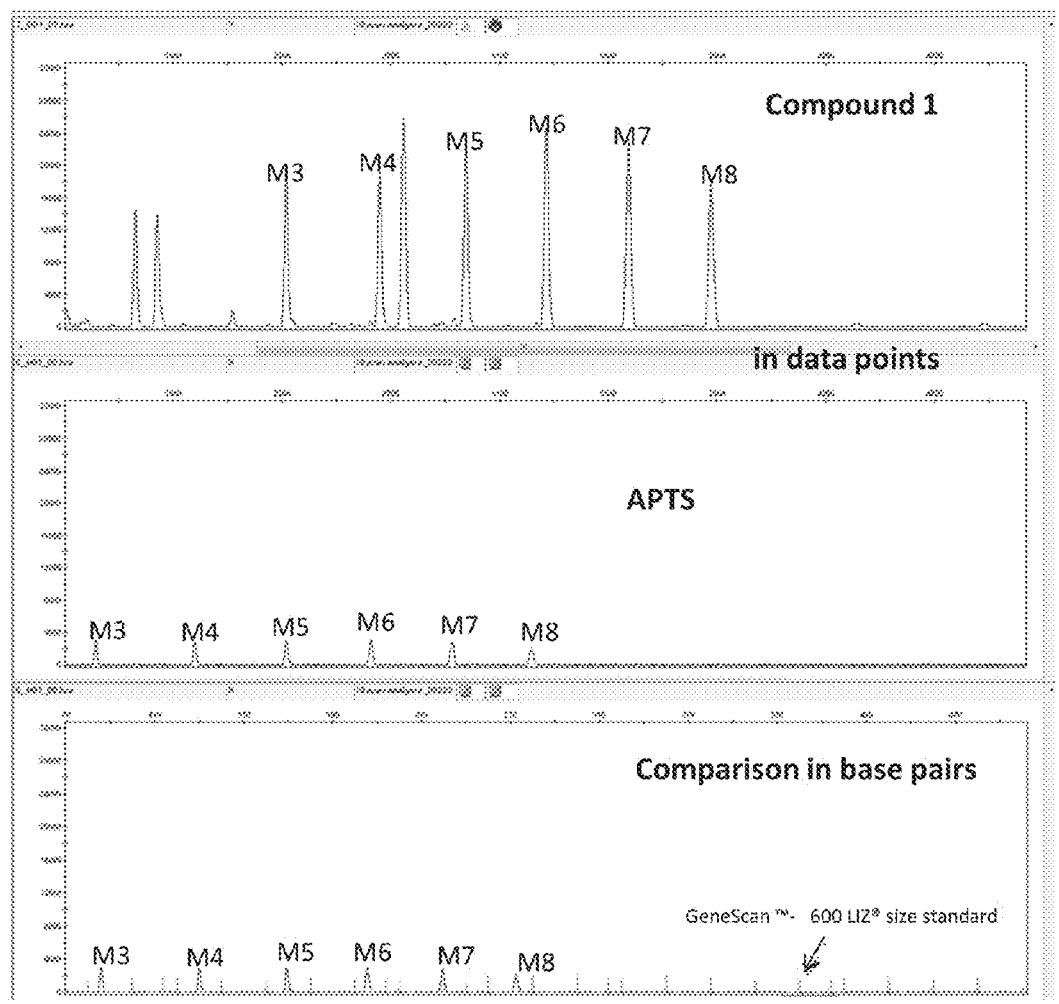
FIG. 9A: Representative electrophoretograms demonstrating a comparison between APTS (middle electrophoretogram) and Compound 1 (top electrophoretogram) reaction with maltose standards according to methods disclosed herein showing that one glucose unit separation between maltotriose (M3) to maltooctaose (M8). The bottom electrophoretogram shows the comparison in base pairs. The x-axis represents data points (e.g., migration time) or base pairs and the y-axis represents signal intensity (e.g., the output from the genetic analyzer).
Figure 9B:
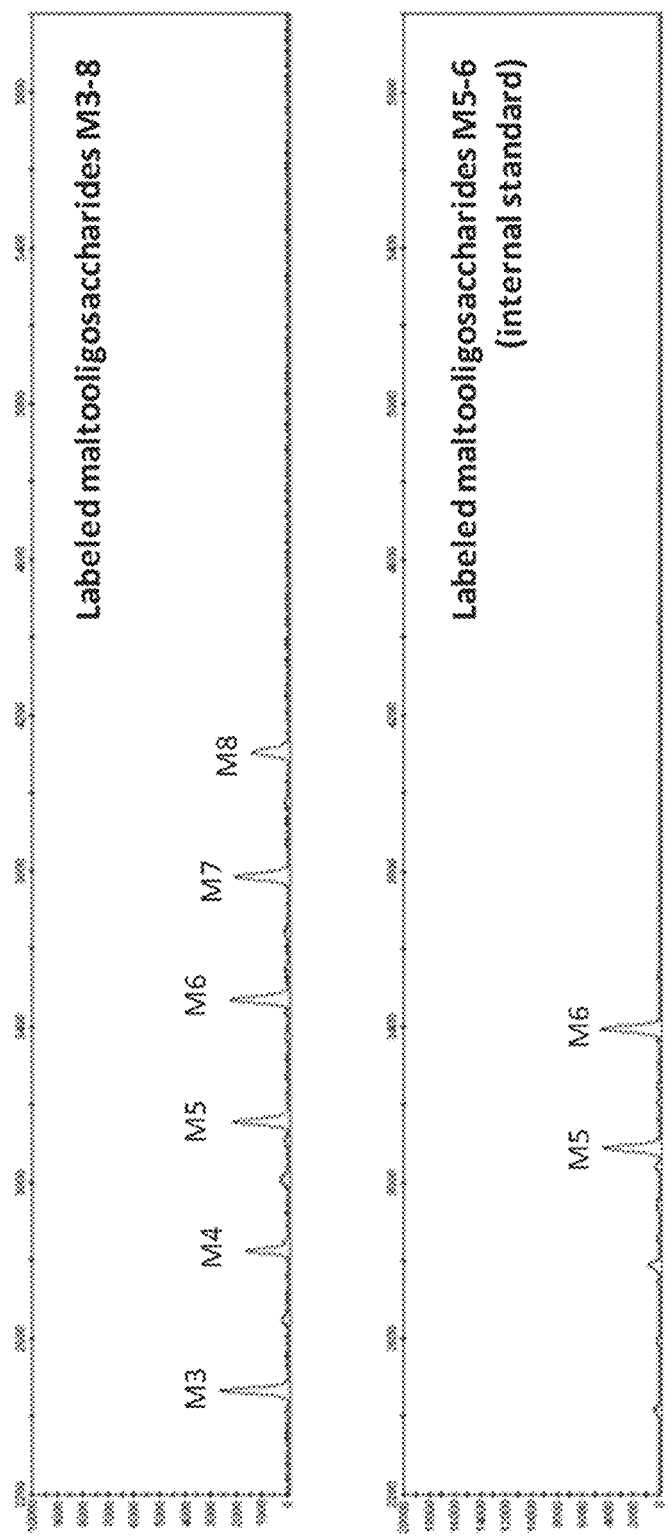
FIG. 9B: Representative electrophoretograms demonstrating a comparison in base pairs between APTS and Compound 1 reaction with maltooligosaccharides M3-M8 (top electrophoretogram) and maltooligosaccharides maltopentaose (M5) and maltohexaose (M6) (bottom electrophoretogram). The x- and y-axes are the same as indicated in FIG. 9A.
Figure 10A:
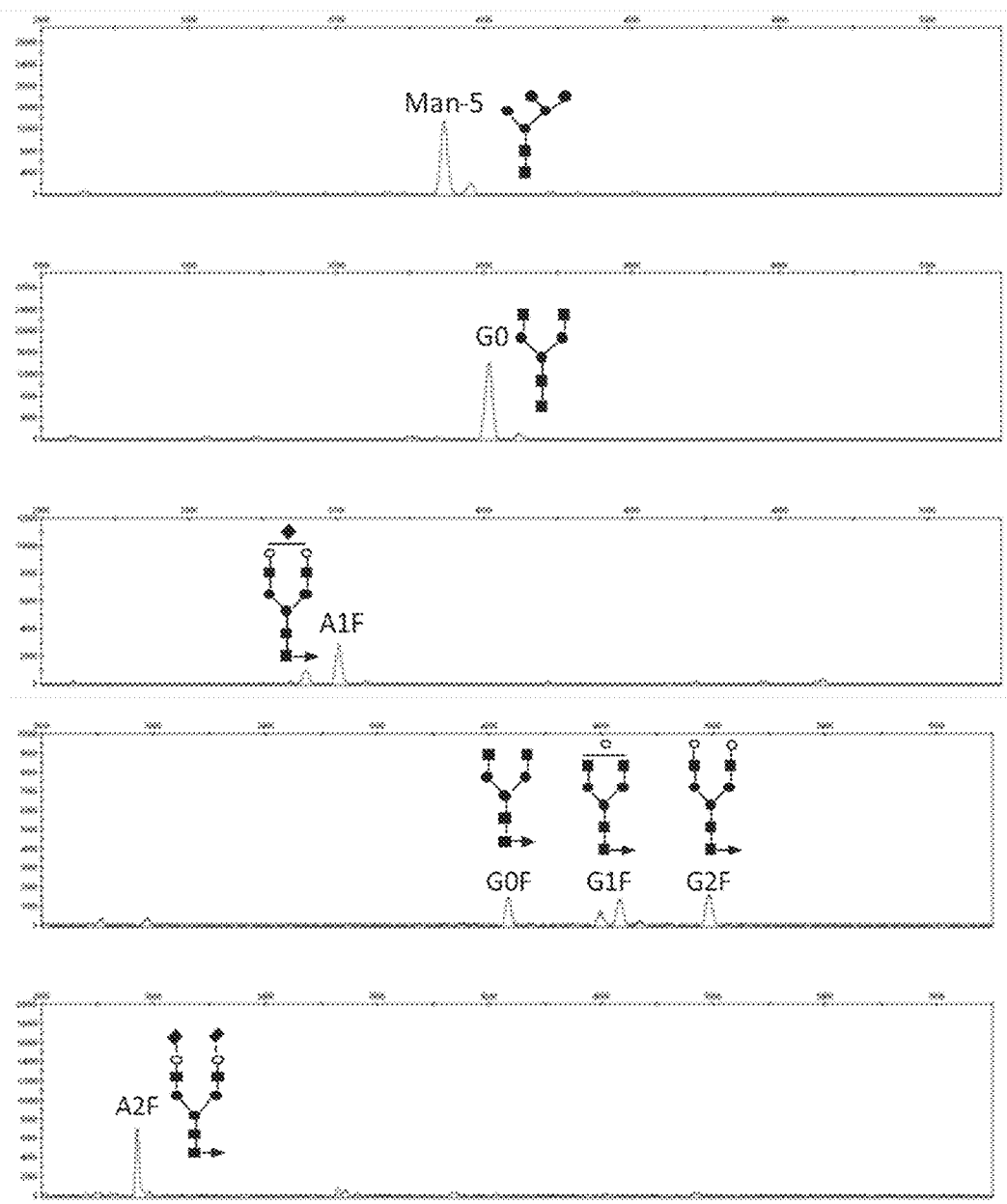
FIG. 10A: Representative electrophoretogram showing labeling of several glycan standards (mixture of galactosylated and sialylated glycans) with Compound 1. Top=Man-5; Second=G0; Third=G0F, G1F and G2F; Bottom=A2F.
Figure 10B:
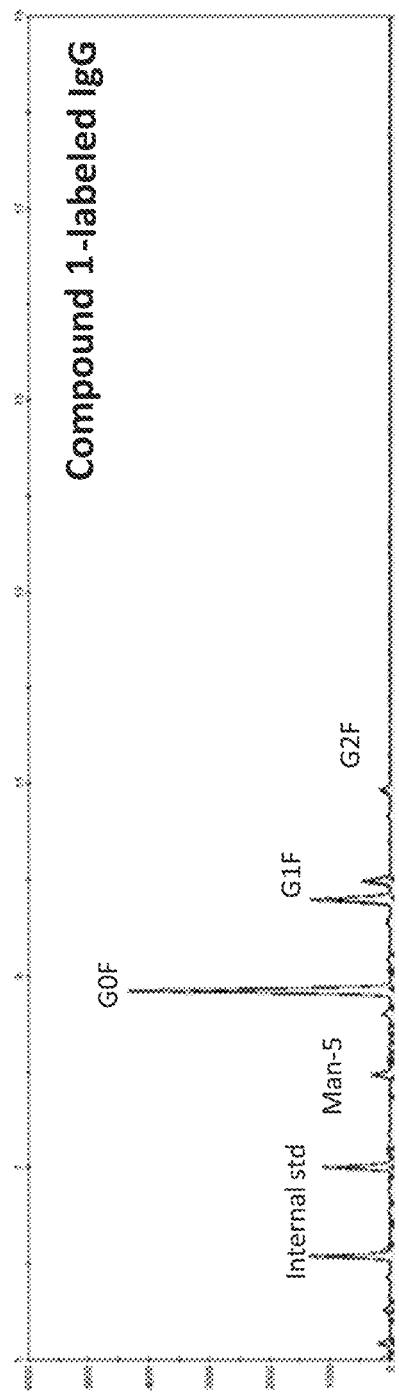
FIG. 10B: Capillary electrophoresis profile of an IgG sample labeled with Compound 1.
Figure 11A:
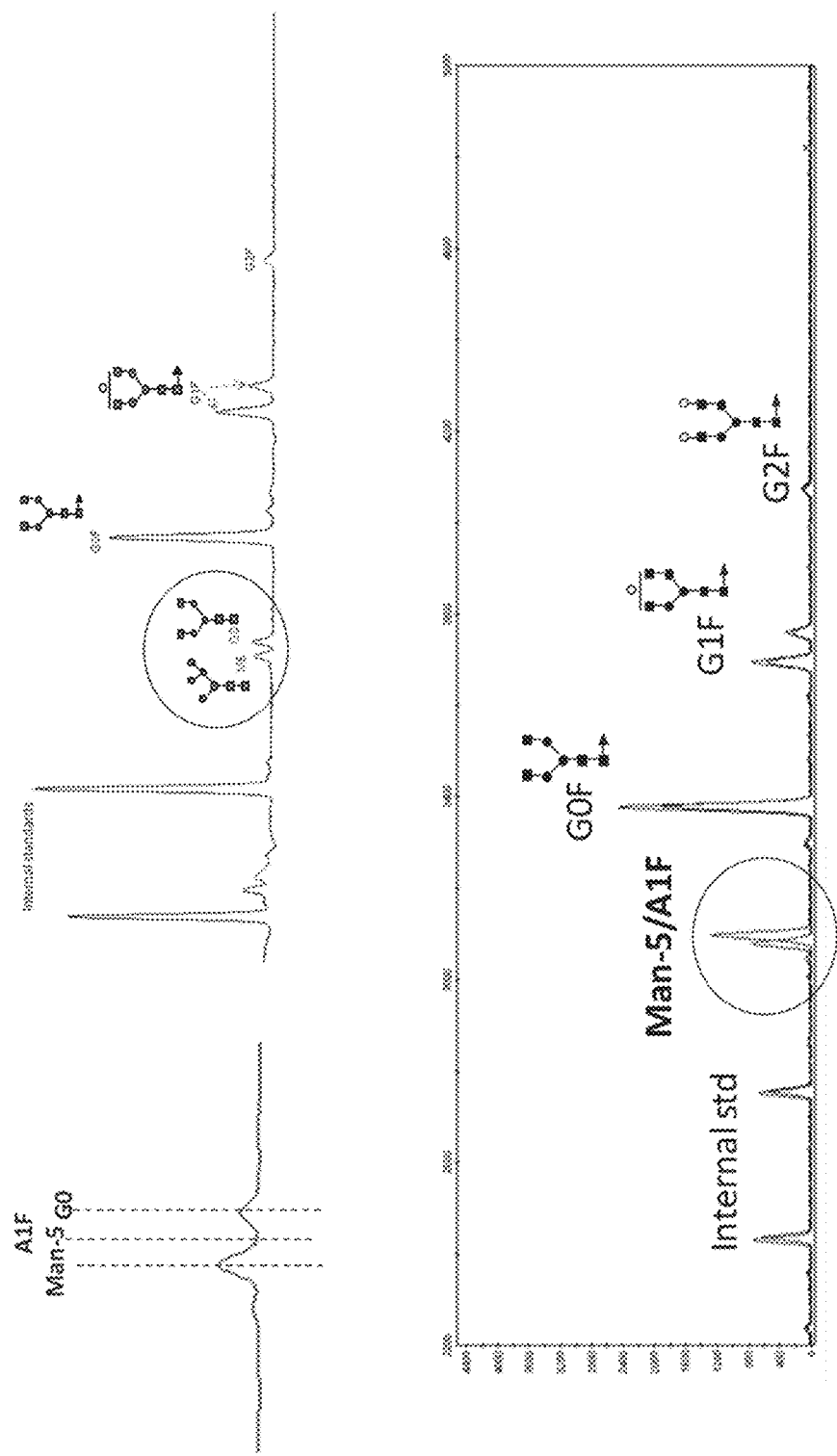
FIG. 11A: Representative electrophoretogram showing the lack of separation of eluting glycoforms, such as Man 5 and A1F (see circled portion) when APTS was used as the labeling reagent in methods according to certain embodiments disclosed herein.
Figure 11B:
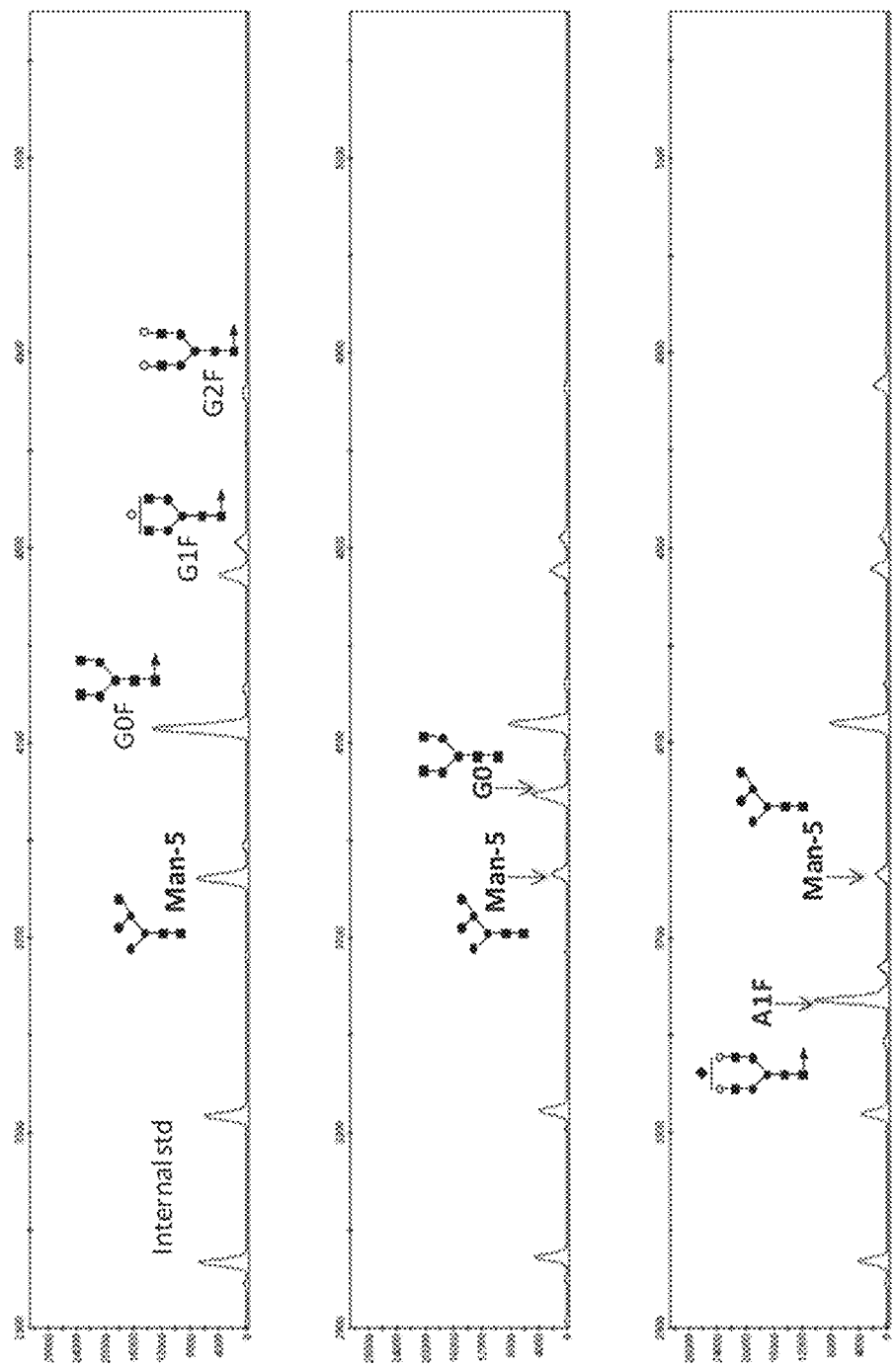
FIG. 11B: Representative electrophoretogram showing resolution of various glycoforms when the same sample from FIG. 11A was labeled with Compound 1 in methods according to certain embodiments disclosed herein.

As shown in FIGS. 8A, 8B and 8C, Compound 30 increased the sensitivity, reduced the labeling time, allowed for labeling under mildly acidic conditions and allowed for the separation of important glycoforms Man 5 and A1F (these glycoforms typically do not separate when labeled using existing dyes, such as APTS). As shown in FIGS. 9A and 9B, Compound 1 has increased signal intensity. When compared to APTS, the improvement in signal intensity was observed with using 1000 times less dye (µM for Compound 1 vs. mM for APTS). FIGS. 10A and 10B show labeling of several glycan standards, a mixture of galactosylated and sialylated glycans) with Compound 1 (FIG. 10A) and an IgG sample labeled with Compound 1 (FIG. 10B). FIGS. 11A and 11B demonstrate that the existing dyes (e.g., APTS) do not allow for the separation of closely eluting glycoforms, such as Man 5 and A1F.

The dye compounds provided herein allow for multiplexing by changing the charge state of the dye compound used. This ability increases the resolution and analytical diversity that can be analyzed by capillary electrophoresis, by allowing the dye compound to be tailored to the analyte. (See, co-owned, co-pending U.S. Provisional Patent Application Ser. No. 62/087,208, titled "Charged Reactive Oligomers" and PCT Patent Application No. PCT/US2015/063791, titled "Charged Reactive Oligomers, each of which is herein incorporated by reference in its entirety).

Example 10: Glycan Size Standards as Mobility Markers

Glycan peaks are identified by their relation to an internal size standard, also called mobility markers. Existing methods use a LIZ600 standard (Life Technologies, Carlsbad, Calif.) that is added to the glycan sample. The standard is detected in a different wavelength than the labeled glycan samples, thus enabling their simultaneous detection within the same run. However it is DNA-based so it is not an ideal marker. To overcome this challenge, glycan size standards (also termed mobility markers) were synthesized using hydrolyzed dextran and the dye compounds disclosed herein. Unlike current DNA size standards, the glycan size standards behave on the CE like labeled glycans and therefore can allow for improved alignment of glycan peaks. As shown in FIG. 12A, glycan size standards were synthesized using hydrolyzed dextran and Compound 1. The size standard ladder was prepared by fractionation using size-exclusion chromatography. These size standards were added to each glycan sample and run on a 3500 GENETIC ANALYZER (see, co-owned, co-pending U.S. Provisional Patent Application Ser. No. 62/087,208, titled "Charged Reactive Oligomers" and PCT Patent Application No. PCT/US2015/063791, titled "Charged Reactive Oligomers, each of which is herein incorporated by reference in its entirety). Using the glycan size standards, GENEMAPPER software aligned glycan peaks where the alignment % CV was less than 0.1%. FIG. 12B shows that the size standards were separated by one glucose unit, a common unit used for HPLC glycan analysis (middle electrophoretogram) and detected in a different channel than the labeled glycan sample.

We claim:

1. A compound selected from the group consisting of:

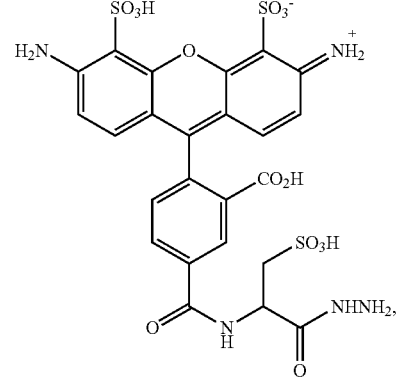

Compound 1

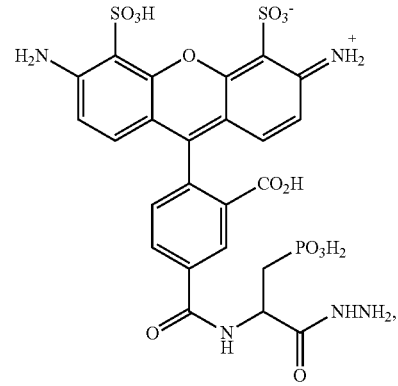

Compound 2

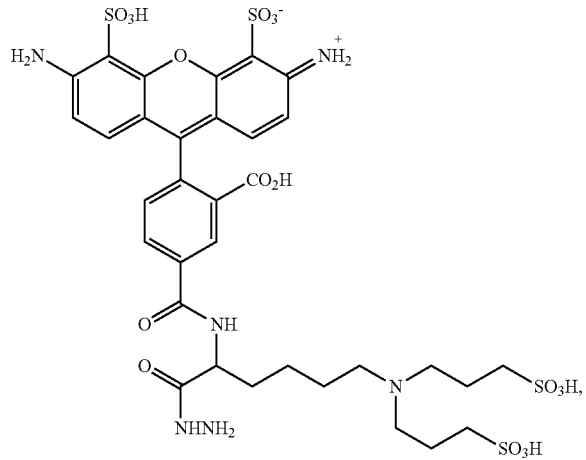

Compound 3

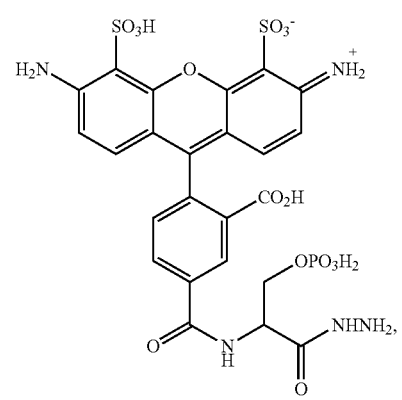

Compound 4

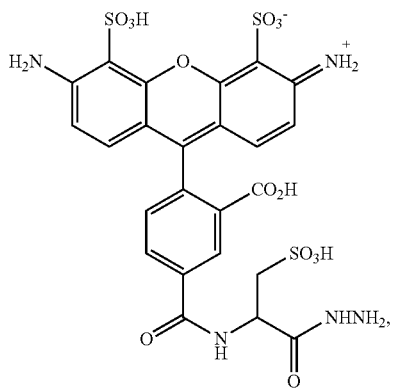

Compound 1

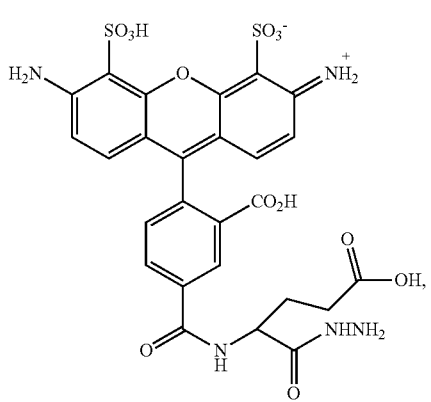

Compound 5

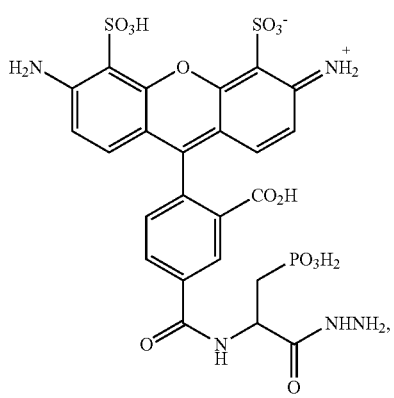

Compound 2 or a salt thereof.

2. The compound of claim 1, wherein the salt comprises a potassium, sodium, ammonium, alkylammonium, tetralkylammonium, triethylammonium, tert-butylammonium, tetralkyl-phosphonium, tetraaryl-phosphonium, lithium or cesium ion.

3. A composition comprising:
   (a) an analyte; and
   (b) a compound according to claim 1.

4. The composition of claim 3, further comprising a buffer solution.

5. The composition of claim 4, wherein the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus.

6. A method for determining the presence of an analyte of interest in a sample, wherein the method comprises:
   a) contacting the sample with a compound of claim 1;
   b) incubating the sample and the compound or composition for a sufficient amount of time to form a complex between the compound and analyte;
   c) illuminating the complex with an appropriate wavelength to form an illuminated complex; and
   d) detecting emissions from the illuminated complex, thereby determining the presence of the analyte.

7. A method for determining the presence of an analyte of interest in a sample, wherein the method comprises:
   a) contacting the sample with a compound selected from the group consisting of:

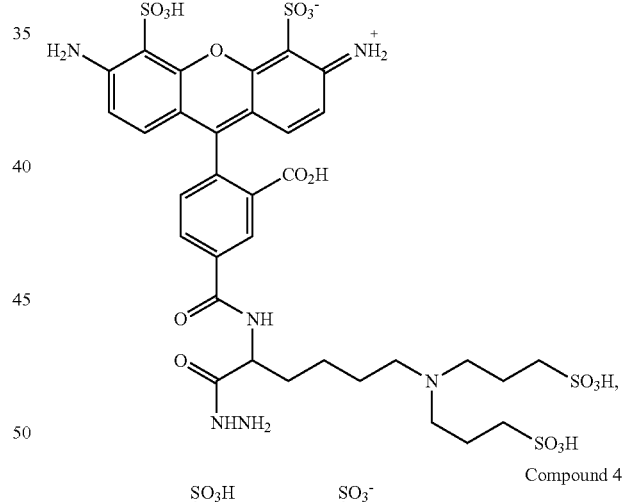

Compound 3

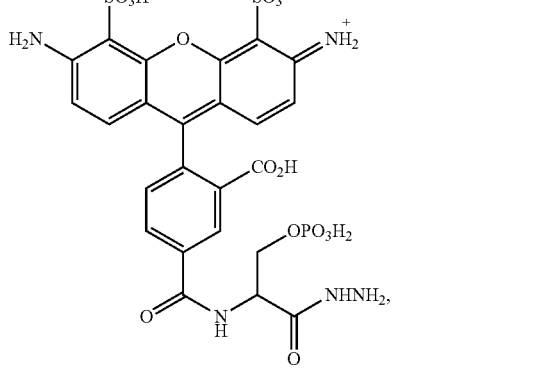

Compound 4

165

-continued

Compound 5

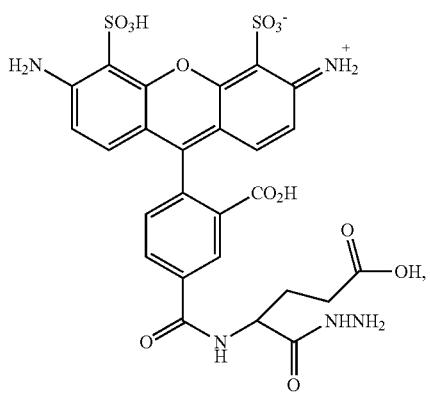

or a salt thereof;
b) incubating the sample and the compound or composition for a sufficient amount of time to form a complex between the compound and analyte;
c) illuminating the complex with an appropriate wavelength to form an illuminated complex; and
d) detecting emissions from the illuminated complex, thereby determining the presence of the analyte.

8. The method of claim 7, wherein the analyte and the compound are connected by a covalent bond.

9. The method of claim 8, wherein the compound becomes fluorescent after formation of the complex.

10. The method of claim 9, wherein the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus.

11. The method of claim 7, wherein the sample comprises live cells, intracellular fluids, extracellular fluids, biological fluids, biological fermentation media, environmental sample, industrial samples, proteins, peptides, buffer solutions biological fluids or chemical reactors.

12. The method of claim 7, wherein the sample comprises blood cells, immune cells, cultured cells, muscle tissue, neurons, extracellular vesicles; vascular tissue, blood fluids, saliva, urine; water, soil, waste water, sea water; pharmaceuticals, foodstuffs or beverages.

13. The method of claim 7, wherein the sample is immobilized on a polymeric membrane, within a polymeric gel, on a microparticle, on a microarray, on a silicon chip, on a glass slide, on a microwell plate, and on a microfluidic chip.

14. A method of detecting a glycan in a sample, the method comprising:
a) contacting the sample with a compound according to claim 1, or a composition according to claim 3;
b) incubating the sample and the compound or composition for a sufficient amount of time to form a complex between the compound and glycan;
c) illuminating the complex with an appropriate wavelength to form an illuminated complex; and
d) detecting emissions from the illuminated complex, thereby determining the presence of the glycan.

15. A method of detecting a glycan in a sample, the method comprising:
a) contacting the sample with a [a] compound selected from the group consisting of:

166

Compound 1

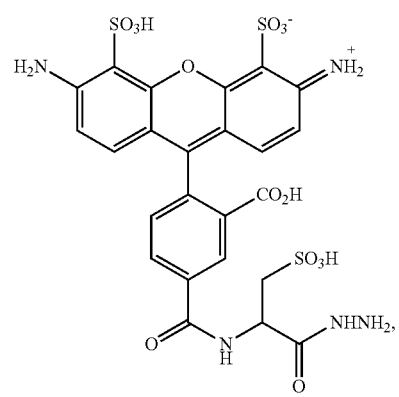

Compound 2

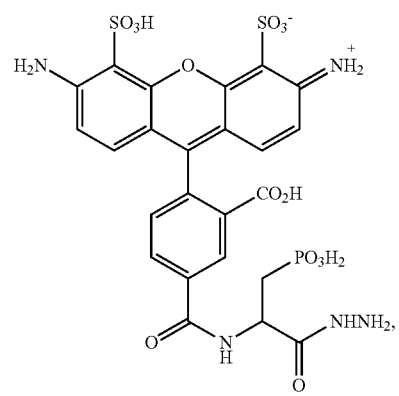

Compound 3

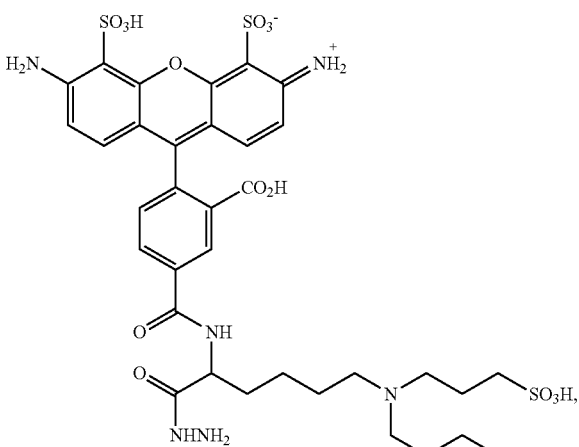

Compound 4

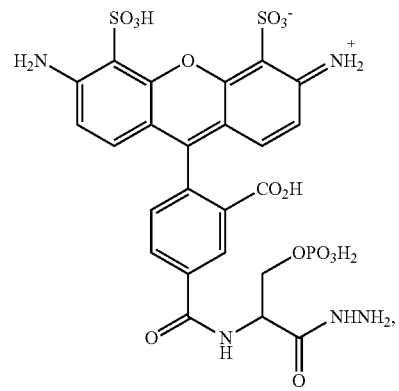

-continued

Compound 5
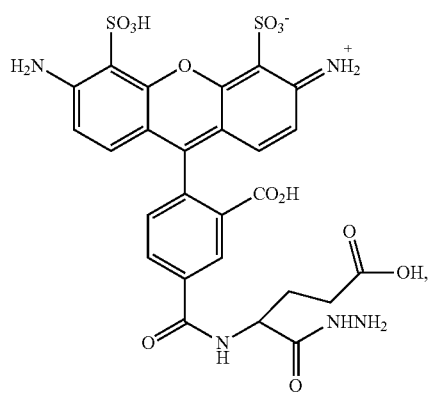

Compound 33
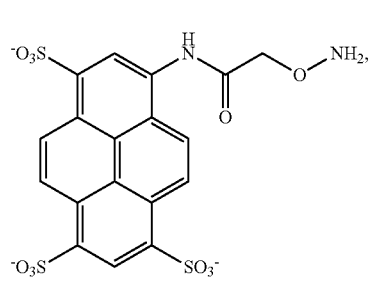

Compound 6
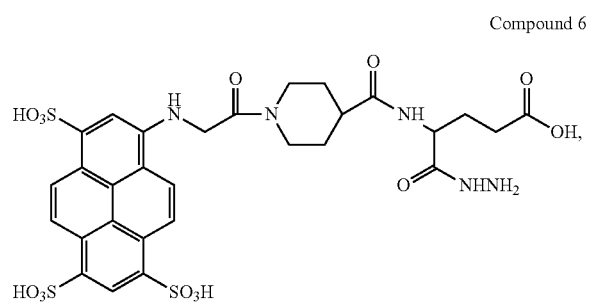

Compound 30
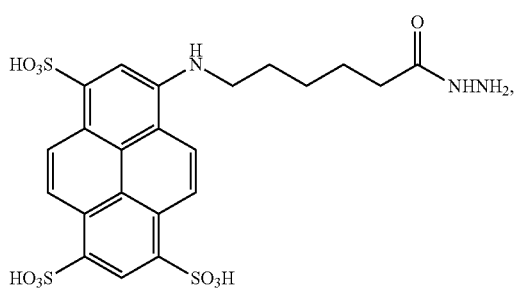 [SMILES: NNC(=O)CCCCCNc1cc(S(=O)(=O)O)c2ccc3c(S(=O)(=O)O)cc(S(=O)(=O)O)c4ccc1c2c43]

Compound 31
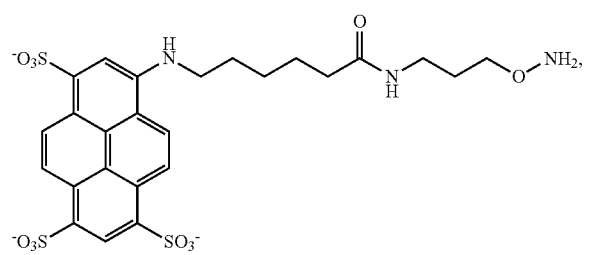

Compound 32
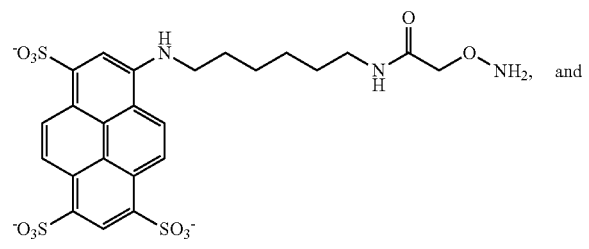
and or a salt thereof;

b) incubating the sample and the compound or composition for a sufficient amount of time to form a complex between the compound and glycan;

c) illuminating the complex with an appropriate wavelength to form an illuminated complex; and d) detecting emissions from the illuminated complex, thereby determining the presence of the glycan.

16. The method of claim 15, wherein the salt comprises a potassium, sodium, ammonium, alkylammonium, tetralkylammonium, triethylammonium, tert-butylammonium, tetralkyl-phosphonium, tetraaryl-phosphonium, lithium or cesium ion.

17. A method of labeling a glycan in a sample, the method comprising:

a) contacting the sample with a compound according to claim 1, or a composition according to claim 3;

b) incubating the sample and the compound for a sufficient amount of time to form a complex between the compound and the one or more glycans;

c) separating the sample using electrophoresis or chromatography, thereby determining the presence of the one or more glycans in the sample.

18. The method of claim 17, wherein the separating step is performed using electrophoresis.

19. The method of claim 18, wherein the electrophoresis is capillary electrophoresis.

20. The method of claim 9, wherein the capillary electrophoresis is part of a glycan analysis system.

21. The method of claim 17, wherein the separation step is performed using chromatography.

22. The method of claim 21, wherein the chromatography is high-performance liquid chromatography (HPLC) or liquid chromatography-mass spectroscopy (LC-MS).

23. A kit for labeling a glycan, wherein the kit comprises:

a) a compound according to claim 1; and b) instructions for labeling the glycan according to the method of claim 17.

24. A kit for labeling a glycan, wherein the kit comprises:

a) a compound selected from the group consisting of:

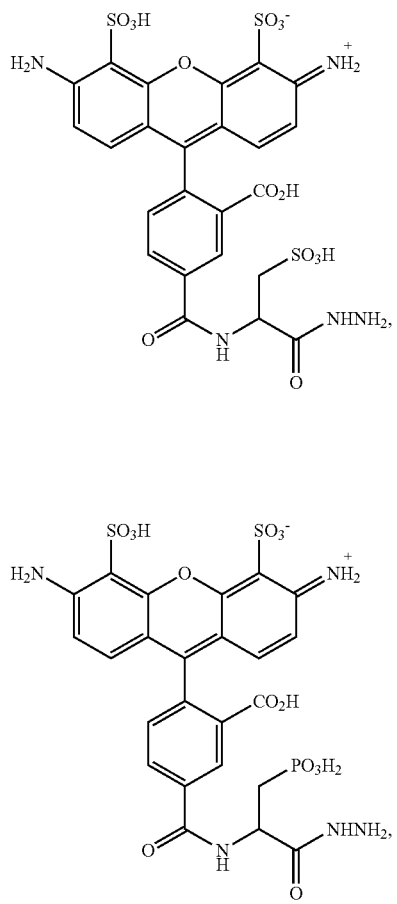

Compound 1

Compound 2

Compound 3

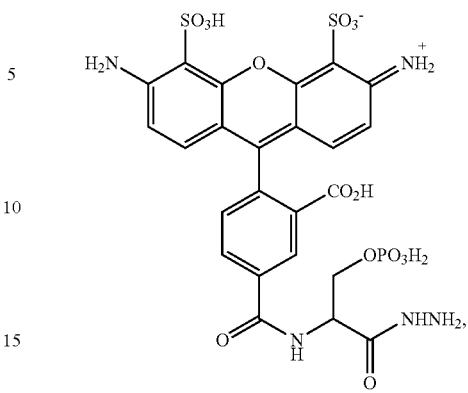

Compound 4

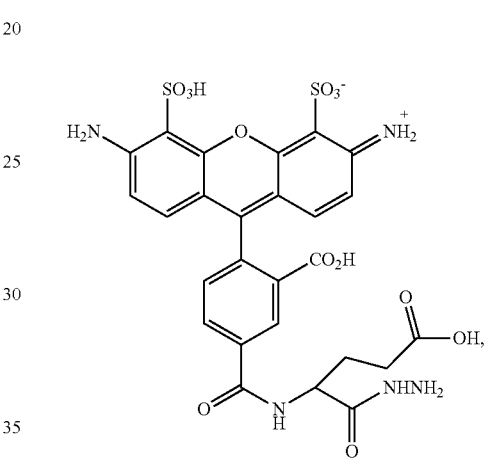

Compound 5 or a salt thereof; and b) instructions for labeling the glycan according to the method of claim 17.

25. A kit for detecting an analyte in a sample, wherein the kit comprises:

a) a compound selected from the group consisting of:

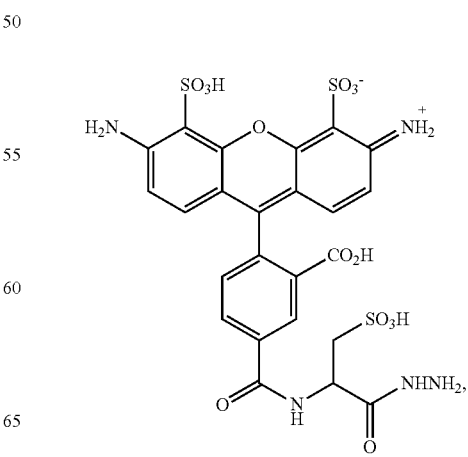

Compound 1

-continued

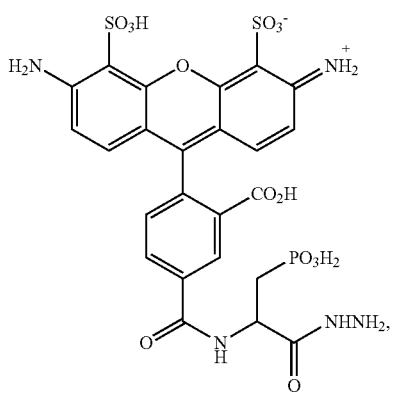

Compound 2

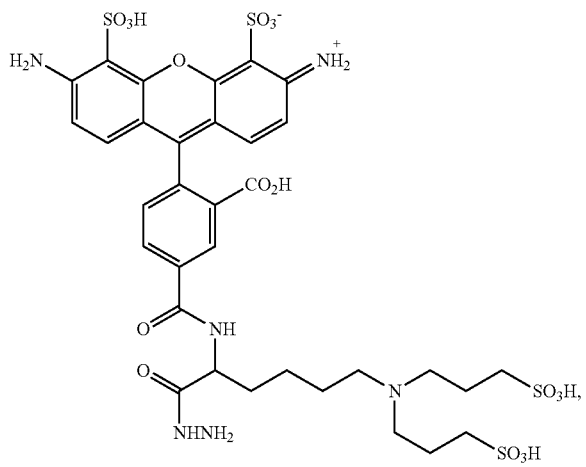

Compound 3

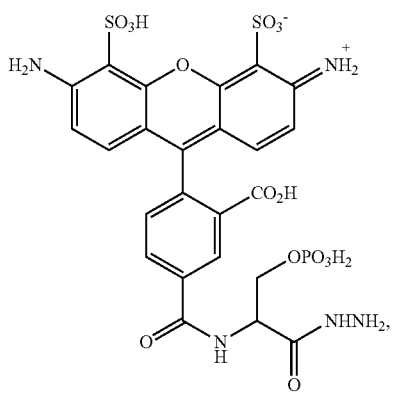

Compound 4

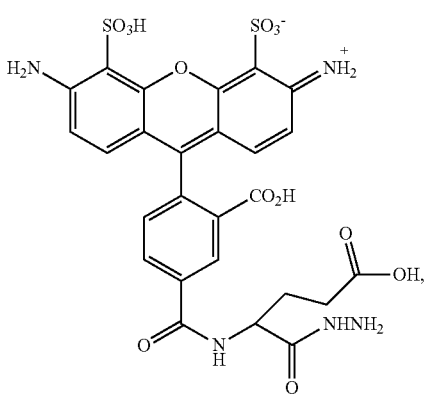

Compound 5 or a salt thereof; and b) instructions for detecting the analyte according to the method of claim 14.

26. The kit of claim 25, further comprising instructions for covalently bonding the compound to the analyte.

27. The kit of claim 25, further comprising one or more of the following: a buffering agent, a purification medium, a vial comprising the analyte, an organic solvent, one or more reagents for releasing the glycan from a biomolecule, or optionally, one or more reagents to purify the released glycan from the reaction mixture.

28. The kit of claim 27, wherein the reagent for releasing the glycan from a biomolecule is selected from a physical method, a chemical or an enzyme.

29. The kit of claim 28, wherein the enzyme is PNGase F.

30. The kit of claim 27, wherein the purification medium is selected from the group consisting of a resin, a bead, a cartridge, a solid support, a plate and a well.

31. The kit of claim 30, wherein the bead is a magnetic bead.

32. The kit of claim 25, further comprising instructions for labeling glycans in a sample in preparation of glycan analysis, the method comprising:

treating the sample with a release reagent, such as PNGase F enzyme, with an appropriate buffer under conditions suitable for the release of the glycan from the biomolecule, thereby forming a reaction mixture;

adding beads and buffer to the reaction mixture;

separating the supernatant from the beads;

washing the beads with wash buffer;

eluting the glycans from the beads with elution buffer;

performing dye labeling of the glycans using one or more dye compounds according to claim 1, thereby forming a glycan-containing solution;

optionally, removing excess dye compound using fresh beads; washing beads, separating the beads from excess dye/wash solution; and eluting glycans from the beads; and collecting the glycan-containing solution.

* * * * *

UNITED STATES PATENT AND TRADEMARK OFFICE
CERTIFICATE OF CORRECTION

PATENT NO. : 10,246,410 B2
APPLICATION NO. : 15/529437
DATED : April 2, 2019
INVENTOR(S) : Wenjun Zhou et al.

Page 1 of 2

It is certified that error appears in the above-identified patent and that said Letters Patent is hereby corrected as shown below:

In the Claims

Columns 165, Line 64, cancel the text beginning with "15. A method of detecting a glycan in a sample, the" to and ending "glycan." in Column 168, Line 28, and insert the following claim:
--15. A method of detecting a glycan in a sample, the method comprising:
a) contacting the sample with a compound selected from the group consisting of:

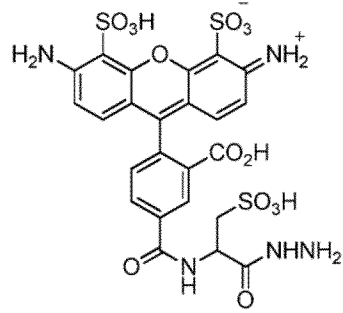
Compound 1

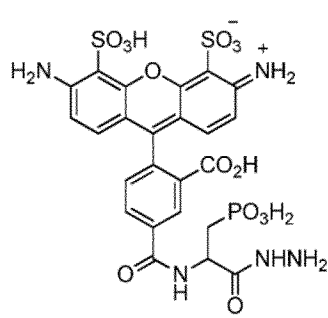
Compound 2

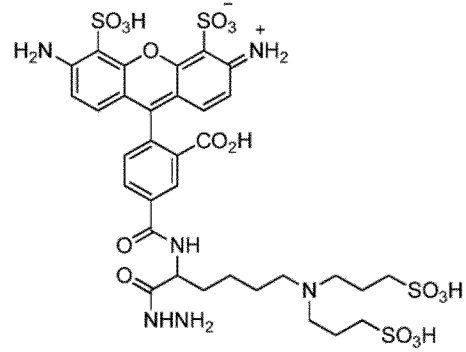
Compound 3

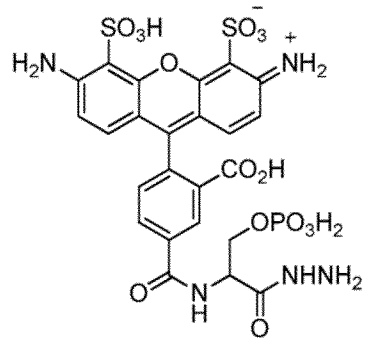
Compound 4   , and

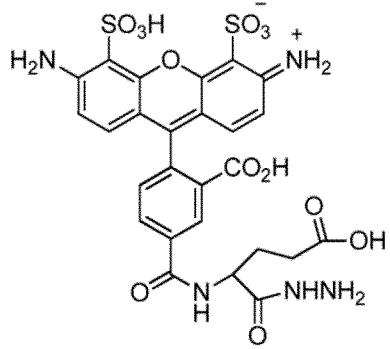
Compound 5   or a salt thereof;

Signed and Sealed this
Twenty-eighth Day of July, 2020

Andrei Iancu
*Director of the United States Patent and Trademark Office*

CERTIFICATE OF CORRECTION (continued)
U.S. Pat. No. 10,246,410 B2 b) incubating the sample and the compound or composition for a sufficient amount of time to form a complex between the compound and glycan;
c) illuminating the complex with an appropriate wavelength to form an illuminated complex; and
d) detecting emissions from the illuminated complex, thereby determining the presence of the glycan.--